United States Patent
Morishima et al.

[11] Patent Number: 5,869,428
[45] Date of Patent: Feb. 9, 1999

[54] PYRIDONESULFONYLUREA COMPOUNDS, PROCESS FOR THEIR PRODUCTION AND HERBICIDES CONTAINING THEM

[75] Inventors: Yasuo Morishima, Kobe; Shigeo Murai, Kusatsu; Yoshiyuki Aoyama, Kusatsu; Hiroshi Sasaki, Kusatsu; Hiroshi Kikugawa, Kusatsu; Soichiro Nagayama, Kusatsu; Makiko Mitani, Kusatsu, all of Japan

[73] Assignee: Ishihara Sangyo Kaisha Ltd., Osaka, Japan

[21] Appl. No.: 610,490

[22] Filed: Mar. 4, 1996

[30] Foreign Application Priority Data

Mar. 13, 1995 [JP] Japan .................... 7-081740

[51] Int. Cl.$^6$ .................. C07D 239/69; C07D 239/42; A01N 43/54
[52] U.S. Cl. .................. 504/215; 544/320; 544/324; 544/331; 544/321
[58] Field of Search ............. 504/215; 544/320, 544/324, 331, 321

[56] References Cited

U.S. PATENT DOCUMENTS

| | | | |
|---|---|---|---|
| 4,435,206 | 3/1984 | Levitt ........................ | 544/310 |
| 4,534,790 | 8/1985 | Wolf ......................... | 544/212 |
| 5,221,315 | 6/1993 | Fory et al. ................. | 544/320 |
| 5,403,814 | 4/1995 | Fory ......................... | 544/320 |
| 5,414,084 | 5/1995 | Willms ...................... | 544/320 |
| 5,457,084 | 10/1995 | Sakashita et al. ........... | 544/320 |
| 5,494,886 | 2/1996 | Kehne et al. ............... | 544/320 |
| 5,532,203 | 7/1996 | Fory et al. ................. | 544/320 |
| 5,635,451 | 6/1997 | Kehne et al. ............... | 544/320 |
| 5,663,118 | 9/1997 | Kehne et al. ............... | 544/320 |

FOREIGN PATENT DOCUMENTS

| | | |
|---|---|---|
| 0 103 543 | 3/1984 | European Pat. Off. . |
| 0 161 211 | 11/1985 | European Pat. Off. . |
| 0 164 269 | 12/1985 | European Pat. Off. . |
| 0 204 513 | 12/1986 | European Pat. Off. . |
| 0 232 067 | 8/1987 | European Pat. Off. . |
| 0 237 292 | 9/1987 | European Pat. Off. . |
| 0 547 035 | 6/1993 | European Pat. Off. . |
| WO 92/16522 | 10/1992 | WIPO . |

OTHER PUBLICATIONS

Cram and Hammond "Organic Chemistry" 2nd Edition, McGraw Hill Book Co, New York, 1964.

*Primary Examiner*—John M. Ford
*Attorney, Agent, or Firm*—Oblon, Spivak, McClelland, Maier & Neustadt, P.C.

[57] ABSTRACT

A pyridonesulfonylurea compound of the formula (I) or its salt:

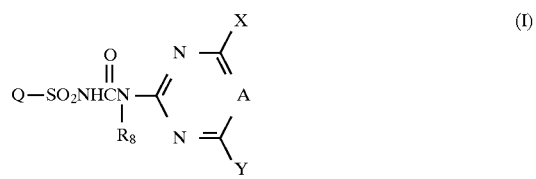

wherein Q is

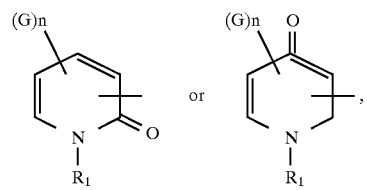

for use as a herbicide, wherein the variables are hereinbelow defined.

14 Claims, No Drawings

PYRIDONESULFONYLUREA COMPOUNDS, PROCESS FOR THEIR PRODUCTION AND HERBICIDES CONTAINING THEM

The present invention relates to novel pyridonesulfonylurea compounds useful as active ingredients for herbicides.

U.S. Pat. No. 4,435,206 discloses pyridinesulfonamide compounds, wherein an alkyl group, a trifluoromethyl group, an alkoxycarbonyl group, etc. are substituted on a pyridine ring. Further, European Patent Publication No. 232067 discloses pyridinesulfonamide compounds wherein an aminocarbonyl group is substituted on a pyridine ring. However, as compared with such compounds i.e. those having various substituents on a pyridine ring, the pyridonesulfonylurea compounds of the present invention are entirely different in the chemical structure in that they are compounds having various substituents on a pyridone ring.

Namely, the present invention provides a pyridonesulfonylurea compound of the formula (I) or its salt:

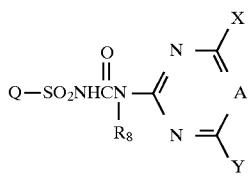

wherein Q is

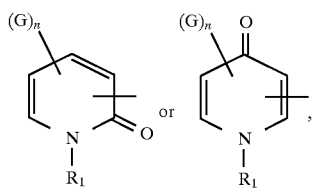

$R_1$ is a hydrogen atom, an alkyl group which may be substituted, an alkenyl group which may be substituted, an alkynyl group which may be substituted, an alkoxy group which may be substituted, an alkylthio group which may be substituted, an alkylcarbonyl group which may be substituted, an alkoxycarbonyl group which may be substituted, an alkylsulfinyl group which may be substituted, an alkylsulfonyl group which may be substituted,

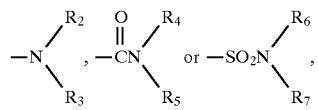

G is a halogen atom, an alkyl group which may be substituted, an alkenyl group which may be substituted, an alkynyl group which may be substituted, an alkoxy group which may be substituted, an alkylthio group which may be substituted, an alkylcarbonyl group which may be substituted, an alkoxycarbonyl group which may be substituted, an alkylsulfinyl group which may be substituted, an alkylsulfonyl group which may be substituted,

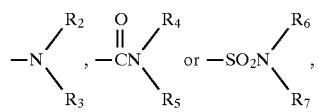

each of $R_2$ and $R_3$ which are independent of each other, is a hydrogen atom, an alkyl group, an alkylcarbonyl group, an alkylsulfinyl group or an alkylsulfonyl group, each of $R_4$, $R_5$ and $R_8$ which are independent of one another, is a hydrogen atom or an alkyl group, each of $R_6$ and $R_7$ which are independent of each other, is a hydrogen atom, an alkyl group, an alkylcarbonyl group or an alkoxycarbonyl group, n is an integer of from 0 to 3, each of X and Y which are independent of each other, is a halogen atom, an alkyl group, a haloalkyl group, an alkoxyalkyl group, an alkoxy group, a haloalkoxy group, a monoalkylamino group or a dialkylamino group, and A is CH or N, a process for its production, a herbicidal composition containing it, a method for controlling noxious weeds by its application and an intermediate compound useful for its preparation.

Now, the present invention will be described in detail with reference to the preferred embodiments.

In the above formula (I), the substituent for each of the alkyl group which may be substituted, the alkenyl group which may be substituted, the alkynyl group which may be substituted, the alkoxy group which may be substituted, the alkylthio group which may be substituted, the alkylcarbonyl group which may be substituted and the alkoxycarbonyl group which may be substituted, for $R_1$ and G, may, for example, be a halogen atom, an alkyl group, an alkoxy group, an alkylthio group, an alkylcarbonyl group, an alkoxycarbonyl group, an alkylsulfinyl group, an alkylsulfonyl group, a phenyl group which may be substituted, a benzyloxy group which may be substituted, a monoalkylamino group, a dialkylamino group, —CN or —NO$_2$, and likewise, the substituent for each of the alkylsulfinyl group which may be substituted and the alkylsulfonyl group which may be substituted, may, for example, be a halogen atom, an alkyl group, an alkoxy group, a phenyl group which may be substituted or a benzyloxy group which may be substituted. The substituent for each of the phenyl group which may be substituted and the benzyloxy group which may be substituted, as the above substituent, may, for example, be a halogen atom, an alkyl group, an alkoxy group, an alkylthio group, an alkylcarbonyl group, an alkoxycarbonyl group, an alkylsulfinyl group, an alkylsulfonyl group, a phenyl group, a benzyloxy group, a monoalkylamino group, a dialkylamino group, —CN or —NO$_2$. Further, the number of such substituents may be one or more, and in the case of a plurality of substituents, such substituents may be the same or different.

The alkyl group or the alkyl moiety contained in the definitions of $R_1$, G, $R_2$, $R_3$, $R_4$, $R_5$, $R_6$, $R_7$, $R_8$, X and Y in the formula (I), or the alkyl group or the alkyl moiety as a substituent contained in $R_1$ and G, may, for example, be a $C_{1-6}$, preferably $C_{1-4}$, linear or branched alkyl group such as a methyl group, an ethyl group, a propyl group, an isopropyl group, a butyl group, a tert-butyl group, a pentyl group or a hexyl group. Likewise, the alkenyl or alkynyl group contained in the definitions of $R_1$ and G may, for example, be a $C_{2-6}$, preferably $C_{2-4}$, linear or branched alkenyl or alkynyl group, such as a vinyl group, an allyl group, a butadienyl group, an isopropenyl group, an ethynyl group or a propynyl group. Further, the halogen atom contained in the definitions of G, X and Y, or the halogen atom as a substituent contained in $R_1$, G, X and Y may be a fluorine, chlorine, bromine or iodine atom. The number of halogen atoms as substituents, may be one or more, and in the case of a plurality of such substituted halogen atoms, they may be the same or different.

Among the pyridonesulfonylurea compounds of the formula (I) or their salts, preferred is the one wherein $R_1$ is a hydrogen atom, an alkyl group which may be substituted, an alkenyl group which may be substituted, an alkynyl group which may be substituted, an alkoxy group which may be substituted, an alkoxycarbonyl group which may be substituted, an alkylsulfonyl group which may be substituted or

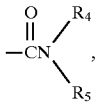

G is a halogen atom, an alkyl group which may be substituted, an alkoxy group which may be substituted, an alkylthio group which may be substituted,

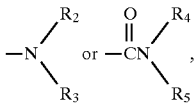

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is an integer of from 0 to 3, each of X and Y which are independent of each other, is a halogen atom, an alkyl group, an alkoxy group or a haloalkoxy group, and A is CH or N.

More preferred is the one wherein $R_1$ is a hydrogen atom; an alkyl group which may be substituted; an alkenyl group; an alkynyl group; an alkoxy group; an alkoxycarbonyl group; an alkylsulfonyl group; or

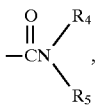

G is a halogen atom; an alkyl group which may be substituted; an alkoxy group which may be substituted; an alkylthio group;

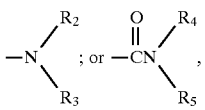

each of $R_2$ and $R_3$ which are independent of each other, is a hydrogen atom or an alkyl group, each of $R_4$ and $R_5$ which are independent of each other is an alkyl group, $R_8$ is a hydrogen atom, n is 0 or 1, each of X and Y which are independent of each other, is a halogen atom, an alkyl group or an alkoxy group, and A is CH or N.

Particularly preferred is the one wherein $R_1$ is a hydrogen atom; an alkyl group which may be substituted by at least one substituent selected from the group consisting of a halogen atom, an alkyl group, an alkoxy group, an alkylthio group, an alkylcarbonyl group, an alkoxycarbonyl group, an alkylsulfinyl group, an alkylsulfonyl group, a phenyl group and a benzyloxy group; an alkenyl group; an alkynyl group; an alkoxy group; an alkoxycarbonyl group; an alkylsulfonyl group;

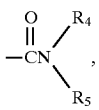

G is a halogen atom; an alkyl group which may be substituted by a halogen atom; an alkoxy group which may be substituted by a halogen atom; an alkylthio group;

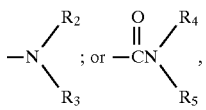

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is 0 or 1, each of X and Y which are independent of each other, is a halogen atom, an alkyl group or an alkoxy group, and A is CH or N.

The salt of a pyridonesulfonylurea compound of the formula (I) may, for example, be an alkali metal salt such as a sodium salt or a potassium salt, an alkaline earth metal salt such as a magnesium salt or calcium salt, or an ammonium salt such as a dimethylamine salt or a triethylamine salt.

The pyridonesulfonylurea compound of the above formula (I) or its salt (hereinafter referred to simply as the compound of the present invention) can be prepared by the following processes.

Namely, the pyridonesulfonylurea compound can be prepared, for example, by processes represented by the following reactions (A) to (D), and its salt can be produced by processes represented by the following reactions (A) to (D) or conventional processes for preparing salts.

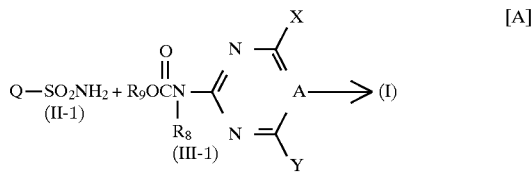

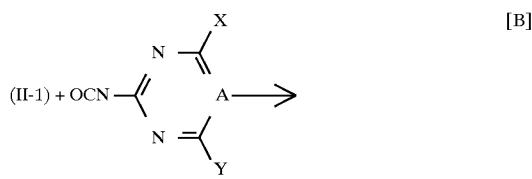

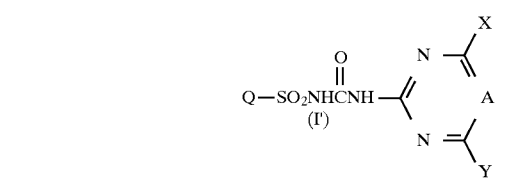

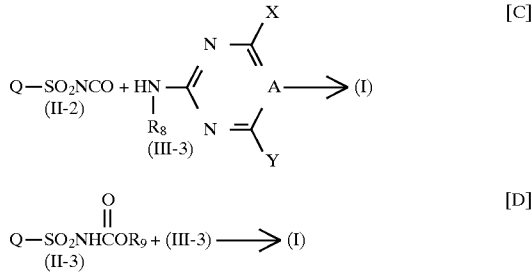

In the above reactions (A) to (D), Q, $R_8$, X, Y and A are as defined above, and $R_9$ is an alkyl group or an aryl group.

The alkyl group for $R_9$ may, for example, be a $C_{1-6}$ alkyl group which may be substituted by a halogen atom or an alkoxy group, and the aryl group may, for example, be a phenyl group or a naphthyl group, which may be substituted by a chlorine atom or a methyl group. The halogen atom and the alkoxy group as substituents may, be the same as described with respect to $R_1$.

The reaction (A) is carried out in the presence of a base, and the reactions (B), (C) and (D) may be carried out in the presence of a base, as the case requires. As the base, a tertiary amine such as triethylamine, or 1,8-diazabicyclo [5.4.0]-7-undecene, may, for example, be used.

Further, the reactions (A), (B), (C) and (D) may be carried out in the presence of a solvent, as the case requires. The solvent may, for example, be an aromatic hydrocarbon such as benzene, toluene, xylene or chlorobenzene; a cyclic or non-cyclic aliphatic hydrocarbon such as chloroform, carbon tetrachloride, methylene chloride, dichloroethane, trichloroethane, hexane or cyclohexane; an ether such as diethyl ether, dioxane or tetrahydrofuran; a nitrile such as acetonitrile, propionitrile or acrylonitrile; an ester such as methyl acetate or ethyl acetate; or a dipolar aprotic solvent such as dimethylsulfoxide, sulfolane or dimethylformamide.

The reaction temperature for the reaction (A) is usually from $-20°$ to $+100°$ C., preferably from $0°$ to $40°$ C., and the reaction time is usually from 0.01 to 24 hours, preferably from 0.1 to 1.5 hours. The reaction temperature for the reaction (B) is usually from $0°$ to $150°$ C., and the reaction time is usually from 0.1 to 24 hours. The reaction temperature for the reaction (C) is usually from $0°$ to $150°$ C., and the reaction time is usually from 0.1 to 24 hours. The reaction temperature for the reaction (D) is usually from $-20°$ to $+150°$ C., and the reaction time is usually from 0.1 to 24 hours.

The pyridone compound of the formula (II-1) in the reactions (A) and (B) is a novel intermediate compound useful for the preparation of the compound of the present invention, and it can be prepared, for example, by processes represented by the following reactions (E) to (I). The reaction (E) represents a case where the pyridone ring contained in Q in the above formula (II-1) is an α-pyridone type; the reaction (F) represents a case where the pyridone ring is an α-pyridone type and $R_1$ is an alkoxy group; and the reactions (G), (H) and (I) represent cases wherein the pyridone ring is a γ-pyridone type.

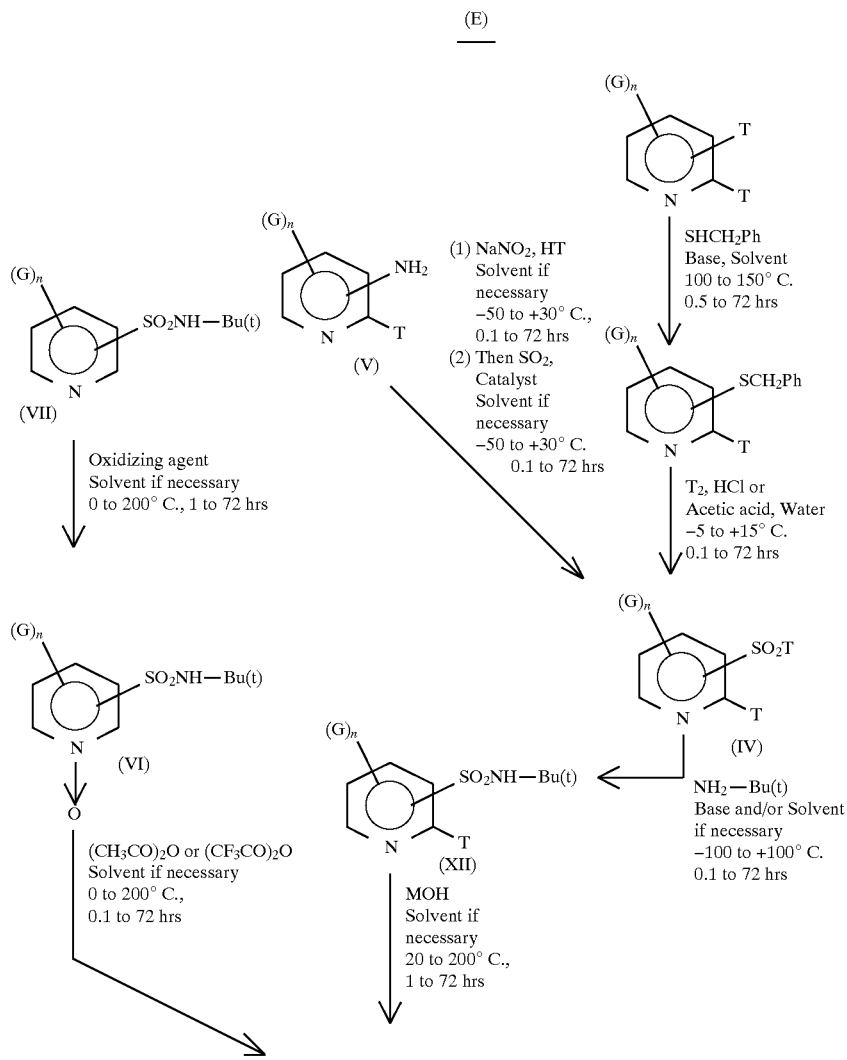

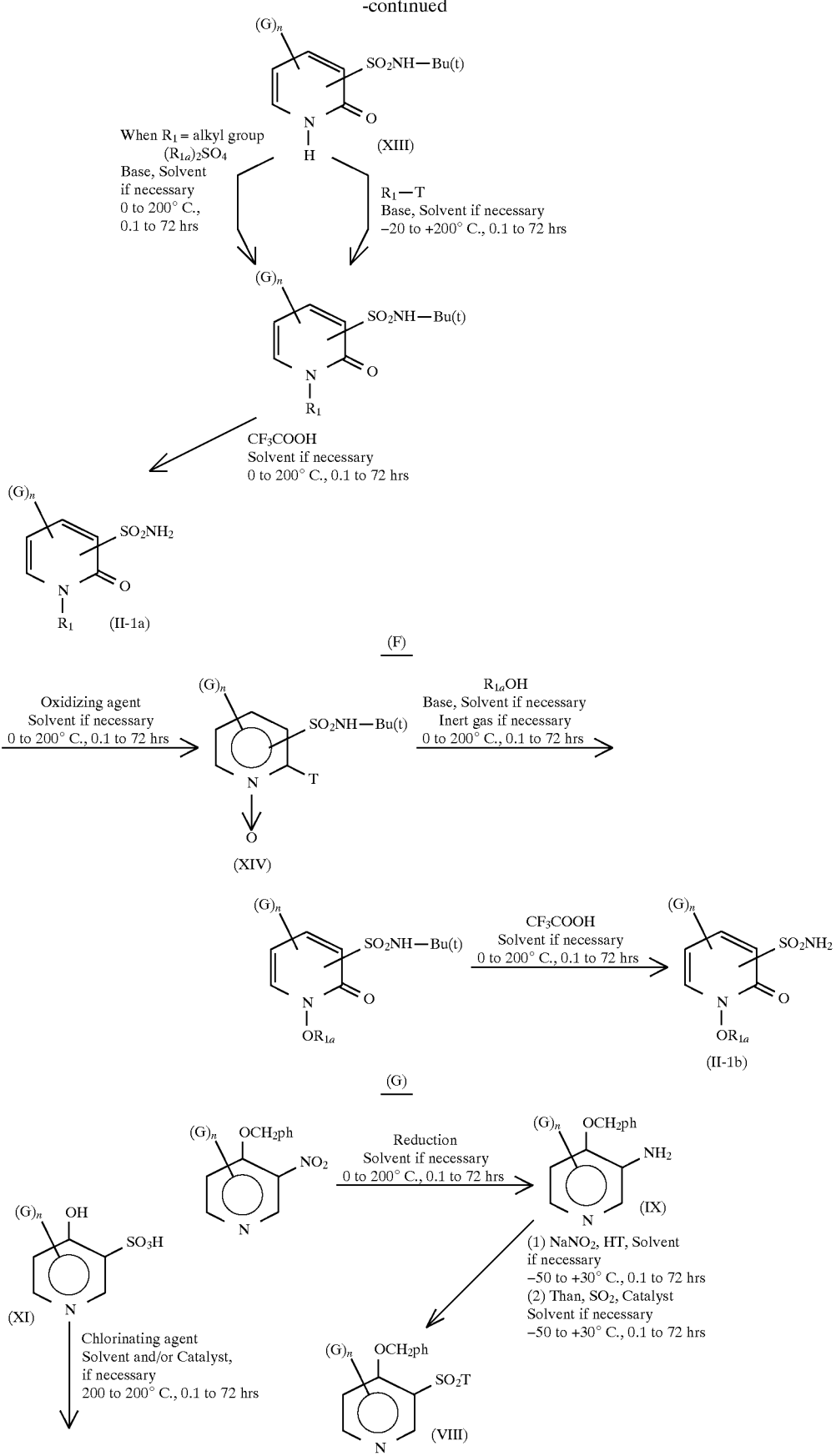

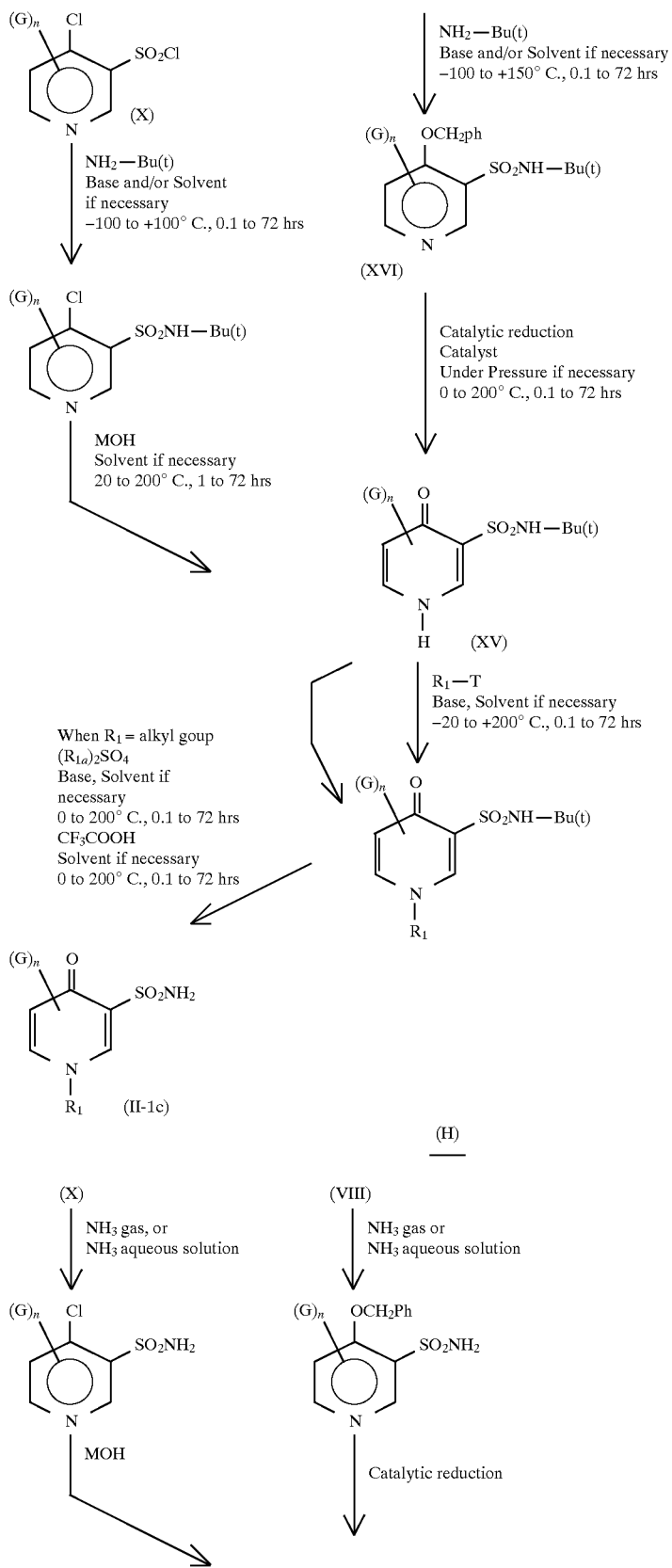

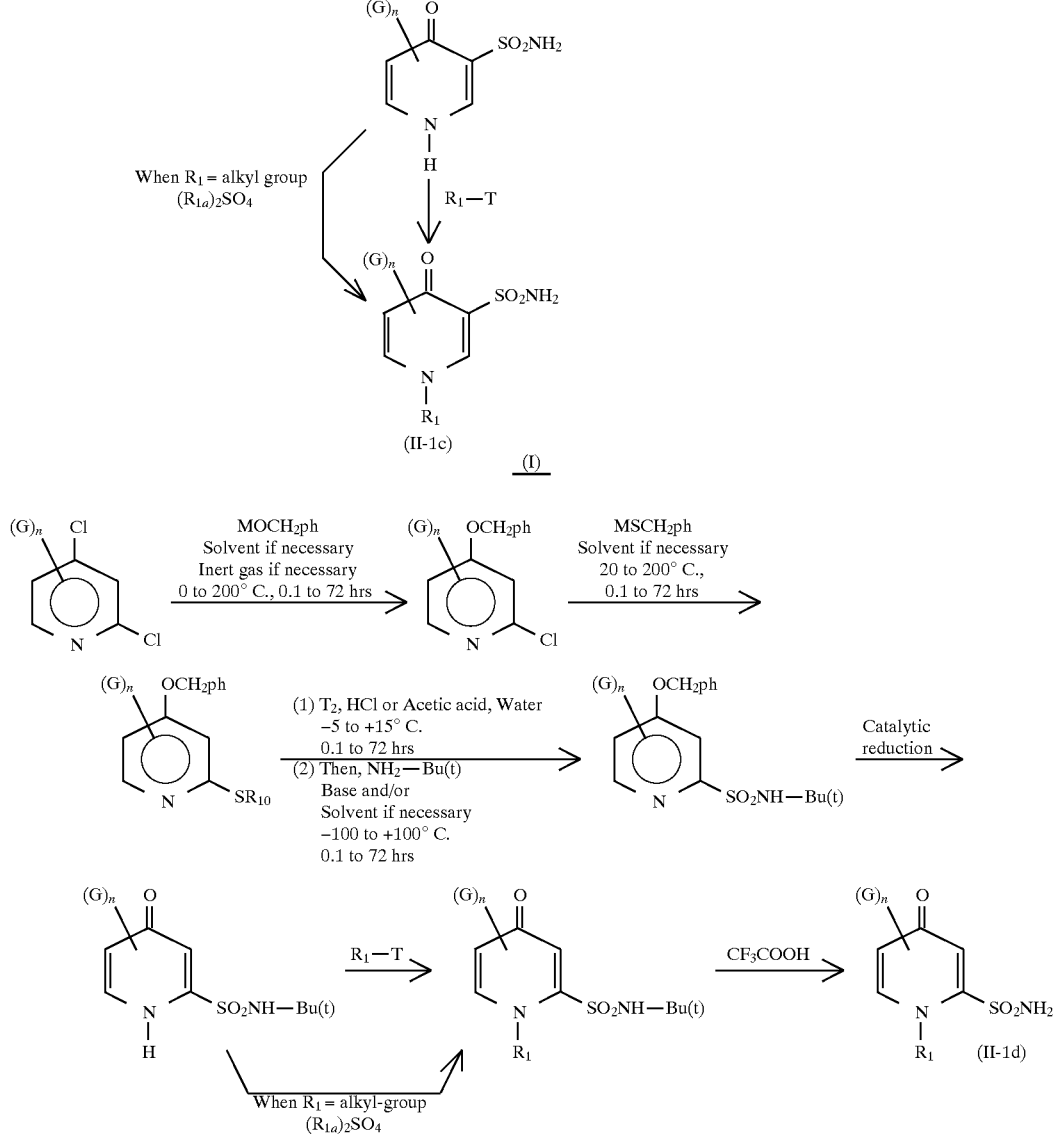

In the above reaction (E), a compound of the formula (XIII) wherein n is 1, and G is substituted at the 4-position of the pyridone ring, can also be produced by a process represented by the reaction (J). Likewise, a compound of the formula (XIII) wherein n is 1, G is substituted at the 5-position of the pyridone ring and G is a halogen atom, can be produced also by a process represented by the reaction (K). Further, a compound of the formula (VIII) in the above reaction (G) can be prepared also by a process represented by the reaction (L).

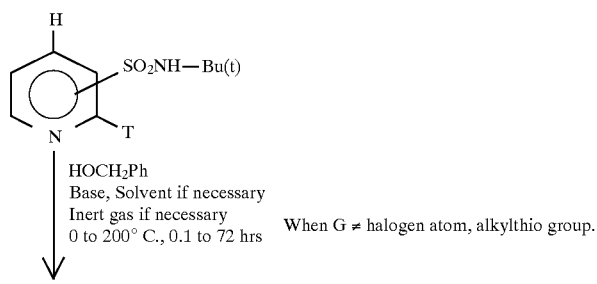

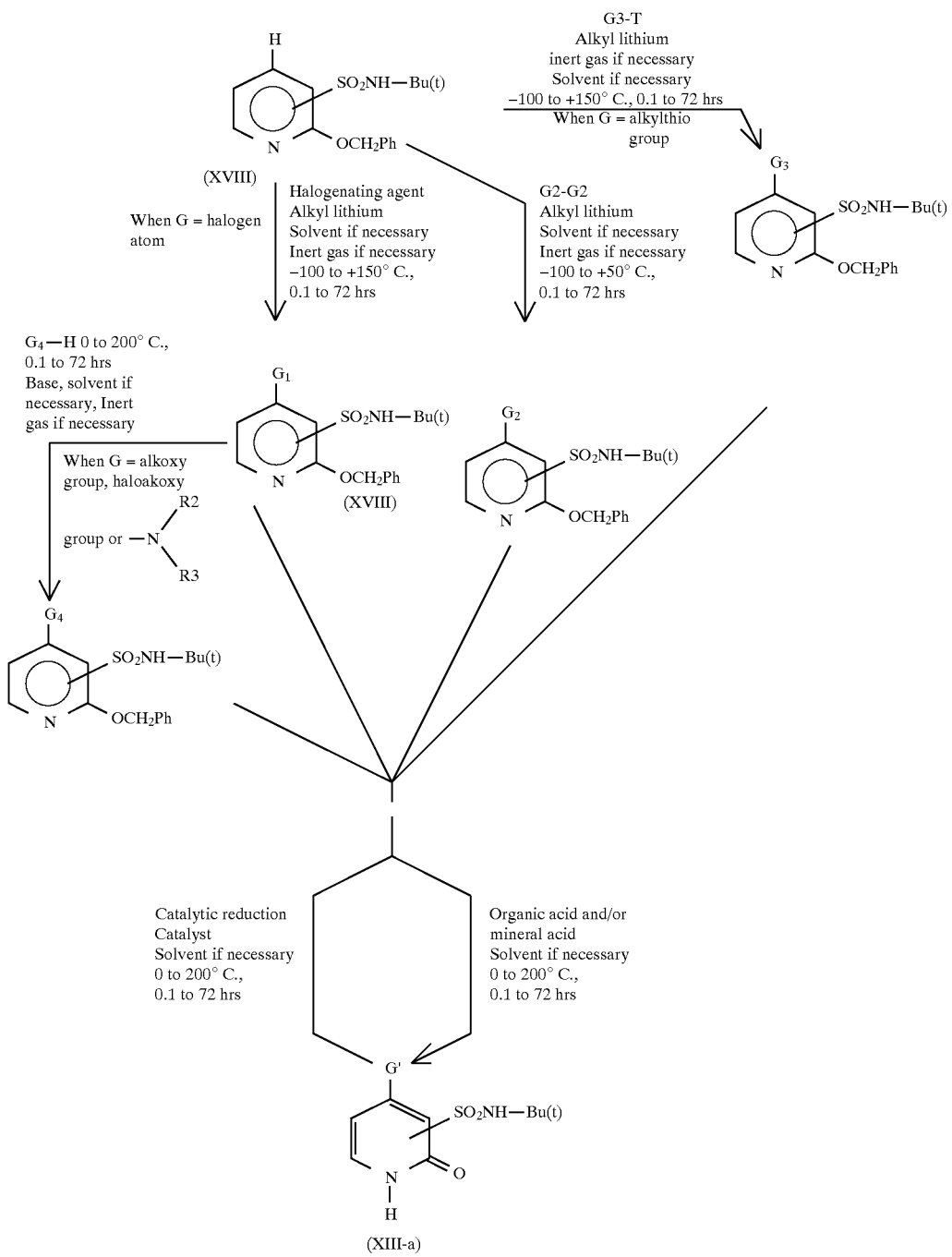

-continued

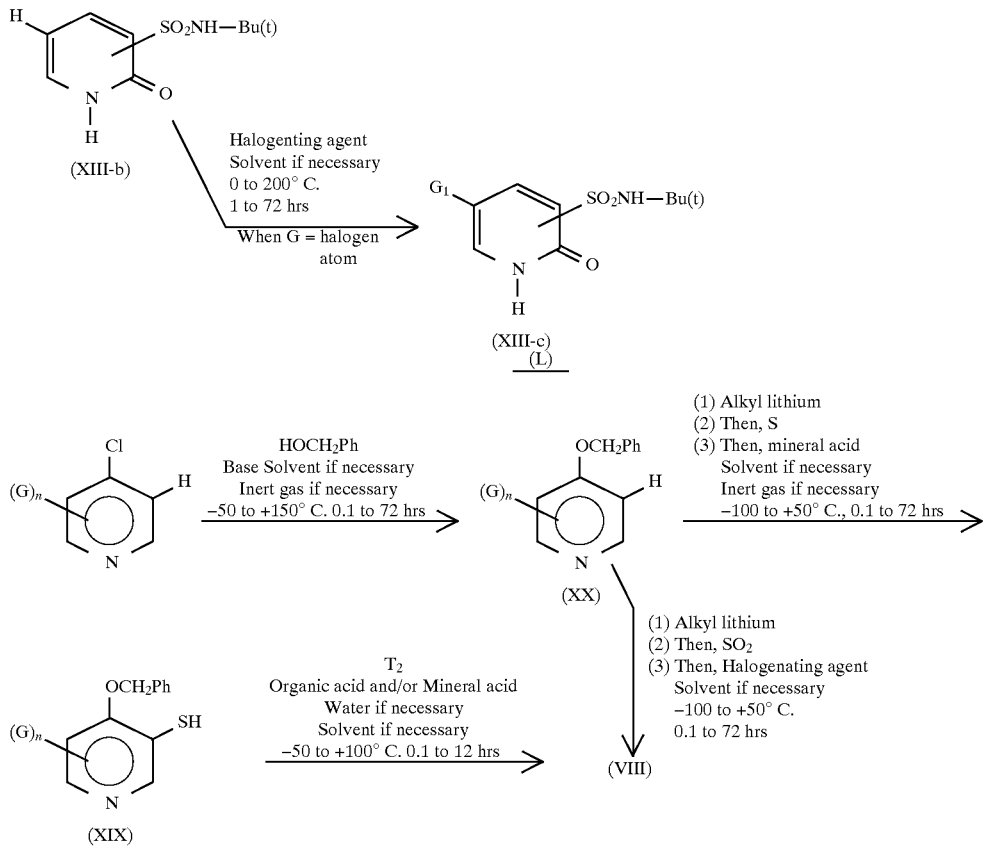

The respective steps in the reaction (H) may be conducted under reaction conditions similar to those of the corresponding reactions in the reaction (G). Further, the steps in the reaction (I) wherein no reaction conditions are indicated, may also be conducted under reaction conditions similar to those indicated in the reaction (G).

In the reactions (E) to (L), $R_1$, G and n are as defined above, T is a chlorine atom, a bromine atom or an iodine atom, M is lithium, sodium or potassium, $R_{1a}$ is an alkyl group, $R_{10}$ is a hydrogen atom or a benzyl group, $G_1$ is a halogen atom, $G_2$ is an alkylthio group, $G_3$ is an alkyl group, an alkenyl group, an alkynyl group, an alkoxy group, an alkylcarbonyl group, an alkoxycarbonyl group, an alkylsulfinyl group, an alkylsulfonyl group,

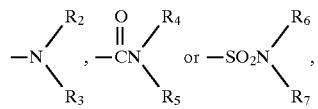

$G_4$ is an alkoxy group, a haloalkoxy group or

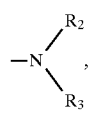

G' is a halogen atom, an alkyl group, an alkenyl group, an alkynyl group, an alkoxy group, a haloalkoxy group, an alkylthio group, an alkylcarbonyl group, an alkoxycarbonyl group, an alkylsulfinyl group, alkylsulfonyl group,

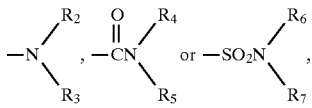

and $R_2$, $R_3$, $R_4$, $R_5$, $R_6$ and $R_7$ are as defined above. Further, Ph represents a phenyl group, and Bu(t) represents a tert-butyl group.

As the catalyst which can be used in the step of preparing (IV) from (V) in the reaction (E) and in the step for preparing (VIII) from (IX) in the reaction (G), one or more catalysts can be selected for use among e.g. copper halides such as copper (I) and (II) chloride, and copper (I) and (II) bromide, and copper (I) and (II) iodide. As the oxidizing agent which can be used in the step of preparing (VI) from (VII) in the reaction (E) and in the step of preparing (XIV) from (XII) in the reaction (F), one or more oxidizing agents are suitably selected for use among e.g. hydrogen peroxide, peracetic acid, metachloroperbenzoic acid, and manganese dioxide. As the catalyst which can be used in the step of preparing (X) from (XI) in the reaction (G), dimethylformamide may, for example, be mentioned, and as the chlorinating agent which can be used in the same step, one or more chlorinating agents are suitably selected for use among e.g. phosphorus oxychloride, phosphorus pentachloride and thionyl chloride. As the catalyst which can be used in the step of preparing (XV) from (XVI) in the reaction (G) and in the step of catalytic reduction for preparation of (XIII-a) in the reaction (J), one or more catalysts are suitably selected for use among e.g. palladium catalysts such as palladium-carbon and palladium chloride, and platinum catalysts such as platinum and platinum oxide. As the halogenating agent which can be used in the process for preparing (XVII) from (XVIII) in the reaction (J), in the step of preparing (XIII-c) from (XIII-b) in the reaction (K) and in the step of preparing (VIII) from (XX) in the reaction (L), one or more halogenating agents are suitably selected for use among e.g. N-chlorosuccinimide, N-bromosuccinimide, fluorine, chlorine, bromine and iodine. As the organic acid which can be used in the step of preparing (XIII-a) in the reaction (J), in the step of preparing (XIX) from (XX) and in the step of preparing (VIII) from (XIX) in the reaction (L), one or more organic acids are suitably selected for use among e.g. boron trifluoride, acetic acid and trifluoroacetic acid. As the mineral acid, one or more mineral acids are suitably selected for use among e.g. hydrochloric acid, sulfuric acid and nitric acid. As the inert gas which can be used in optional steps in the reactions (F), (I), (J) and (L), one or more inert gases are suitably selected for use among e.g. nitrogen, argon and helium.

As the solvent and the base which can be used in the reactions (E) to (L), the following solvent and base may, for example, be mentioned.

As the solvent, one or more solvents are suitably selected for use among e.g. aromatic hydrocarbons such as benzene, toluene, xylene and chlorobenzene; cyclic or non-cyclic aliphatic hydrocarbons such as carbon tetrachloride, methylene chloride, chloroform, dichloromethane, dichloroethane, trichloroethane, hexane and cyclohexane; ethers such as dioxane, tetrahydrofuran and diethyl ether; esters such as methyl acetate and ethyl acetate; dipolar aprotic solvents such as dimethylsulfoxide, sulfolane, dimethylacetamide, dimethylformamide, N-methylpyrrolidone, and pyridine; nitriles such as acetonitrile, propionitrile and acrylonitrile; ketones such as acetone and methyl ethyl ketone; amines such as monomethylamine, dimethylamine and triethylamine; alcohols such as methanol, ethanol, propanol and tert-butanol; organic acids such as acetic acid; aqueous ammonia; and water. As the base, one or more bases are suitably selected for use among e.g. alkali metals such as sodium and potassium; alkali metal alcoholates such as sodium methylate, sodium ethylate and potassium tertiary butylate; carbonates such as potassium carbonate and sodium carbonate; bicarbonates such as potassium bicarbonate and sodium bicarbonate; metal hydroxides such as potassium hydroxide and sodium hydroxide; metal hydrides such as potassium hydride and sodium hydride; amines such as monomethylamine, dimethylamine and triethylamine; and pyridines such as pyridine and 4-dimethylaminopyridine.

Further, a compound of the formula (XII) in the reaction (E), wherein —SO$_2$NH—Bu(t) is substituted at the 2-position of the pyridine ring, can be prepared in accordance with European Patent Publication No. 562731, p. 5 to 10. Further, the step of preparing (X) from (XI) in the reaction (G) can be carried out in accordance with Annales Pharmaceutiques Francaises, vol. 31, No. 6, p. 467–474 (1973).

The compound of the formula (II-2) in the above reaction (C) can be prepared by a process represented by the following reaction (M), and the compound of the formula (II-3) in the above reaction (D) can be prepared by a process represented by the following reaction (N).

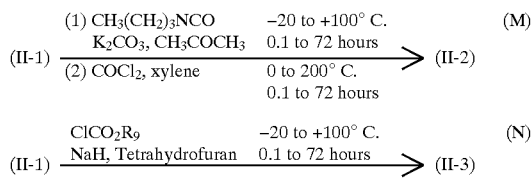

In the reaction (N), $R_9$ is as defined above.

The compound of the present invention exhibits excellent herbicidal effects when used as an active ingredient of a herbicide. It finds a wide range of applications to crop lands such as paddy fields, upland farms, orchards and mulberry fields, and non-crop lands such as forests, farm roads, playgrounds, and factory sites. The application method may suitably be selected from soil treatment application and foliar application.

The herbicidal composition containing the compound of the present invention is capable of controlling noxious weeds including grasses (or gramineae) such as barnyardgrass (*Echinochloa crus-galli* L.), crabgrass (*Digitaria sanguinalis* L.), green foxtail (*Setaria viridis* L.), goose grass (*Eleusine indica* L.), wild oat (*Avena fatua* L.), johnsongrass (*Sorghum halepense* L.), quackgrass (*Agropyron repens* L.), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium junceum*); lythraceae such as toothcup (*Rotala indica*) and red stem (*Ammannia multiflora*); and broadleaves such as velvetleaf (*Abutilon theophrasti* MEDIC.), tall morningglory (*Ipomoea purpurea* L.), common lambsquarters (*Chenopodium album* L.), prickly sida (*Sida spinosa* L.), common purslane (*Portulaca oleracea* L.), slender amaranth (*Amaranthus viridis* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorghum (*Sorghum* spp.), rape (Brassica spp.), sunflower (*Helianthus annuus* L.), sugar beet (*Beta vulgaris* L.), sugarcane (*Saccharum officinarum* L.), turfgrass (e.g. Zoysia spp.), peanut (*Arachis hypogaea* L.) or flax (*Linum usitatissimum* L.)

The herbicidal composition containing the compound of the present invention is usually formulated by mixing the compound with various agricultural adjuvants and used in the form of a formulation such as a dust, granules, water-dispersible granules, a wettable powder, an emulsifiable concentrate, a water-based suspension concentrate, an oil-based suspension concentrate, water soluble granules (or powder), tablets or capsules. However, so long as it is suitable for the purpose of the present invention, it may be formulated into any type of formulation which is commonly used in this field.

Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkyl aryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.1:99.9 to 95:5, preferably from 0.2:99.8 to 85:15.

The dose of the herbicidal composition of the present invention can not generally be defined, since it may vary depending upon the weather condition, the soil condition, the type of the formulation, the types of the weeds to be controlled, the season for the application, etc. However, it is usually applied so that the compound of the present invention would be applied in an amount of from 0.5 to 5000 g/ha, preferably from 1 to 1000 g/ha, more preferably from 5 to 500 g/ha. The present invention covers such a method for controlling noxious weeds by application of such a herbicidal composition.

The herbicidal compositions of the present invention may be used in admixture with or in combination with other agricultural chemicals, fertilizers or phytotoxicity-reducing agents. In such a case, they may exhibit even better effects or activities. As other agricultural chemicals, herbicides, fungicides, antibiotics, plant hormones or insecticides may, for example, be mentioned. Especially with a herbicidal composition having the compound of the present invention used in admixture with or in combination with one or more active ingredients of other herbicides, it is possible to improve the herbicidal activities, the season for the application and the range of applicable weed types. Further, the compound of the present invention and an active ingredient of other herbicide may be separately formulated, so that they may be mixed for use at the time of application, or both may be formulated together. The present invention covers such herbicidal compositions.

The mixed ratio of the compounds of the present invention with the active ingredients of other herbicides can not generally be defined, since it varies depending upon the weather condition, the soil condition, the type of the formulation, the season for the application, the manner of the application, etc. However, one active ingredient of other herbicide may be incorporated usually in an amount of from 0.001 to 10000 parts by weight, preferably from 0.01 to 100 parts by weight, per part by weight of the compound of the present invention. Further, the total dose of all of the active ingredients is usually from 0.1 to 10000 g/ha, preferably from 0.2 to 5000 g/ha. The present invention covers a method for controlling noxious weeds by application of such herbicidal compositions.

As the active ingredients of other herbicides, the following (common names) may be mentioned.

(1) Those which are believed to exhibit herbicidal effects as a result of their ability to mimic the activity of endogenous auxin, including a phenoxy acetic acid compounds such as 2,4-D, MCPA, MCPB or naproanilide, an aromatic carboxylic acid compounds such as 2,3,6-TBA, dicamba or picloram, and other compounds such as benazolin or quinclorac.

(2) Those which are believed to exhibit herbicidal effects by inhibiting photosystem of plants, including a urea compound such as diuron, linuron, isoproturon or metobenzuron, triazine compound such as simazine, atrazine, atratone, simetryn, prometryn, dimethametryn or metribuzin, an uracil compound such as bromacil or lenacil, an anilide compound such as propanil or cypromid, a carbamate compound such as swep or phenmedipham, a hydroxybenzonitrile compound such as bromoxynil or ioxynil, and other compounds such as pyridate or bentazon.

(3) A quaternary ammonium salt compound such as paraquat or diquat, which is believed to exhibit herbicidal effects by oxygen activation and oxygen reduction.

(4) Those which are believed to exhibit herbicidal effects by inhibiting chlorophyll biosynthesis of plants and abnormally accumulating a photooxidizer of membrane lipids in the plant body, including a diphenyl ether compound such as nitrofen, chlomethoxyfen, bifenox, acifluorfen-sodium or fomesafen, a cyclic imido compound such as chlorphthalim, flumioxadine or flumicloracpentyl, and other compounds such as oxadiazon, sulfentrazone or thidiazimin.

(5) Those which are believed to exhibit herbicidal effects characterized by bleaching by inhibiting pigment biosynthesis of plants such as carotenoids, including a pyridazinone compound such as norflurazon or metflurazon, a pyrazole compound such as pyrazolate, pyrazoxyfen or benzofenap, and other compounds such as fluridone, flurtamone, diflufenican, methoxyphenone, clomazone, sulcotrione or isoxaflutole.

(6) Those which exhibit herbicidal effects specifically to grass weeds, including an aryloxyphenoxypropionic acid compound such as diclofop-methyl, pyriphenop-sodium, fluazifop-butyl, haloxyfop-methyl, quizalofop-ethyl or cyhalofop-butyl, and a cyclohexanedione compound such as alloxydim-sodium, clethodim, sethoxydim or tralkoxydim.

(7) Those which are believed to exhibit herbicidal effects by inhibiting an amino acid biosynthesis of plants, including a sulfonylurea compound such as chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, flazasulfuron, rimusulfuron, nicosulfuron, imazosulfuron, cyclosulfamuron, prosulfuron, flupyrsulfuron, trisulfuron-methyl or halosulfuron, a triazolopyrimidinesulfoneamide compound such as flumetsulam or metosulam, an imidazolinone compound such as imazapyr, imazethapyr, imazaquin, imazamox or imazameth, a pyrimidinylsalicylic acid compound such as pyrithiobac-sodium, bispyribac-sodium or pyriminobac-methyl, and other compounds such as glyphosate-ammonium, glyphosate-isopropylamine, glyfosinate-ammonium or bialaphos.

(8) Those which are believed to exhibit herbicidal effects by inhibiting cell division of plants, including a dinitroaniline compound such as trifluralin, oryzalin, nitralin or pendimethalin, an organic phosphorus compound such as amiprofos-methyl, butamifos, anilofos or piperophos, a phenylcarbamate compound such as chlorpropham or barban, a cumylamine compound such as daimuron, cumyluron or bromobutide and other compounds such as asulam or dithiopyr.

(9) Those which are believed to exhibit herbicidal effects by inhibiting protein biosynthesis or lipid biosynthesis of plants, including a thiocarbamate compound such as EPTC, butylate, molinate, dimepiperate, esprocarb, thiobencarb or pyributicarb, or chloroacetamide compound such as alachlor, butachlor, pretilachlor, metolachlor, thenylchlor or dimethenamid, and other compounds such as a ethobenzanide, mefenacet, thiafluamide, tridiphane or cafenstrole.

Now, the present invention will be described in further detail with reference to Examples. However, it should be understood that the present invention is by no means restricted to such specific Examples.

Firstly, Preparation Examples for the compounds of the present invention will be described.

PREPARATION EXAMPLE 1

Preparation of N-[(4,6-dimethoxypyrimidin-2-yl) aminocarbonyl]-[1-(n-propyl)-2(1H)-pyridone]-3-sulfonamide (Compound No. 21, as given hereinafter)

(1) 50.0 g of 3-amino-2-chloropyridine, 100 ml of hydrochloric acid and 40 ml of acetic acid were mixed, and 100 ml of an aqueous solution containing 29.5 g of sodium nitrite was dropwise added thereto at a temperature of not higher than 5° C. with stirring. The mixture was reacted at the same temperature for one hour. The obtained suspension was gradually added to 400 ml of acetic acid containing 3 g of cupric chloride and 75 g of sulfur dioxide gas at 0° C. with stirring, followed by a reaction at the same temperature for 30 minutes to obtain a reaction mixture containing 2-chloro-3-chlorosulfonylpyridine.

Water was added to the obtained reaction mixture, and then the mixture was extracted with methylene chloride. Then, the extract layer was thoroughly washed with water and dried over anhydrous sodium sulfate. Then, 62 g of tert-butylamine was dropwise added thereto at room temperature, and the mixture was reacted at the same temperature for 30 minutes.

After completion of the reaction, the reaction mixture was filtered. From the obtained filtrate, methylene chloride was distilled off under reduced pressure to obtain 67.6 g of 3-tert-butylaminosulfonyl-2-chloropyridine having a melting point of from 134° to 135° C.

(2) 20 g of 3-tert-butylaminosulfonyl-2-chloropyridine, 20 g of potassium hydroxide and 150 ml of tert-butyl alcohol were mixed and reacted at 140° C. overnight in an autoclave.

After completion of the reaction, the reaction mixture was left to cool, then put into water and acidified with hydrochloric acid. Then, the mixture was extracted with methylene chloride, and the extract layer was dried over anhydrous sodium sulfate, whereupon methylene chloride was distilled off under reduced pressure. The obtained crystals were washed with methanol to obtain 14.3 g of 3-tert-butylaminosulfonyl-2(1H)-pyridone having a melting point of from 220° to 222° C.

(3) 600 mg of 3-tert-butylaminosulfonyl-2(1H)-pyridone, 530 mg of n-propyl iodide, 720 mg of anhydrous potassium carbonate and 20 ml of dimethylformamide were mixed and reacted at a temperature of from 80° to 100° C. for 1.5 hours.

After completion of the reaction, water was added to the reaction mixture, and then hydrochloric acid was added to acidify the mixture. Then, the mixture was extracted with methylene chloride, and the extract layer was dried over anhydrous sodium sulfate, whereupon methylene chloride was distilled off under reduced pressure. The obtained residue was purified by silica gel column chromatography (developing solvent: ethyl acetate/hexane=1/1) to obtain 580 mg of 1-(n-propyl)-3-tert-butylaminosulfonyl-2(1H)-pyridone having a melting point of from 118° to 120° C.

(4) 580 mg of 1-(n-propyl)-3-tert-butylaminosulfonyl-2 (1H)pyridone and 3 ml of trifluoroacetic acid were mixed and reacted at room temperature overnight.

After completion of the reaction, trifluoroacetic acid was distilled off under reduced pressure from the reaction mixture. The obtained residue was washed with diethyl ether to obtain 326 mg of 1-(n-propyl)-3-aminosulfonyl-2(1H)-pyridone (Intermediate No. 4 as given hereinafter) having a melting point of from 140° to 142° C.

(5) 320 mg of 1-(n-propyl)-3-aminosulfonyl-2(1H)-pyridone, 330 mg of phenyl N-(4,6-dimethoxypyrimidin-2-yl)carbamate and 10 ml of anhydrous dimethylformamide were mixed, and 218 mg of 1,8-diazabicyclo[5.4.0]-7-undecene was added thereto. The mixture was then reacted at room temperature for 30 minutes.

After completion of the reaction, the reaction mixture was put into water, and insoluble matters were separated off, and the solution was adjusted to be weakly acidic by concentrated hydrochloric acid. The crystals thereby precipitated were collected by filtration and dried to obtain 312 mg of the desired product having a melting point of from 180° to 183° C.

PREPARATION EXAMPLE 2

Preparation of N-[(4,6-dimethoxypyrimidin-2-yl) aminocarbonyl]-[1-methyl-5 2(1H)-pyridone]-6-sulfonamide (Compound No. 287, as given hereinafter)

(1) 5 g of 2-tert-butylaminosulfonyl-6-chloropyridine, 5 g of potassium hydroxide and 50 ml of tert-butanol were mixed and reacted at 150° C. for 3 hours in an autoclave.

After completion of the reaction, the reaction mixture was cooled to room temperature, then put into water and extracted with ethyl acetate. The obtained extract layer was dried over anhydrous sodium sulfate, whereupon ethyl acetate was distilled off under reduced pressure, to obtain 3.9 g of 6-tert-butylaminosulfonyl-2(1H)-pyridone having a melting point of from 197° to 198° C.

(2) A solution having 350 mg of metal sodium dissolved in 5 ml of methanol, 2.3 g of 6-tert-butylaminosulfonyl-2 (1H)-pyridone and 2 ml of dimethylsulfate were mixed and reacted at room temperature for 30 minutes.

After completion of the reaction, the reaction mixture was put into water and extracted with ethyl acetate. The obtained extract layer was dried over anhydrous sodium sulfate, whereupon ethyl acetate was distilled off under reduced pressure. Then, the residue was purified by silica gel column chromatography (developing solvent: ethyl acetate/hexane= 4/1) to obtain 400 mg of 1-methyl-6-tert-butylaminosulfonyl-2(1H)-pyridone having a melting point of from 135° to 136° C.

(3) 300 mg of 1-methyl-6-tert-butylaminosulfonyl-2(1H)-pyridone and 1 ml of trifluoroacetic acid were mixed and reacted under reflux for 6 hours.

After completion of the reaction, trifluoroacetic acid was distilled off under reduced pressure from the reaction mixture. The obtained residue was washed with diethyl ether and then dried to obtain 150 mg of 1-methyl-6-aminosulfonyl-2(1H)-pyridone (Intermediate No. 195, as given hereinafter) having a melting point of from 177° to 178° C.

(4) 100 mg of 1-methyl-6-aminosulfonyl-2(1H)-pyridone, 150 mg of phenyl N-(4,6-dimethoxypyrimidin-2-yl) carbamate and 5 ml of acetonitrile were mixed, and 100 mg of 1,8-diazabicyclo[5.4.0]-7-undecene was added thereto. Then, the mixture was reacted at room temperature for 30 minutes.

After completion of the reaction, the reaction mixture was put into ice water and adjusted to be weakly acidic by hydrochloric acid. Then, precipitated crystals were collected by filtration, washed with water and dried to obtain 130 mg of the desired product having a melting point of from 162° to 165° C.

PREPARATION EXAMPLE 3

Preparation of N-[(4,6-dimethoxypyrimidin-2-yl) aminocarbonyl]-[1-methyl-4(1H)-pyridone]-3-sulfonamide (Compound No. 313, as given hereinafter)

(1) 80 g of phosphorus pentachloride, 80 g of phosphorus oxychloride and 20 g of 4-hydroxy-3-pyridinesulfonic acid were mixed and reacted under reflux for 4.5 hours to obtain a reaction mixture containing 4-chloro-3-chlorosulfonylpyridine.

From the obtained reaction mixture, excess phosphorus oxychloride was distilled off under reduced pressure. The residue was put into ice of about 200 g and extracted with dichloromethane. The obtained extract layer was washed with a saturated sodium chloride aqueous solution, then dried over anhydrous sodium sulfate and cooled with ice. Then, 20.8 g of tert-butylamine was dropwise added at a temperature of not higher than 25° C., and the mixture was reacted at room temperature overnight.

After completion of the reaction, ice water was added to the reaction mixture, followed by liquid separation. The aqueous layer was extracted with dichloromethane. The obtained dichloromethane layer was combined with the organic layer, whereupon the organic layer was washed with a saturated sodium chloride aqueous solution and dried over anhydrous sodium sulfate. Then, dichloromethane was distilled off to obtain 12.8 g of 3-tert-butylaminosulfonyl-4-chloropyridine having a melting point of from 126° to 132° C.

(2) 4.97 g of 3-tert-butylaminosulfonyl-4-chloropyridine, 5.0 g of potassium hydroxide and 50 ml of tert-butanol were mixed and reacted at 140° C. for 2 hours in an autoclave.

After completion of the reaction, tert-butanol was distilled off from the reaction mixture, and ice was added thereto. The mixture was neutralized with concentrated hydrochloric acid. The mixture was extracted with dichloromethane, and the extract layer was washed with a saturated sodium chloride aqueous solution and dried over anhydrous sodium sulfate. Then, dichloromethane was distilled off, and the obtained yellow solid was washed with diethyl ether to obtain 3.54 g of 3-tert-butylsulfonyl-4(1H)-pyridone having a melting point of from 205° to 215° C.

(3) 1.15 g of 3-tert-butylsulfonyl-4(1H)-pyridone, 5 ml of dimethylformamide, 0.73 g of potassium carbonate and 1.84 g of iodomethane were mixed and reacted at 80° C. for 7 hours in an autoclave.

After completion of the reaction, dimethylformamide was distilled off under reduced pressure from the reaction mixture. Then, ice water was added thereto, and the mixture was extracted with dichloromethane. The obtained extract layer was washed with a saturated sodium chloride aqueous solution and dried over anhydrous sodium sulfate, whereupon dichloromethane was distilled off. The obtained residue was purified by silica gel column chromatography (developing solvent: methanol/dichloromethane=3/97) to obtain 1.16 g of 1-methyl-3-tert-butylaminosulfonyl-4(1H)-pyridone having a melting point of from 183° to 185° C.

(4) 1.0 g of 1-methyl-3-tert-butylaminosulfonyl-4(1H)-pyridone and 10 ml of trifluoroacetic acid were mixed and reacted under reflux for 3 hours.

After completion of the reaction, trifluoroacetic acid was distilled off under reduced pressure from the reaction mixture. The obtained residue was crystallized from diethyl ether. The crystals were washed with diethyl ether to obtain 0.71 g of 1-methyl-3-aminosulfonyl-4(1H)-pyridone (Intermediate No. 206, as given hereinafter) having a melting point of 216° C. (decomposed).

(5) 226 mg of 1-methyl-3-aminosulfonyl-4(1H)-pyridone, 360 mg of phenyl N-(4,6-dimethoxypyrimidin-2-yl) carbamate and 3 ml of anhydrous acetonitrile were mixed, and 200 mg of 1,8-diazabicyclo[5.4.0]-7-undecene was added thereto. Then, the mixture was reacted at room temperature for 1.5 hours.

After completion of the reaction, water was added to the reaction mixture. Then, concentrated hydrochloric acid was added thereto until the mixture became acidic. Precipitated crystals were collected by filtration, washed with water, dried and then washed with ethyl acetate to obtain 237 mg of the desired product having a melting point of 161° C. (decomposed).

PREPARATION EXAMPLE 4

Preparation of N-[(4,6-dimethoxypyrimidin-2-yl) aminocarbonyl]-[1-ethoxy-2(1H)-pyridone]-3-sulfonamide (Compound No. 95, as given hereinafter)

(1) To 50 ml of acetic acid, 5 g of 3-tert-butylaminosulfonyl-2-chloropyridine and 25 ml of an aqueous hydrogen peroxide solution were added, and the mixture was reacted at 100° C. for one hour with stirring. Then, 25 ml of aqueous hydrogen peroxide solution was added twice with an interval of one hour at the same temperature, and the reaction was conducted for 2 hours. Then, at the same temperature, the reaction was further carried out for 2 hours.

After completion of the reaction, the reaction mixture was left to cool and then put into water. Then, the mixture was extracted with methylene chloride, and the extract layer was dried over anhydrous sodium sulfate, whereupon methylene chloride was distilled off under reduced pressure. The obtained crystals were washed with a solvent mixture of n-hexane and ethyl acetate to obtain 3 g of 3-tert-butylaminosulfonyl-2-chloropyridine N-oxide.

(2) 250 mg of metal sodium was added to 50 ml of dried ethanol, followed by stirring in a nitrogen atmosphere. After the metal sodium dissolved completely, 2.5 g of 3-tert-butylaminosulfonyl- 2-chloropyridine N-oxide was added, and the mixture was reacted under reflux for one hour.

After completion of the reaction, the reaction mixture was left to cool, put into water and acidified with hydrochloric acid. Then, the mixture was extracted with ethyl acetate, and the extract layer was dried over anhydrous sodium sulfate, whereupon ethyl acetate was distilled off under reduced pressure. The obtained residue was purified by silica gel column chromatography (developing solvent: ethyl acetate/n-hexane=2/1) to obtain 1.5 g of 1-ethoxy-3-tert-butylaminosulfonyl-2(1H)-pyridone.

(3) Using 1-ethoxy-3-tert-butylaminosulfonyl-2(1H)-pyridone obtained in the above step (2), 90 mg of the desired product having a melting point of from 180° to 182° C. was prepared in the same manner as in Preparation Example 1(4) and (5).

PREPARATION EXAMPLE 5

Preparation of N-[(4,6-dimethoxypyrimidin-2-yl) aminocarbonyl]-[1-ethyl-4-ethoxy-2(1H)-pyridone]-3-sulfonamide (Compound No. 496, as given hereinafter)

(1) 11.2 g of 60% sodium hydride was washed with n-hexane, hexane, and 250 ml of dimethylformamide was added thereto. The mixture was stirred under a nitrogen atmosphere to obtain a uniform mixture. Then, a solution having 30 g of benzyl alcohol dissolved in 50 ml of dimethylformamide, was gradually dropwise added thereto under cooling, followed by stirring at room temperature for 3 hours. Then, under cooling, 20 g of 3-tert-butylaminosulfonyl-2-chloropyridine was added thereto, and the mixture was reacted at room temperature for 2 days with stirring.

After completion of the reaction, the reaction mixture was put into water and acidified with hydrochloric acid. Precipitated crystals were collected by filtration and washed with distilled water. The obtained crystals were dried to obtain 21 g of 3-tert-butylaminosulfonyl-2-benzyloxypyridine having a melting point of from 107° to 108° C.

(2) 10 g of 3-tert-butylaminosulfonyl-2-benzyloxypyridine was dissolved in 200 ml of tetrahydrofuran, and the solution was cooled to −70° C. Then, 40 ml of n-butyl lithium was gradually added thereto. Then, the reaction was continued at the same temperature for further 30 minutes with stirring, and 8.5 g of N-chlorosuccinimide was added. Then, the reaction was further continued at the same temperature for one hour with stirring. Then, the mixture was gradually returned to room temperature to complete the reaction.

After completion of the reaction, the reaction mixture was put into water and extracted with ethyl acetate. The extract layer was dried over anhydrous sodium sulfate, whereupon ethyl acetate was distilled off under reduced pressure. The obtained residue was purified by silica gel column chromatography (developing solvent: n-hexane/ethyl acetate=3/1) to obtain 6 g of 4-chloro-3-tert-butylaminosulfonyl-2-benzyloxypyridine having a melting point of from 121° to 122° C.

(3) 800 mg of metal sodium was added to 150 ml of ethanol, and the mixture was stirred at room temperature in a nitrogen atmosphere. After the metal sodium completely dissolved, 5 g of 4-chloro-3-tert-butylaminosulfonyl-2-benzyloxypyridine was added under cooling, and the mixture was reacted for 3 hours under refluxing.

After completion of the reaction, the reaction mixture was left to cool, put into water and acidified with hydrochloric acid. Then, it was extracted with ethyl acetate, and the extract layer was dried over anhydrous sodium sulfate, whereupon ethyl acetate was distilled off under reduced pressure. The obtained crystals were washed with a solvent mixture of n-hexane and ethyl acetate to obtain 4 g of 4-ethoxy-3-tert-butylaminosulfonyl-2-benzyloxypyridine having a melting point of from 112° to 114° C.

(4) To 100 ml of methanol, 3 g of 4-ethoxy-3-tert-butylaminosulfonyl-2-benzyloxypyridine and a catalytic amount of palladium chloride were added, and the mixture was reacted in a hydrogen gas atmosphere at room temperature for 5 hours with stirring.

After completion of the reaction, the reaction mixture was filtered, and from the obtained filtrate, the solvent was distilled off under reduced pressure. The obtained crystals were washed with a solvent mixture of n-hexane and ethyl acetate to obtain 2.2 g of 4-ethoxy-3-tert-butylaminosulfonyl-2(1H)-pyridone having a melting point of from 159° to 163° C.

(5) 20 ml of acetonitrile, 600 mg of anhydrous potassium carbonate, 500 mg of 4-ethoxy-3-tert-butylaminosulfonyl-2 (1H)-pyridone and 400 mg of ethyl iodide were mixed and reacted at a temperature of from 80° to 100° C. for 1.5 hours.

After completion of the reaction, water was added to the reaction mixture. Further, the mixture was acidified by an addition of hydrochloric acid and then extracted with ethyl acetate. The extract layer was dried over anhydrous sodium sulfate, and ethyl acetate was distilled off under reduced pressure. The obtained residue was purified by silica gel column chromatography (developing solvent: ethyl acetate/n-hexane=1/1) to obtain 350 mg of 1-ethyl-4-ethoxy-3-tert-butylaminosulfonyl-2(1H)-pyridone having a melting point of from 119° to 121° C.

(6) Using 1-ethyl-4-ethoxy-3-tert-butylaminosulfonyl-2 (1H)-pyridone obtained in the above step (5), 100 mg of the desired product having a melting point of from 168° to 171° C. was prepared in the same manner as in Preparation Example 1(4) and (5).

PREPARATION EXAMPLE 6

Preparation of N-[(4,6-dimethoxypyrimidin-2-yl) aminocarbonyl]-[1-ethyl-4-methylthio-2(1H)-pyridone]-3-sulfonamide (Compound No. 497, as given hereinafter)

(1) 6 g of 3-tert-butylaminosulfonyl-2-benzyloxypyridine was dissolved in 60 ml of tetrahydrofuran, and the solution was cooled to −70° C. in a nitrogen atmosphere. Then, 16 ml of n-butyl lithium was gradually added thereto in a nitrogen atmosphere. Then, the mixture was reacted at the same temperature for 30 minutes with stirring, and 2.3 g of dimethyl disulfide was added thereto. Then, the mixture was reacted with stirring while gradually returning the temperature to room temperature, and the reaction was completed when the temperature returned to room temperature.

After completion of the reaction, the reaction mixture was put into water and extracted with ethyl acetate. The extract layer was dried over anhydrous sodium sulfate, whereupon ethyl acetate was distilled off under reduced pressure. The obtained residue was purified by silica gel column chromatography (developing solvent: n-hexane/ethyl acetate=3/1) to obtain 5.7 g of 4-methylthio-3-tert-butylaminosulfonyl-2-benzyloxypyridine having a melting point of from 130° to 131° C.

(2) 2.5 g of 4-methylthio-3-tert-butylaminosulfonyl-2-benzyloxypyridine was added to 20 ml of diethyl ether and thoroughly dispersed. Then, 10 ml of a 47% boron trifluoride diethyl ether solution was added thereto, and the mixture was reacted at 40° C. for 5 hours with stirring.

After completion of the reaction, the reaction mixture was put into water and extracted with ethyl acetate. The extract layer was dried over anhydrous sodium sulfate, whereupon ethyl acetate was distilled off under reduced pressure.

The obtained crystals were washed with a solvent mixture of n-hexane and ethyl acetate to obtain 1.4 g of 4-methylthio-3-tert-butylaminosulfonyl-2(1H)-pyridone having a melting point of from 235° to 237° C.

(3) 10 ml of acetonitrile, 300 mg of anhydrous potassium carbonate and 300 mg of 4-methylthio-3-tert-butylaminosulfonyl-2(1H)-pyridone were mixed and reacted at a temperature of from 80° to 100° C. for 30 minutes. Then, 240 mg of ethyl iodide was added thereto, and the mixture was reacted at the same temperature for further 30 minutes.

After completion of the reaction, the reaction mixture was put into water, acidified by an addition of hydrochloric acid and then extracted with ethyl acetate. The extract layer was dried over anhydrous sodium sulfate, whereupon ethyl acetate was distilled off under reduced pressure. The obtained residue was purified by silica gel column chromatography (developing solvent: ethyl acetate/n-hexane=1/1) to obtain 210 mg of 1-ethyl-4-methylthio-3-tert-butylaminosulfonyl-2(1H)-pyridone having a melting point of from 207° to 210° C.

(4) Using 1-ethyl-4-methylthio-3-tert-butylaminosulfonyl-2(1H)-pyridone obtained in the above step (3), 100 mg of the desired product having a melting point of from 204° to 205° C. was prepared in the same manner as in Preparation Example 1(4) and (5).

PREPARATION EXAMPLE 7

Preparation of N-[(4,6-dimethoxypyrimidin-2-yl) aminocarbonyl]-[1-(n-propyl)-5-bromo-2(1H)-pyridone]-3-sulfonamide (Compound No. 503, as given hereinafter)

(1) To 30 ml of chloroform, 500 mg of 3-tert-butylaminosulfonyl-2(1H)-pyridone and 426 mg of N-bromosuccinimide were added, and the mixture was reacted for 18 hours under refluxing.

After completion of the reaction, the reaction mixture was left to cool and then filtered. From the obtained filtrate, the solvent was distilled off under reduced pressure to obtain 759 mg of 5-bromo-3-tert-butylaminosulfonyl-2(1H)-pyridone.

(2) 10 ml of acetonitrile, 600 mg of anhydrous potassium carbonate and 754 mg of 5-bromo-3-tert-butylaminosulfonyl-2(1H)-pyridone were mixed and reacted at a temperature of from 80° to 100° C. for 30 minutes. Then, 404 mg of ethyl iodide was added thereto, and the mixture was further reacted at the same temperature for 30 minutes.

After completion of the reaction, the reaction mixture was put into water, acidified by an addition of hydrochloric acid and then extracted with methylene chloride. The extract layer was dried over anhydrous sodium sulfate, whereupon methylene chloride was distilled off under reduced pressure. The obtained residue was purified by silica gel column chromatography to obtain 317 mg of 1-(n-propyl)-5-bromo-3-tert-butylaminosulfonyl-2(1H)-pyridone.

(3) Using 1-(n-propyl)-5-bromo-3-tert-butylaminosulfonyl-2(1H)-pyridone obtained in the above step (2), 280 mg of the desired product having a melting point of from 200° to 210° C. was prepared in the same manner as in Preparation Example 1(4) and (5).

PREPARATION EXAMPLE 8

Preparation of N-[(4-methoxy-6-methyl-1,3,5-triazin-2-yl)aminocarbonyl]-[2-chloro-1-methyl-4 (1H)-pyridone]-3-sulfonamide (Compound No. 676, as given hereinafter)

(1) 16.6 g of benzyl alcohol was dissolved in 160 ml of anhydrous dimethylformamide, and the solution was cooled with ice. Then, 6.16 g of 60% sodium hydride was gradually added thereto at a temperature of not higher than 10° C. After completion of the addition, the mixture was stirred at room temperature for 20 minutes. Then, the mixture was again cooled with ice, and 20.8 g of 2,4-dichloropyridine was gradually added. After completion of the addition, the mixture was reacted at room temperature for 2 hours with stirring.

After completion of the reaction, the reaction mixture was cooled with ice and neutralized with concentrated sulfuric acid. Then, dimethylformamide was distilled off under reduced pressure, and water was added to the residue, followed by extraction with dichloromethane. The extract solution was washed with a saline solution and dried over anhydrous sodium sulfate. Then, dichloromethane was distilled off to obtain 24.4 g of 4-benzyloxy-2-chloropyridine as yellow crystals.

(2) In a nitrogen atmosphere, 90 ml of a dry tetrahydrofuran solution containing 10 g of 4-benzyloxy-2-chloropyridine was cooled to −73° C. by means of dry ice-acetone. Then, 37 ml of a 1.7M butyl lithium hexane solution was dropwise added at a temperature of not higher than −66° C. After completion of the dropwise addition, the mixture was reacted at the same temperature for 15 minutes with stirring. Then, 4.1 g of sulfur powder was added thereto, and the mixture was stirred at the same temperature for further 10 minutes, then gradually returned to room temperature and further reacted for 1.2 hours with stirring.

After completion of the reaction, ice was added to the reaction mixture, and the mixture was acidified with concentrated hydrochloric acid and then extracted with dichloromethane to obtain an extract solution containing 4-benzyloxy-2-chloro-3-pyridinethiol.

To the obtained extract solution, 90 ml of 50% acetic acid was added. Then, while blowing chlorine gas thereto at a temperature of 5° C., the reaction was carried out. The reaction was terminated when excess chlorine gas started to accumulate.

After completion of the reaction, ice was added to the reaction mixture, followed by extraction with dichloromethane. The extract was washed twice with ice water and then dried over anhydrous sodium sulfate to obtain an extract solution containing 4-benzyloxy-2-chloro-3-chlorosulfonylpyridine.

The obtained extract solution was cooled with ice, and 20 ml of tert-butylamine was dropwise added thereto at a temperature of not higher than 15° C. Then, the mixture was returned to room temperature and further reacted for 30 minutes with stirring.

After completion of the reaction, water was added to the reaction mixture, followed by extraction with dichloromethane. The extract washed with a saline solution and dried over anhydrous sodium sulfate, whereupon dichloromethane was distilled off under reduced pressure. The obtained residue was purified by silica gel column chromatography (developing solvent: ethyl acetate/n-hexane=2/3) to obtain 0.89 g of 4-benzyloxy-2-chloro-3-tert-butylaminosulfonylpyridine.

(3) 10 mg of 10% palladium carbon was added to 20 ml of an ethanol solution containing 0.86 g of 4-benzyloxy-2-chloro-3-tert-butylaminosulfonylpyridine, and the mixture was reacted for 3.5 hours at 50° C. in a hydrogen gas atmosphere.

After completion of the reaction, palladium carbon was filtered off, and the obtained filtrate was distilled under reduced pressure to obtain 0.77 g of 2-chloro-3-tert-butylaminosulfonyl-4(1H)-pyridone.

(4) Into an autoclave, 0.32 g of 2-chloro-3-tert-butylaminosulfonyl-4(1H)-pyridone, 6 ml of acetonitrile, 0.36 g of potassium carbonate and 0.37 g of iodomethane were charged and reacted at 90° C. for 1.5 hours.

After completion of the reaction, the reaction mixture was concentrated under reduced pressure, and water was added thereto, followed by extraction with ethyl acetate. The extract was washed with a saline solution and then dried over anhydrous sodium sulfate, whereupon ethyl acetate was distilled off under reduced pressure. To the obtained residue, diethyl ether was added, followed by rubbing with a spatula for crystallization to obtain 0.23 g of 2-chloro-1-methyl-3-tert-butylaminosulfonyl-4(1H)-pyridone as white crystals.

(5) 1.0 g of trifluoroacetic acid was added to 0.23 g of 2-chloro-1-methyl-3-tert-butylaminosulfonyl-4(1H)-pyridone, and the mixture was reacted at a temperature of from 60° to 70° C. overnight.

After completion of the reaction, trifluoroacetic acid was distilled off under reduced pressure. To the obtained residue, diethyl ether was added, followed by rubbing with a spatula for crystallization to obtain 0.149 g of 2-chloro-1-methyl-3-aminosulfonyl-4(1H)-pyridone (Intermediate No. 517, as given hereinafter) having a melting point of from 185° to 197° C.

(6) Using 2-chloro-1-methyl-3-aminosulfonyl-4(1H)-pyridone obtained in the above step (5), 0.163 g of the desired product having a melting point of from 140° to 147° C. was prepared in the same manner as in Preparation Example 3(5).

Now, typical examples of the pyridone compound of the formula (II-1) of the present invention and typical examples of the pyridonesulfonylurea compound of the formula (I) of the present invention, which can be prepared in accordance with the above Preparation Examples or by various methods for producing the compounds of the present invention, as described above, will be given in Tables 1 to 14, respectively.

TABLE 1

$Q-SO_2NH_2$ (II-1)

| Intermediate No. | Pyridone ring | $R_1$ | Physical properties (m.p.: °C.) |
|---|---|---|---|
| 1 | (pyridone structure A) | H | 269–271 |
| 2 | " | $CH_3$ | |
| 3 | " | $C_2H_5$ | |
| 4 | " | n-$C_3H_7$ | 140–142 |
| 5 | " | iso-$C_3H_7$ | 153–155 |
| 6 | " | n-$C_4H_9$ | 145–146 |
| 7 | " | sec-$C_4H_9$ | |
| 8 | " | tert-$C_4H_9$ | |
| 9 | " | n-$C_5H_{11}$ | |
| 10 | " | n-$C_6H_{13}$ | |
| 11 | " | $-CH_2Cl$ | |
| 12 | " | $-CHCl_2$ | |
| 13 | " | $-CH_2CH_2Cl$ | |
| 14 | " | $-(CH_2)_3Cl$ | |
| 15 | " | $-CH(Cl)CH_3$ | |
| 16 | " | $-CH_2CH(Cl)CH_3$ | |
| 17 | " | $-CH(CH_2CHl)_2$ | |
| 18 | " | $-CH_2F$ | |
| 19 | (pyridone structure B) | $-CHF_2$ | |
| 20 | " | $-CF_3$ | |
| 21 | " | $-(CH_2)_3F$ | |
| 22 | " | $-CH_2OCH_3$ | |
| 23 | " | $-CH_2OCH_2CH_3$ | |
| 24 | " | $-CH_2OCH(CH_3)_2$ | 129–131 |
| 25 | " | $-(CH_2)_2OCH_3$ | |
| 26 | " | $-CH_2SCH_3$ | |
| 27 | " | $(-CH_2)_2SCH_3$ | |
| 28 | " | $-CH_2COCH_3$ | |
| 29 | " | $-CH_2CO_2CH_3$ | |
| 30 | " | $-CH_2SOCH_3$ | |
| 31 | " | $-CH_2SO_2CH_3$ | |
| 32 | " | $-CH_2-$(phenyl) | |
| 33 | " | $-CH_2-$(2,4-dichlorophenyl) | |
| 34 | " | $-CH_2-$(4-methylphenyl) | |
| 35 | (pyridone structure C) | $-CH_2OCH_2-$(phenyl) | |

TABLE 1-continued

Q—SO₂NH₂ (II-1)

| Intermediate No. | Pyridone ring | R₁ | Physical properties (m.p.: °C.) |
|---|---|---|---|
| 36 | " | —CH₂NHCH₃ | |
| 37 | " | —CH₂N(CH₃)₂ | |
| 38 | " | —CH₂CH₂CN | |
| 39 | " | —CH₂CH₂NO₂ | |
| 40 | " | —CH=CH₂ | |
| 41 | " | —CH₂CH=CH₂ | |
| 42 | " | —CH₂CH=CHCH₃ | |
| 43 | " | —CH₂C(CH₃)=CH₂ | |
| 44 | " | —CH₂CH=CCl₂ | |
| 45 | " | —CH₂CH=CF₂ | |
| 46 | " | —C≡CH | |
| 47 | " | —CH₂C≡CH | |
| 48 | " | —OCH₂CH₃ | 127–129 |
| 49 | " | —OCH₂CH₂Cl | |
| 50 | " | —SCH₃ | |
| 51 | " | —SCHF₂ | |
| 52 | " | —COCH₃ | |
| 53 | " | —COCH₂CH₂Cl | |
| 54 | 3-methyl pyridone | —CO₂CH₃ | |
| 55 | " | —CO₂CH₂CH₂Cl | |
| 56 | " | —SOCH₃ | |
| 57 | " | —SOCHF₂ | |
| 58 | " | —SO₂CH₃ | |
| 59 | " | —SO₂(CH₂)₃F | |
| 60 | " | —NH₂ | |
| 61 | " | —NHCH₃ | |
| 62 | " | —N(CH₃)₂ | |
| 63 | " | —NHSOCH₃ | |
| 64 | " | —N(CH₃)—SO₂CH₃ | |
| 65 | " | —N(C₂H₅)—SO₂CH(CH₃)₂ | |
| 66 | " | —N(CH₃)—COC₂H₅ | |
| 67 | " | —CONH₂ | |
| 68 | " | —CONHCH₃ | |
| 69 | " | —CON(CH₃)₂ | |
| 70 | " | —SO₂NHCH₃ | |
| 71 | " | —SO₂N(CH₃)₂ | |
| 72 | 3-methyl pyridone | —SO₂N(CH₃)—COCH₃ | |
| 73 | " | —SO₂N(C₂H₅)—CO₂CH₃ | |
| 74 | 4-methyl pyridone | H | |
| 75 | " | CH₃ | |
| 76 | " | C₂H₅ | |
| 77 | " | n-C₃H₇ | |
| 78 | " | iso-C₃H₇ | |
| 79 | " | n-C₄H₉ | |
| 80 | " | sec-C₄H₉ | |
| 81 | " | tert-C₄H₉ | |
| 82 | " | n-C₅H₁₁ | |
| 83 | " | n-C₆H₁₃ | |
| 84 | " | —CH₂Cl | |
| 85 | " | —CHCl₂ | |
| 86 | " | —CH₂CH₂Cl | |
| 87 | " | —(CH₂)₃Cl | |
| 88 | " | —CH(Cl)CH₃ | |
| 89 | 4-methyl pyridone | —CH₂CH(Cl)CH₃ | |
| 90 | " | —CH₂F | |
| 91 | " | —CHF₂ | |
| 92 | " | —CF₃ | |
| 93 | " | —(CH₂)₃F | |
| 94 | " | —CH₂OCH₃ | |
| 95 | " | —CH₂OCH₂CH₃ | |
| 96 | " | —(CH₂)₂OCH₃ | |
| 97 | " | —CH₂SCH₃ | |
| 98 | " | —(CH₂)₂SCH₃ | |
| 99 | " | —CH₂COCH₃ | |
| 100 | " | —CH₂CO₂CH₃ | |
| 101 | " | —CH₂SOCH₃ | |
| 102 | " | —CH₂SO₂CH₃ | |
| 103 | " | —CH₂—C₆H₅ | |
| 104 | " | —CH₂NHCH₃ | |
| 105 | " | —CH₂N(CH₃)₂ | |
| 106 | " | —CH₂CH₂CN | |
| 107 | " | —CH=CH₂ | |
| 108 | 4-methyl pyridone | —CH₂CH=CH₂ | |
| 109 | " | —CH₂C(CH₃)=CH₂ | |
| 110 | " | —CH₂CH=CCl₂ | |
| 111 | " | —CH₂CH=CF₂ | |

TABLE 1-continued

Q—SO$_2$NH$_2$ (II-1)

| Intermediate No. | Pyridone ring | R$_1$ | Physical properties (m.p.: °C.) |
|---|---|---|---|
| 112 | " | —C≡CH | |
| 113 | " | —CH$_2$C≡CH | |
| 114 | " | —OCH$_2$CH$_3$ | |
| 115 | " | —SCH$_3$ | |
| 116 | " | —COCH$_3$ | |
| 117 | " | —CO$_2$CH$_3$ | |
| 118 | " | —CH$_2$CO$_2$CH$_3$ | |
| 119 | " | —SOCH$_3$ | |
| 120 | " | —SO$_2$CH$_3$ | |
| 121 | " | —NH$_2$ | |
| 122 | " | —NHCH$_3$ | |
| 123 | " | —N(CH$_3$)$_2$ | |
| 124 | " | —NHSOCH$_3$ | |
| 125 | " | —N(—SO$_2$CH$_3$)CH$_3$ | |
| 126 | 4-methyl-pyridone | —N(—COC$_2$H$_5$)CH$_3$ | |
| 127 | " | —CONH$_2$ | |
| 128 | " | —CONHCH$_3$ | |
| 129 | " | —CON(CH$_3$)$_2$ | |
| 130 | " | —SO$_2$NHCH$_3$ | |
| 131 | " | —SO$_2$N(CH$_3$)$_2$ | |
| 132 | " | —SO$_2$N(—COCH$_3$)CH$_3$ | |
| 133 | " | —SO$_2$N(—CO$_2$CH$_3$)C$_2$H$_5$ | |
| 134 | 5-methyl-pyridone | H | |
| 135 | " | CH$_3$ | |
| 136 | " | C$_2$H$_5$ | |
| 137 | " | n-C$_3$H$_7$ | |
| 138 | " | iso-C$_3$H$_7$ | |
| 139 | " | n-C$_4$H$_9$ | |
| 140 | " | sec-C$_4$H$_9$ | |
| 141 | " | tert-C$_4$H$_9$ | |
| 142 | 5-methyl-pyridone | n-C$_5$H$_{11}$ | |
| 143 | " | n-C$_6$H$_{13}$ | |
| 144 | " | —CH$_2$Cl | |
| 145 | " | —CHCl$_2$ | |
| 146 | " | —CH$_2$CH$_2$Cl | |
| 147 | " | —(CH$_2$)$_3$Cl | |
| 148 | " | —CH(Cl)CH$_3$ | |
| 149 | " | —CH$_2$CH(Cl)CH$_3$ | |
| 150 | " | —CH$_2$F | |
| 151 | " | —CHF$_2$ | |
| 152 | " | —CF$_3$ | |
| 153 | " | —(CH$_2$)$_3$F | |
| 154 | " | —CH$_2$OCH$_3$ | |
| 155 | " | —CH$_2$OCH$_2$CH$_3$ | |
| 156 | " | —(CH$_2$)$_2$OCH$_3$ | |
| 157 | " | —CH$_2$SCH$_3$ | |
| 158 | " | (—CH$_2$)$_2$SCH$_3$ | |
| 159 | " | —CH$_2$COCH$_3$ | |
| 160 | " | —CH$_2$CO$_2$CH$_3$ | |
| 161 | " | —CH$_2$SOCH$_3$ | |
| 162 | 5-methyl-pyridone | —CH$_2$SO$_2$CH$_3$ | |
| 163 | " | —CH$_2$—C$_6$H$_5$ | |
| 164 | " | —CH$_2$NHCH$_3$ | |
| 165 | " | —CH$_2$N(CH$_3$)$_2$ | |
| 166 | " | —CH$_2$CH$_2$CN | |
| 167 | " | —CH=CH$_2$ | |
| 168 | " | —CH$_2$CH=CH$_2$ | |
| 169 | " | —CH$_2$C(=CH$_2$)CH$_3$ | |
| 170 | " | —CH$_2$CH=CCl$_2$ | |
| 171 | " | —CH$_2$CH=CF$_2$ | |
| 172 | " | —C≡CH | |
| 173 | " | —CH$_2$C≡CH | |
| 174 | " | —OCH$_2$CH$_3$ | |
| 175 | " | —SCH$_3$ | |
| 176 | " | —COCH$_3$ | |
| 177 | " | —CO$_2$CH$_3$ | |
| 178 | " | —CH$_2$CO$_2$CH$_3$ | |
| 179 | " | —SOCH$_3$ | |
| 180 | 5-methyl-pyridone | —SO$_2$CH$_3$ | |
| 181 | " | —NH$_2$ | |
| 182 | " | —NHCH$_3$ | |
| 183 | " | —N(CH$_3$)$_2$ | |
| 184 | " | —NHSOCH$_3$ | |
| 185 | " | —N(—SO$_2$CH$_3$)CH$_3$ | |
| 186 | " | —N(—COC$_2$H$_5$)CH$_3$ | |
| 187 | " | —CONH$_2$ | |
| 188 | " | —CONHCH$_3$ | |
| 189 | " | —CON(CH$_3$)$_2$ | |

TABLE 1-continued

Q—SO₂NH₂ (II-1)

| Intermediate No. | Pyridone ring | R₁ | Physical properties (m.p.: °C.) |
|---|---|---|---|
| 190 | " | —SO₂NHCH₃ | |
| 191 | " | —SO₂N(CH₃)₂ | |
| 192 | " | —SO₂N(CH₃)—COCH₃ | |
| 193 | " | —SO₂N(C₂H₅)—CO₂CH₃ | |
| 194 | 6-methyl-2-pyridone, N-R₁ | H | |
| 195 | " | CH₃ | 177–178 |
| 196 | " | C₂H₅ | |
| 197 | " | —CH₂F | |
| 198 | " | —CHF₂ | |
| 199 | " | —CF₃ | |
| 200 | " | —(CH₂)₂F | |
| 201 | " | —OCH₂CH₃ | |
| 202 | " | —SCH₃ | |
| 203 | " | —NH₂ | |
| 204 | " | —NHCH₃ | |
| 205 | 3-methyl-4-pyridone, N-R₁ | H | 273–277 |
| 206 | " | CH₃ | 216 (decomposed) |
| 207 | " | C₂H₅ | 175–186 |
| 208 | " | n-C₃H₇ | 111–115 |
| 209 | " | iso-C₃H₇ | 89–120 |
| 210 | " | n-C₄H₉ | 103–105 |
| 211 | 3-methyl-4-pyridone, N-R₁ | sec-C₄H₉ | |
| 212 | " | tert-C₄H₉ | |
| 213 | " | n-C₅H₁₁ | |
| 214 | " | n-C₆H₁₃ | |
| 215 | " | —CH₂Cl | |
| 216 | " | —CHCl₂ | |
| 217 | " | —CH₂CH₂Cl | 57–155 |
| 218 | " | —(CH₂)₃Cl | |
| 219 | " | —CH(Cl)CH₃ | |
| 220 | " | —CH₂CH(Cl)CH₃ | |
| 221 | " | —CH₂F | |
| 222 | " | —CHF₂ | 169–205 |
| 223 | " | —CF₃ | |
| 224 | " | —(CH₂)₂F | 180–190 |
| 225 | " | —(CH₂)₃F | |
| 226 | " | —CH₂OCH₃ | 110–113 |
| 227 | " | —CH₂OCH₂CH₃ | |
| 228 | " | —(CH₂)₂OCH₃ | |
| 229 | " | —CH₂SCH₃ | |
| 230 | " | —(CH₂)₂SCH₃ | |
| 231 | 3-methyl-4-pyridone, N-R₁ | —CH₂COCH₃ | |
| 232 | " | —CH₂CO₂CH₃ | 135–156 |
| 233 | " | —CH₂SOCH₃ | |
| 234 | " | —CH₂SO₂CH₃ | |
| 235 | " | —CH₂—C₆H₅ | 125–134 |
| 236 | " | —CH₂NHCH₃ | |
| 237 | " | —CH₂N(CH₃)₂ | |
| 238 | " | —CH₂CH₂CN | |
| 239 | " | —CH=CH₂ | |
| 240 | " | —CH₂CH=CH₂ | |
| 241 | " | —CH₂C(CH₃)=CH₂ | |
| 242 | " | —CH₂CH=CCl₂ | |
| 243 | " | —CH₂CH=CF₂ | |
| 244 | " | —C≡CH | |
| 245 | " | —CH₂C≡CH | |
| 246 | " | —COCH₃ | |
| 247 | " | —CO₂CH₃ | 220–239 |
| 248 | " | —CH₂CO₂CH₃ | |
| 249 | 3-methyl-4-pyridone, N-R₁ | —SOCH₃ | |
| 250 | " | —SO₂CH₃ | |
| 251 | " | —NH₂ | |
| 252 | " | —NHCH₃ | |
| 253 | " | —N(CH₃)₂ | |
| 254 | " | —NHSOCH₃ | |
| 255 | " | —N(CH₃)—SO₂CH₃ | |
| 256 | " | —N(CH₃)—COC₂H₅ | |
| 257 | " | —CONH₂ | |
| 258 | " | —CONHCH₃ | |
| 259 | " | —CON(CH₃)₂ | 185–197 |
| 260 | " | —SO₂NHCH₃ | |
| 261 | " | —SO₂N(CH₃)₂ | |

TABLE 1-continued

Q—SO$_2$NH$_2$ (II-1)

| Intermediate No. | Q Pyridone ring | R$_1$ | Physical properties (m.p.: °C.) |
|---|---|---|---|
| 262 | " | —SO$_2$N(CH$_3$)—COCH$_3$ | |
| 263 | " | —SO$_2$N(C$_2$H$_5$)—CO$_2$CH$_3$ | |
| 264 | 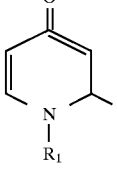 | H | |
| 265 | " | CH$_3$ | |
| 266 | " | C$_2$H$_5$ | |
| 267 | " | n-C$_3$H$_7$ | |
| 268 | " | iso-C$_3$H$_7$ | |
| 269 | " | n-C$_4$H$_9$ | |
| 270 | " | sec-C$_4$H$_9$ | |
| 271 | " | tert-C$_4$H$_9$ | |
| 272 | " | n-C$_5$H$_{11}$ | |
| 273 | " | n-C$_6$H$_{13}$ | |
| 274 | " | —CH$_2$Cl | |
| 275 | " | —CHCl$_2$ | |
| 276 | " | —CH$_2$CH$_2$Cl | |
| 277 | " | —(CH$_2$)$_3$Cl | |
| 278 | " | —CH(Cl)CH$_3$ | |
| 279 | " | —CH$_2$CH(Cl)CH$_3$ | |
| 280 | " | —CH$_2$F | |
| 281 | " | —CHF$_2$ | |
| 282 | " | —CF$_3$ | |
| 283 | " | —(CH$_2$)$_3$F | |
| 284 | 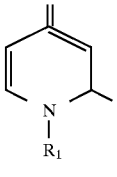 | —CH$_2$OCH$_3$ | |
| 285 | " | —CH$_2$OCH$_2$CH$_3$ | |
| 286 | " | —(CH$_2$)$_2$OCH$_3$ | |
| 287 | " | —CH$_2$SCH$_3$ | |
| 288 | " | —(CH$_2$)$_2$SCH$_3$ | |
| 289 | " | —CH$_2$COCH$_3$ | |
| 290 | " | —CH$_2$CO$_2$CH$_3$ | |
| 291 | " | —CH$_2$SOCH$_3$ | |
| 292 | " | —CH$_2$SO$_2$CH$_3$ | |
| 293 | " | —CH$_2$—C$_6$H$_5$ | |
| 294 | " | —CH$_2$NHCH$_3$ | |
| 295 | " | —CH$_2$N(CH$_3$)$_2$ | |
| 296 | " | —CH$_2$CH$_2$CN | |
| 297 | " | —CH=CH$_2$ | |
| 298 | " | —CH$_2$CH=CH$_2$ | |
| 299 | " | —CH$_2$C(CH$_3$)=CH$_2$ | |
| 300 | " | —CH$_2$CH=CCl$_2$ | |
| 301 | " | —CH$_2$CH=CF$_2$ | |
| 302 | 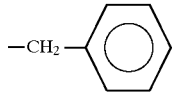 | —C≡CH | |
| 303 | " | —CH$_2$C≡CH | |
| 304 | " | —COCH$_3$ | |
| 305 | " | —CO$_2$CH$_3$ | |
| 306 | " | —CH$_2$CO$_2$CH$_3$ | |
| 307 | " | —SOCH$_3$ | |
| 308 | " | —SO$_2$CH$_3$ | |
| 309 | " | —NH$_2$ | |
| 310 | " | —NHCH$_3$ | |
| 311 | " | —N(CH$_3$)$_2$ | |
| 312 | " | —NHSOCH$_3$ | |
| 313 | " | —N(CH$_3$)—SO$_2$CH$_3$ | |
| 314 | " | —N(CH$_3$)—COC$_2$H$_5$ | |
| 315 | " | —CONH$_2$ | |
| 316 | " | —CONHCH$_3$ | |
| 317 | " | —CON(CH$_3$)$_2$ | |
| 318 | " | —SO$_2$NHCH$_3$ | |
| 319 | " | —SO$_2$N(CH$_3$)$_2$ | |
| 320 | 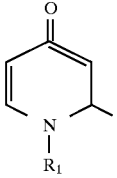 | —SO$_2$N(CH$_3$)—COCH$_3$ | |
| 321 | " | —SO$_2$N(C$_2$H$_5$)—CO$_2$CH$_3$ | |

TABLE 2

Q = 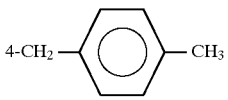

| Intermediate No. | $(G)_n$ | $R_1$ | Physical properties (m.p.: °C.) |
|---|---|---|---|
| 322 | 4-Cl | H | |
| 323 | 5-CH$_3$ | H | |
| 324 | 6-OCH$_2$CH$_3$ | H | |
| 325 | 4-CON(CH$_3$)$_2$ | H | |
| 326 | 5-Br | CH$_3$ | |
| 327 | 4-C$_2$H$_5$ | CH$_3$ | |
| 328 | 6-CF$_3$ | CH$_3$ | |
| 329 | 5-CH$_2$OCH$_2$CH$_3$ | CH$_3$ | |
| 330 | 4-CH$_2$COCH$_3$ | CH$_3$ | |
| 331 | 4-OCH$_3$ | CH$_3$ | |
| 332 | 4-OCH$_2$CH$_3$ | CH$_3$ | |
| 333 | 4-SCH$_3$ | CH$_3$ | |
| 334 | 5-SO$_2$CH$_3$ | CH$_3$ | |
| 335 | 6-Cl | C$_2$H$_5$ | |
| 336 | 6-CH$_3$ | C$_2$H$_5$ | |
| 337 | 4-CH$_2$CO$_2$CH$_3$ | C$_2$H$_5$ | |
| 338 | 4-CH$_2$SO$_2$CH$_3$ | C$_2$H$_5$ | |
| 339 | 4-CH$_2$—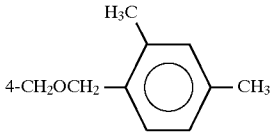—CH$_3$ | C$_2$H$_5$ | |
| 340 | 4-CH$_2$OCH$_2$—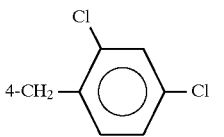—CH$_3$ (H$_3$C) | C$_2$H$_5$ | |
| 341 | 4-OCH$_3$ | C$_2$H$_5$ | 166–169 |
| 342 | 4-OCH$_2$CH$_3$ | C$_2$H$_5$ | 166–167 |
| 343 | 4-SCH$_3$ | C$_2$H$_5$ | 209–211 |
| 344 | 4-N(CH$_3$)$_2$ | C$_2$H$_5$ | |
| 345 | 4-N—SO$_2$CH$_3$ \| CH$_3$ | C$_2$H$_5$ | |
| 346 | 4-CON(CH$_3$)$_2$ | C$_2$H$_5$ | |
| 347 | 4-SO$_2$N(CH$_3$)$_2$ | C$_2$H$_5$ | |
| 348 | 5-Cl | n-C$_3$H$_7$ | |
| 349 | 5-Br | n-C$_3$H$_7$ | |
| 350 | 4,6-F$_2$ | n-C$_3$H$_7$ | |
| 351 | 4-CH$_3$ | n-C$_3$H$_7$ | |
| 352 | 4-C$_3$H$_7$(n) | n-C$_3$H$_7$ | |
| 353 | 4,6-(CH$_3$)$_2$ | n-C$_3$H$_7$ | |
| 354 | 4-CF$_3$ | n-C$_3$H$_7$ | |
| 355 | 5-CF$_3$ | n-C$_3$H$_7$ | |
| 356 | 4-CH$_2$OCH$_3$ | n-C$_3$H$_7$ | |
| 357 | 4-CH$_2$SCH$_3$ | n-C$_3$H$_7$ | |
| 358 | 4-CH$_2$CO$_2$CH$_3$ | n-C$_3$H$_7$ | |
| 359 | 4-CH$_2$SO$_2$CH$_3$ | n-C$_3$H$_7$ | |
| 360 | 4-CH$_2$—(2,4-Cl$_2$-phenyl) | n-C$_3$H$_7$ | |
| 361 | 4-CH$_2$N(CH$_3$)$_2$ | n-C$_3$H$_7$ | |
| 362 | 4-OCH$_3$ | n-C$_3$H$_7$ | 186–190 (decomposed) |
| 363 | 4-OCH$_2$CH$_3$ | n-C$_3$H$_7$ | 169–171 |
| 364 | 4-OCH$_2$CH$_2$CH$_3$ | n-C$_3$H$_7$ | 107–110 (decomposed) |

TABLE 2-continued

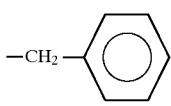

| Intermediate No. | (G)$_n$ | R$_1$ | Physical properties (m.p.: °C.) |
|---|---|---|---|
| 365 | 4-OCH(CH$_3$)$_2$ | n-C$_3$H$_7$ | |
| 366 | 4-OCH$_2$CH$_2$F | n-C$_3$H$_7$ | |
| 367 | 4-OCH$_2$CHF$_2$ | n-C$_3$H$_7$ | |
| 368 | 4-OCH$_2$CF$_3$ | n-C$_3$H$_7$ | 161–163 (decomposed) |
| 369 | 4-SCH$_3$ | n-C$_3$H$_7$ | |
| 370 | 4-SCH$_2$CH$_3$ | n-C$_3$H$_7$ | 152–155 |
| 371 | 4-CO$_2$CH$_3$ | n-C$_3$H$_7$ | |
| 372 | 4-SO$_2$CH$_3$ | n-C$_3$H$_7$ | |
| 373 | 4-NHCH$_3$ | n-C$_3$H$_7$ | |
| 374 | 4-N(CH$_3$)—SO$_2$CH$_3$ | n-C$_3$H$_7$ | |
| 375 | 4-N(CH$_3$)—COC$_2$H$_5$ | n-C$_3$H$_7$ | |
| 376 | 4-CON(CH$_3$)$_2$ | n-C$_3$H$_7$ | |
| 377 | 4-SO$_2$N(CH$_3$)$_2$ | n-C$_3$H$_7$ | |
| 378 | 4-SO$_2$N(C$_2$H$_5$)—CO$_2$CH$_3$ | n-C$_3$H$_7$ | |
| 379 | 5-Cl | iso-C$_3$H$_7$ | |
| 380 | 4-CH$_3$ | iso-C$_3$H$_7$ | |
| 381 | 4-OCH$_3$ | iso-C$_3$H$_7$ | |
| 382 | 4-OCH$_2$CH$_3$ | iso-C$_3$H$_7$ | |
| 383 | 4-SCH$_3$ | iso-C$_3$H$_7$ | 210–212 |
| 384 | 5-Br | —CH$_2$CH$_2$Cl | |
| 385 | 4-CH$_3$ | —CF$_3$ | |
| 386 | 5-Br | —CH$_2$OCH$_3$ | |
| 387 | 4-OCH$_3$ | —CH$_2$OCH$_3$ | |
| 388 | 4-OCH$_2$CH$_3$ | —CH$_2$OCH$_3$ | |
| 389 | 4-SCH$_3$ | —CH$_2$OCH$_3$ | |
| 390 | 4-CO$_2$CH$_3$ | —CH$_2$OCH$_3$ | |
| 391 | 4-SO$_2$CH$_3$ | —CH$_2$OCH$_3$ | |
| 392 | 4-NHCH$_3$ | —CH$_2$OCH$_3$ | |
| 393 | 4-N(CH$_3$)—SO$_2$CH$_3$ | —CH$_2$OCH$_3$ | |
| 394 | 4-N(CH$_3$)—COC$_2$H$_5$ | —CH$_2$OCH$_3$ | |
| 395 | 4-CON(CH$_3$)$_2$ | —CH$_2$OCH$_3$ | |
| 396 | 4-SO$_2$N(CH$_3$)$_2$ | —CH$_2$OCH$_3$ | |
| 397 | 4-OCH$_2$CH$_3$ | —CH$_2$SCH$_3$ | |
| 398 | 4-SCH$_3$ | —CH$_2$CO$_2$CH$_3$ | |
| 399 | 4-NHCH$_3$ | —CH$_2$SO$_2$CH$_3$ | |
| 400 | 4-CON(CH$_3$)$_2$ | —CH$_2$—C$_6$H$_5$ | |
| 401 | 4-OCH$_3$ | —CH$_2$N(CH$_3$)$_2$ | |
| 402 | 4-OCH$_3$ | —CH$_2$CH=CH$_2$ | |
| 403 | 4-OCH$_2$CH$_3$ | —CH$_2$CH=CH$_2$ | 147–150 |
| 404 | 4-SCH$_3$ | —CH$_2$CH=CH$_2$ | |
| 405 | 4-CON(CH$_3$)$_2$ | —CH$_2$CH=CH$_2$ | |
| 406 | 4-OCH$_3$ | —OCH$_2$CH$_3$ | |
| 407 | 4-OCH$_2$CH$_3$ | —CO$_2$CH$_3$ | |
| 408 | 4-OCH$_3$ | —SO$_2$CH$_3$ | |

TABLE 2-continued

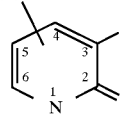

| Intermediate No. | (G)$_n$ | R$_1$ | Physical properties (m.p.: °C.) |
|---|---|---|---|
| 409 | 4-OCH$_3$ | —N(CH$_3$)$_2$ | |
| 410 | 4-OCH$_2$CH$_3$ | —N(CH$_3$)—SO$_2$CH$_3$ | |
| 411 | 4-OCH$_3$ | —CON(CH$_3$)$_2$ | |
| 412 | 4-OCH$_2$CH$_3$ | —SO$_2$N(CH$_3$)$_2$ | |
| 413 | 4-OCH$_2$CH$_3$ | —SO$_2$N(C$_2$H$_5$)—CO$_2$CH$_3$ | |

TABLE 3

| Intermediate No. | (G)$_n$ | R$_1$ | Physical properties (m.p.: °C.) |
|---|---|---|---|
| 414 | 5-Cl | H | |
| 415 | 5-C$_2$H$_5$ | CH$_3$ | |
| 416 | 3-OCH$_3$ | CH$_3$ | |
| 417 | 3-SCH$_3$ | CH$_3$ | |
| 418 | 6-CH$_2$CO$_2$CH$_3$ | C$_2$H$_5$ | |
| 419 | 6-CH$_2$SO$_2$CH$_3$ | C$_2$H$_5$ | |
| 420 | 5,6-F$_2$ | n-C$_3$H$_7$ | |
| 421 | 5-CF$_3$ | n-C$_3$H$_7$ | |
| 422 | 5-CH$_2$OCH$_3$ | n-C$_3$H$_7$ | |
| 423 | 5-CH$_2$SCH$_3$ | n-C$_3$H$_7$ | |
| 424 | 5-CH$_2$—C$_6$H$_5$ | n-C$_3$H$_7$ | |
| 425 | 5-CH$_2$N(CH$_3$)$_2$ | n-C$_3$H$_7$ | |
| 426 | 5-SO$_2$CH$_3$ | n-C$_3$H$_7$ | |
| 427 | 5-NHCH$_3$ | n-C$_3$H$_7$ | |
| 428 | 5-CON(CH$_3$)$_2$ | n-C$_3$H$_7$ | |
| 429 | 5-OCH$_3$ | iso-C$_3$H$_7$ | |
| 430 | 5-Br | —CH$_2$CH$_2$Cl | |
| 431 | 5-Br | —CH$_2$OCH$_3$ | |
| 432 | 5-CO$_2$CH$_3$ | —CH$_2$OCH$_3$ | |
| 433 | 5-N(CH$_3$)—SO$_2$CH$_3$ | —CH$_2$OCH$_3$ | |
| 434 | 5-N(CH$_3$)—COC$_2$H$_5$ | —CH$_2$OCH$_3$ | |
| 435 | 6-SO$_2$N(CH$_3$)$_2$ | —CH$_2$OCH$_3$ | |
| 436 | 6-OCH$_2$CH$_3$ | —CH$_2$SCH$_3$ | |
| 437 | 5-SCH$_3$ | —CH$_2$CO$_2$CH$_3$ | |
| 438 | 5-NHCH$_3$ | —CH$_2$SO$_2$CH$_3$ | |

TABLE 3-continued

| Intermediate No. | (G)$_n$ | R$_1$ | Physical properties (m.p.: °C.) |
|---|---|---|---|
| 439 | 5-CON(CH$_3$)$_2$ | —CH$_2$—C$_6$H$_5$ | |
| 440 | 5-OCH$_3$ | —CH$_2$N(CH$_3$)$_2$ | |
| 441 | 5-OCH$_3$ | —CH$_2$CH═CH$_2$ | |
| 442 | 5-OCH$_3$ | —OCH$_2$CH$_3$ | |
| 443 | 5-OCH$_2$CH$_3$ | —CO$_2$CH$_3$ | |
| 444 | 5-OCH$_3$ | —SO$_2$CH$_3$ | |
| 445 | 5-OCH$_3$ | —N(CH$_3$)$_2$ | |
| 446 | 5-OCH$_3$ | —CON(CH$_3$)$_2$ | |
| 447 | 5-OCH$_2$CH$_3$ | —SO$_2$N(CH$_3$)$_2$ | |

TABLE 4

| Intermediate No. | (G)$_n$ | R$_1$ | Physical properties (m.p.: °C.) |
|---|---|---|---|
| 448 | 4-Cl | H | |
| 449 | 4-C$_2$H$_5$ | CH$_3$ | |
| 450 | 4-OCH$_3$ | CH$_3$ | |
| 451 | 4-SCH$_3$ | CH$_3$ | |
| 452 | 4-CH$_2$CO$_2$CH$_3$ | C$_2$H$_5$ | |
| 453 | 4-CH$_2$SO$_2$CH$_3$ | C$_2$H$_5$ | |
| 454 | 4,6-F$_2$ | n-C$_3$H$_7$ | |
| 455 | 3-CF$_3$ | n-C$_3$H$_7$ | |

TABLE 4-continued

Q = 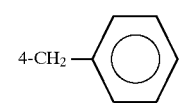

| Intermediate No. | (G)$_n$ | R$_1$ | Physical properties (m.p.: °C.) |
|---|---|---|---|
| 456 | 4-CH$_2$OCH$_3$ | n-C$_3$H$_7$ | |
| 457 | 4-CH$_2$SCH$_3$ | n-C$_3$H$_7$ | |
| 458 | 4-CH$_2$–C$_6$H$_5$ | n-C$_3$H$_7$ | |
| 459 | 4-CH$_2$N(CH$_3$)$_2$ | n-C$_3$H$_7$ | |
| 460 | 4-SO$_2$CH$_3$ | n-C$_3$H$_7$ | |
| 461 | 4-NHCH$_3$ | n-C$_3$H$_7$ | |
| 462 | 4-CON(CH$_3$)$_2$ | n-C$_3$H$_7$ | |
| 463 | 4-OCH$_3$ | iso-C$_3$H$_7$ | |
| 464 | 3-Br | —CH$_2$CH$_2$Cl | |
| 465 | 3-Br | —CH$_2$OCH$_3$ | |
| 466 | 4-CO$_2$CH$_3$ | —CH$_2$OCH$_3$ | |
| 467 | 4-N(CH$_3$)—SO$_2$CH$_3$ | —CH$_2$OCH$_3$ | |
| 468 | 4-N(CH$_3$)—COC$_2$H$_5$ | —CH$_2$OCH$_3$ | |
| 469 | 4-SO$_2$N(CH$_3$)$_2$ | —CH$_2$OCH$_3$ | |
| 470 | 4-OCH$_2$CH$_3$ | —CH$_2$SCH$_3$ | |
| 471 | 4-SCH$_3$ | —CH$_2$CO$_2$CH$_3$ | |
| 472 | 4-NHCH$_3$ | —CH$_2$SO$_2$CH$_3$ | |
| 473 | 4-CON(CH$_3$)$_2$ | —CH$_2$–C$_6$H$_5$ | |
| 474 | 4-OCH$_3$ | —CH$_2$N(CH$_3$)$_2$ | |
| 475 | 4-OCH$_3$ | —CH$_2$CH=CH$_2$ | |
| 476 | 4-OCH$_3$ | —OCH$_2$CH$_3$ | |
| 477 | 4-OCH$_2$CH$_3$ | —CO$_2$CH$_3$ | |
| 478 | 4-OCH$_3$ | —SO$_2$CH$_3$ | |
| 479 | 4-OCH$_3$ | —N(CH$_3$)$_2$ | |
| 480 | 4-OCH$_3$ | —CON(CH$_3$)$_2$ | |
| 481 | 4-OCH$_2$CH$_3$ | —SO$_2$N(CH$_3$)$_2$ | |

TABLE 5

Q = 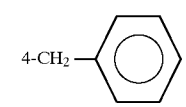

| Intermediate No. | (G)$_n$ | R$_1$ | Physical properties (m.p.: °C.) |
|---|---|---|---|
| 482 | 4-Cl | H | |
| 483 | 4-C$_2$H$_5$ | CH$_3$ | |
| 484 | 4-OCH$_3$ | CH$_3$ | |
| 485 | 4-SCH$_3$ | CH$_3$ | |
| 486 | 4-CH$_2$CO$_2$CH$_3$ | C$_2$H$_5$ | |
| 487 | 4-CH$_2$SO$_2$CH$_3$ | C$_2$H$_5$ | |
| 488 | 4,5-F$_2$ | n-C$_3$H$_7$ | |
| 489 | 5-CF$_3$ | n-C$_3$H$_7$ | |

TABLE 5-continued

Q = 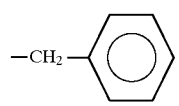

| Intermediate No. | (G)$_n$ | R$_1$ | Physical properties (m.p.: °C.) |
|---|---|---|---|
| 490 | 4-CH$_2$OCH$_3$ | n-C$_3$H$_7$ | |
| 491 | 4-CH$_2$SCH$_3$ | n-C$_3$H$_7$ | |
| 492 | 4-CH$_2$–C$_6$H$_5$ | n-C$_3$H$_7$ | |
| 493 | 4-CH$_2$N(CH$_3$)$_2$ | n-C$_3$H$_7$ | |
| 494 | 4-SO$_2$CH$_3$ | n-C$_3$H$_7$ | |
| 495 | 4-NHCH$_3$ | n-C$_3$H$_7$ | |
| 496 | 4-CON(CH$_3$)$_2$ | n-C$_3$H$_7$ | |
| 497 | 4-OCH$_3$ | iso-C$_3$H$_7$ | |
| 498 | 5-Br | —CH$_2$CH$_2$Cl | |
| 499 | 5-Br | —CH$_2$OCH$_3$ | |
| 500 | 4-CO$_2$CH$_3$ | —CH$_2$OCH$_3$ | |
| 501 | 4-N(CH$_3$)—SO$_2$CH$_3$ | —CH$_2$OCH$_3$ | |
| 502 | 4-N(CH$_3$)—COC$_2$H$_5$ | —CH$_2$OCH$_3$ | |
| 503 | 4-SO$_2$N(CH$_3$)$_2$ | —CH$_2$OCH$_3$ | |
| 504 | 4-OCH$_2$CH$_3$ | —CH$_2$SCH$_3$ | |
| 505 | 4-SCH$_3$ | —CH$_2$CO$_2$CH$_3$ | |
| 506 | 4-NHCH$_3$ | —CH$_2$SO$_2$CH$_3$ | |
| 507 | 4-CON(CH$_3$)$_2$ | —CH$_2$–C$_6$H$_5$ | |
| 508 | 3-OCH$_3$ | —CH$_2$N(CH$_3$)$_2$ | |
| 509 | 3-OCH$_3$ | —CH$_2$CH=CH$_2$ | |
| 510 | 3-OCH$_3$ | —OCH$_2$CH$_3$ | |
| 511 | 4-OCH$_2$CH$_3$ | —CO$_2$CH$_3$ | |
| 512 | 4-OCH$_3$ | —SO$_2$CH$_3$ | |
| 513 | 4-OCH$_3$ | —N(CH$_3$)$_2$ | |
| 514 | 4-OCH$_3$ | —CON(CH$_3$)$_2$ | |
| 515 | 4-OCH$_2$CH$_3$ | —SO$_2$N(CH$_3$)$_2$ | |

TABLE 6

Q = 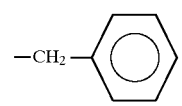

| Intermediate No. | (G)$_n$ | R$_1$ | Physical properties (m.p.: °C.) |
|---|---|---|---|
| 516 | 2-Cl | H | 233–238 |
| 517 | 2-Cl | CH$_3$ | 185–197 |
| 518 | 2-SCH$_3$ | CH$_3$ | |
| 519 | 2-CH$_2$CO$_2$CH$_3$ | C$_2$H$_5$ | |
| 520 | 2-CH$_2$SO$_2$CH$_3$ | C$_2$H$_5$ | |
| 521 | 2-Cl | n-C$_3$H$_7$ | 176–183 |
| 522 | 5,6-F$_2$ | n-C$_3$H$_7$ | |
| 523 | 5-CF$_3$ | n-C$_3$H$_7$ | |

TABLE 6-continued

Q = (pyridinone structure with (G)n at positions 5,6 and CH3 at position 2, carbonyl at 4, N-R1 at position 1)

| Intermediate No. | (G)n | R1 | Physical properties (m.p.: °C.) |
|---|---|---|---|
| 524 | 2-CH₂OCH₃ | n-C₃H₇ | |
| 525 | 2-CH₂SCH₃ | n-C₃H₇ | |
| 526 | 2-CH₂—C₆H₅ | n-C₃H₇ | |
| 527 | 2-CH₂N(CH₃)₂ | n-C₃H₇ | |
| 528 | 2-SO₂CH₃ | n-C₃H₇ | |
| 529 | 2-NHCH₃ | n-C₃H₇ | |
| 530 | 2-CON(CH₃)₂ | n-C₃H₇ | |
| 531 | 2-OCH₃ | iso-C₃H₇ | |
| 532 | 5-Br | —CH₂CH₂Cl | |
| 533 | 5-Br | —CH₂OCH₃ | |
| 534 | 2-CO₂CH₃ | —CH₂OCH₃ | |
| 535 | 2-N(CH₃)—SO₂CH₃ | —CH₂OCH₃ | |
| 536 | 2-N(CH₃)—COC₂H₅ | —CH₂OCH₃ | |
| 537 | 2-SO₂N(CH₃)₂ | —CH₂OCH₃ | |
| 538 | 2-OCH₂CH₃ | —CH₂SCH₃ | |
| 539 | 2-SCH₃ | —CH₂CO₂CH₃ | |
| 540 | 2-NHCH₃ | —CH₂SO₂CH₃ | |
| 541 | 2-CON(CH₃)₂ | —CH₂—C₆H₅ | |
| 542 | 2-OCH₃ | —CH₂N(CH₃)₂ | |
| 543 | 2-OCH₃ | —CH₂CH=CH₂ | |
| 544 | 2-OCH₃ | —OCH₂CH₃ | |
| 545 | 2-OCH₂CH₃ | —CO₂CH₃ | |
| 546 | 2-OCH₃ | —SO₂CH₃ | |
| 547 | 2-OCH₃ | —N(CH₃)₂ | |
| 548 | 2-OCH₃ | —CON(CH₃)₂ | |
| 549 | 2-OCH₂CH₃ | —SO₂N(CH₃)₂ | |

TABLE 7

Q = (pyridinone structure with (G)n, carbonyl at 4, CH3 at 2, N-R1 at position 1)

| Intermediate No. | (G)n | R1 | Physical properties (m.p.: °C.) |
|---|---|---|---|
| 550 | 3-Cl | H | |
| 551 | 3-C₂H₅ | CH₃ | |
| 552 | 3-OCH₃ | CH₃ | |
| 553 | 3-SCH₃ | CH₃ | |
| 554 | 3-CH₂CO₂CH₃ | C₂H₅ | |
| 555 | 5-CH₂CO₂CH₃ | C₂H₅ | |
| 556 | 5,6-F₂ | n-C₃H₇ | |
| 557 | 5-CF₃ | n-C₃H₇ | |
| 558 | 6-CH₂OCH₃ | n-C₃H₇ | |
| 559 | 6-CH₂SCH₃ | n-C₃H₇ | |
| 560 | 3-CH₂—C₆H₅ | n-C₃H₇ | |
| 561 | 3-CH₂N(CH₃)₂ | n-C₃H₇ | |
| 562 | 3-SO₂CH₃ | n-C₃H₇ | |
| 563 | 3-NHCH₃ | n-C₃H₇ | |
| 564 | 3-CON(CH₃)₂ | n-C₃H₇ | |
| 565 | 3-OCH₃ | iso-C₃H₇ | |
| 566 | 5-Br | —CH₂CH₂Cl | |
| 567 | 5-Br | —CH₂OCH₃ | |
| 568 | 3-CO₂CH₃ | —CH₂OCH₃ | |
| 569 | 3-N(CH₃)—SO₂CH₃ | —CH₂OCH₃ | |
| 570 | 3-N(CH₃)—COC₂H₅ | —CH₂OCH₃ | |
| 571 | 3-SO₂N(CH₃)₂ | —CH₂OCH₃ | |
| 572 | 3-OCH₂CH₃ | —CH₂SCH₃ | |
| 573 | 3-SCH₃ | —CH₂CO₂CH₃ | |
| 574 | 3-NHCH₃ | —CH₂SO₂CH₃ | |
| 575 | 3-CON(CH₃)₂ | —CH₂—C₆H₅ | |
| 576 | 3-OCH₃ | —CH₂N(CH₃)₂ | |
| 577 | 3-OCH₃ | —CH₂CH=CH₂ | |
| 578 | 3-OCH₃ | —OCH₂CH₃ | |
| 579 | 3-OCH₂CH₃ | —CO₂CH₃ | |
| 580 | 3-OCH₃ | —SO₂CH₃ | |
| 581 | 3-OCH₃ | —N(CH₃)₂ | |
| 582 | 3-OCH₃ | —CON(CH₃)₂ | |
| 583 | 3-OCH₂CH₃ | —SO₂N(CH₃)₂ | |

TABLE 8

$$Q-SO_2NHCN \begin{array}{c} O \\ \| \\ R_8 \end{array} \begin{array}{c} X \\ N \\ A \\ N \\ Y \end{array} \quad (I)$$

| Comp. No. | Q Pyridone ring | R₁ | R₈ | X | Y | A | Physical properties (m.p.: °C.) |
|---|---|---|---|---|---|---|---|
| 1 | ![pyridone with CH₃, N-R₁, =O] | H | H | OCH₃ | OCH₃ | CH | 246–256 |
| 2 | " | H | H | CH₃ | OCH₃ | N | |
| 3 | " | CH₃ | H | OCH₃ | OCH₃ | CH | 194–198 |
| 4 | " | CH₃ | H | Cl | OCH₃ | CH | |
| 5 | " | CH₃ | H | CH₃ | CH₃ | CH | |
| 6 | " | CH₃ | H | CH₃ | OCH₃ | N | |
| 7 | " | CH₃ | H | OCHF₂ | OCHF₂ | CH | |
| 8 | " | CH₃ | H | NHCH₃ | OCH₃ | CH | |
| 9 | " | CH₃ | H | CH₂OCH₃ | OCH₃ | CH | |
| 10 | " | CH₃ | H | CH(OCH₃)₂ | OCH₃ | CH | |
| 11 | " | C₂H₅ | H | OCH₃ | OCH₃ | CH | 233–235 |
| 12 | " | C₂H₅ | H | Cl | OCH₃ | CH | 148–152 |
| 13 | " | C₂H₅ | H | CH₃ | CH₃ | CH | 177–181 |
| 14 | " | C₂H₅ | H | CH₃ | OCH₃ | N | 217–223 |
| 15 | " | C₂H₅ | H | OCH₃ | OCH₃ | N | |
| 16 | " | C₂H₅ | CH₃ | OCH₃ | OCH₃ | CH | |
| 17 | ![pyridone] | C₂H₅ | H | OCHF₂ | OCHF₂ | CH | |
| 18 | " | C₂H₅ | H | NHCH₃ | OCH₃ | CH | |
| 19 | " | C₂H₅ | H | CH₂OCH₃ | OCH₃ | CH | |
| 20 | " | C₂H₅ | H | CH(OCH₃)₂ | OCH₃ | CH | |
| 21 | " | n-C₃H₇ | H | OCH₃ | OCH₃ | CH | 180–183 |
| 22 | " | n-C₃H₇ | H | Cl | OCH₃ | CH | 178–181 |
| 23 | " | n-C₃H₇ | H | CH₃ | CH₃ | CH | |
| 24 | " | n-C₃H₇ | H | CH₃ | OCH₃ | N | 171–174 |
| 25 | " | n-C₃H₇ | H | OCH₃ | OCH₃ | N | 180–183 |
| 26 | " | n-C₃H₇ | CH₃ | OCH₃ | OCH₃ | CH | |
| 27 | " | n-C₃H₇ | H | OCHF₂ | OCH₃ | CH | |
| 28 | " | n-C₃H₇ | H | OCHF₂ | OCHF₂ | CH | |
| 29 | " | n-C₃H₇ | H | NHCH₃ | OCH₃ | CH | |
| 30 | " | n-C₃H₇ | H | CH₂OCH₃ | OCH₃ | CH | |
| 31 | " | n-C₃H₇ | H | CH(OCH₃)₂ | OCH₃ | CH | |
| 32 | " | iso-C₃H₇ | H | OCH₃ | OCH₃ | CH | 191–198 |
| 33 | " | iso-C₃H₇ | H | Cl | OCH₃ | CH | |
| 34 | " | iso-C₃H₇ | H | CH₃ | OCH₃ | N | |
| 35 | " | n-C₄H₉ | H | OCH₃ | OCH₃ | CH | 167–170 |
| 36 | ![pyridone] | n-C₄H₉ | H | Cl | OCH₃ | CH | |
| 37 | " | n-C₄H₉ | H | CH₃ | OCH₃ | N | |
| 38 | " | n-C₄H₉ | H | OCH₃ | OCH₃ | N | |
| 39 | " | sec-C₄H₉ | H | OCH₃ | OCH₃ | CH | |
| 40 | " | sec-C₄H₉ | H | Cl | OCH₃ | CH | |
| 41 | " | sec-C₄H₉ | H | CH₃ | OCH₃ | N | |
| 42 | " | tert-C₄H₉ | H | OCH₃ | OCH₃ | CH | |
| 43 | " | tert-C₄H₉ | H | Cl | OCH₃ | CH | |
| 44 | " | n-C₅H₁₁ | H | CH₃ | OCH₃ | N | |

TABLE 8-continued

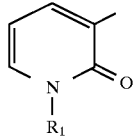

| Comp. No. | Q Pyridone ring | R₁ | R₈ | X | Y | A | Physical properties (m.p.: °C.) |
|---|---|---|---|---|---|---|---|
| 45 | " | n-C₅H₁₁ | H | OCH₃ | OCH₃ | CH | |
| 46 | " | n-C₆H₁₃ | H | OCH₃ | OCH₃ | CH | |
| 47 | " | —CH₂Cl | H | OCH₃ | OCH₃ | CH | |
| 48 | " | —CHCl₂ | H | OCH₃ | OCH₃ | CH | |
| 49 | " | —CH₂CH₂Cl | H | OCH₃ | OCH₃ | CH | 190–193 |
| 50 | " | —CH₂CH₂Cl | H | CH₃ | OCH₃ | N | |
| 51 | " | —(CH₂)₃Cl | H | OCH₃ | OCH₃ | CH | 183–187 |
| 52 | " | —CH(Cl)CH₃ | H | OCH₃ | OCH₃ | CH | |
| 53 | " | —CH₂CH(Cl)CH₃ | H | OCH₃ | OCH₃ | CH | |
| 54 | " | —CH(CH₂Cl)₂ | H | OCH₃ | OCH₃ | CH | |
| 55 | 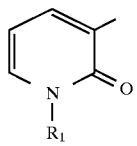 | —CH₂F | H | OCH₃ | OCH₃ | CH | |
| 56 | " | —CHF₂ | H | OCH₃ | OCH₃ | CH | |
| 57 | " | —CHF₂ | H | CH₃ | OCH₃ | N | |
| 58 | " | —CHF₂ | CH₃ | OCH₃ | OCH₃ | CH | |
| 59 | " | —CF₃ | H | OCH₃ | OCH₃ | CH | |
| 60 | " | —(CH₂)₃F | H | OCH₃ | OCH₃ | CH | 179–184 |
| 61 | " | —CH₂OCH₃ | H | OCH₃ | OCH₃ | CH | 193–196 |
| 62 | " | —CH₂OCH₃ | H | Cl | OCH₃ | CH | |
| 63 | " | —CH₂OCH₃ | H | CH₃ | CH₃ | CH | |
| 64 | " | —CH₂OCH₃ | H | CH₃ | OCH₃ | N | |
| 65 | " | —CH₂OCH₃ | H | OCH₃ | OCH₃ | N | |
| 66 | " | —CH₂OCH₃ | CH₃ | OCH₃ | OCH₃ | CH | |
| 67 | " | —CH₂OCH₃ | H | OCHF₂ | OCHF₂ | CH | |
| 68 | " | —CH₂OCH₃ | H | NHCH₃ | OCH₃ | CH | |
| 69 | " | —CH₂OCH₂CH₃ | H | OCH₃ | OCH₃ | CH | 179–183 |
| 70 | " | —CH₂OCH(CH₃)₂ | H | OCH₃ | OCH₃ | CH | 165–167 |
| 71 | " | —(CH₂)₂OCH₃ | H | OCH₃ | OCH₃ | CH | 188–191 |
| 72 | " | —CH₂SCH₃ | H | OCH₃ | OCH₃ | CH | 189–193 |
| 73 | " | —(CH₂)₂SCH₃ | H | OCH₃ | OCH₃ | CH | |
| 74 | 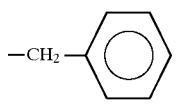 | —CH₂COCH₃ | H | OCH₃ | OCH₃ | CH | 197–205 |
| 75 | " | —CH₂CO₂CH₃ | H | OCH₃ | OCH₃ | CH | 146–149 |
| 76 | " | —CH₂SOCH₃ | H | OCH₃ | OCH₃ | CH | 190–193 |
| 77 | " | —CH₂SO₂CH₃ | H | OCH₃ | OCH₃ | CH | 213–217 |
| 78 | " | 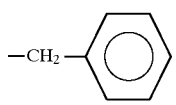 | H | OCH₃ | OCH₃ | CH | 103–106 |
| 79 | " | —CH₂—C₆H₅ | H | CH₃ | OCH₃ | N | |

TABLE 8-continued

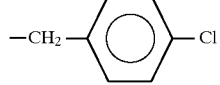

| | Q | | | | | | Physical |
|---|---|---|---|---|---|---|---|
| Comp. No. | Pyridone ring | R₁ | R₈ | X | Y | A | properties (m.p.: °C.) |
| 80 | " | 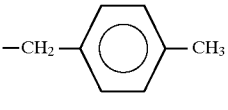 —CH₂—(2,4-Cl₂-C₆H₃) | H | OCH₃ | OCH₃ | CH | |
| 81 | " | —CH₂—(4-CH₃-C₆H₄) | H | OCH₃ | OCH₃ | CH | |
| 82 | " | —CH₂OCH₂—C₆H₅ | H | OCH₃ | OCH₃ | CH | 152–156 |
| 83 | " | —CH₂NHCH₃ | H | OCH₃ | OCH₃ | CH | |
| 84 | " | —CH₂N(CH₃)₂ | H | OCH₃ | OCH₃ | CH | |
| 85 | " | —CH₂CH₂CN | H | OCH₃ | OCH₃ | CH | |
| 86 | " | —CH₂CH₂NO₂ | H | OCH₃ | OCH₃ | CH | |
| 87 | " | —CH=CH₂ | H | OCH₃ | OCH₃ | CH | |
| 88 | " | —CH₂CH=CH₂ | H | OCH₃ | OCH₃ | CH | 197–199 |
| 89 | 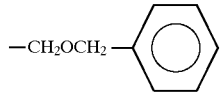 | —CH₂CH=CHCH₃ | H | OCH₃ | OCH₃ | CH | |
| 90 | " | —CH₂C(CH₃)=CH₂ | H | OCH₃ | OCH₃ | CH | 187–191 |
| 91 | " | —CH₂CH=CCl₂ | H | OCH₃ | OCH₃ | CH | |
| 92 | " | —CH₂CH=CF₂ | H | OCH₃ | OCH₃ | CH | |
| 93 | " | —C≡CH | H | OCH₃ | OCH₃ | CH | |
| 94 | " | —CH₂C≡CH | H | OCH₃ | OCH₃ | CH | 199–205 |
| 95 | " | —OCH₂CH₃ | H | OCH₃ | OCH₃ | CH | 180–182 |
| 96 | " | —OCH₂CH₂Cl | H | OCH₃ | OCH₃ | CH | |
| 97 | " | —SCH₃ | H | OCH₃ | OCH₃ | CH | |
| 98 | " | —SCHF₂ | H | OCH₃ | OCH₃ | CH | |
| 99 | " | —COCH₃ | H | OCH₃ | OCH₃ | CH | |
| 100 | " | —COCH₂CH₂Cl | H | OCH₃ | OCH₃ | CH | |
| 101 | " | —CO₂CH₃ | H | OCH₃ | OCH₃ | CH | 188–192 |
| 102 | " | —CO₂CH₂CH₂Cl | H | OCH₃ | OCH₃ | CH | |
| 103 | " | —SOCH₃ | H | OCH₃ | OCH₃ | CH | |
| 104 | " | —SOCHF₂ | H | OCH₃ | OCH₃ | CH | |
| 105 | " | —SO₂CH₃ | H | OCH₃ | OCH₃ | CH | 268–272 |
| 106 | " | —SO₂(CH₂)₃F | H | OCH₃ | OCH₃ | CH | |
| 107 | " | —NH₂ | H | OCH₃ | OCH₃ | CH | |
| 108 | 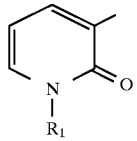 | —NHCH₃ | H | OCH₃ | OCH₃ | CH | |
| 109 | " | —N(CH₃)₂ | H | OCH₃ | OCH₃ | CH | |
| 110 | " | —NHSOCH₃ | H | OCH₃ | OCH₃ | CH | |

TABLE 8-continued $$Q-SO_2NHCN\underset{R_8}{\overset{O}{\|}}\underset{N}{\overset{N}{=}}\underset{Y}{\overset{X}{\underset{A}{\bigg\langle}}}\quad (I)$$

| Comp. No. | Q Pyridone ring | R₁ | R₈ | X | Y | A | Physical properties (m.p.: °C.) |
|---|---|---|---|---|---|---|---|
| 111 | " | —N(CH₃)—SO₂CH₃ | H | OCH₃ | OCH₃ | CH | |
| 112 | " | —N(C₂H₅)—SO₂CH(CH₃)₂ | H | OCH₃ | OCH₃ | CH | |
| 113 | " | —N(CH₃)—COC₂H₅ | H | OCH₃ | OCH₃ | CH | |
| 114 | " | —CONH₂ | H | OCH₃ | OCH₃ | CH | |
| 115 | " | —CONHCH₃ | H | OCH₃ | OCH₃ | CH | |
| 116 | " | —CON(CH₃)₂ | H | OCH₃ | OCH₃ | CH | 198–201 |
| 117 | " | —SO₂NHCH₃ | H | OCH₃ | OCH₃ | CH | |
| 118 | " | —SO₂N(CH₃)₂ | H | OCH₃ | OCH₃ | CH | |
| 119 | " | —SO₂N(CH₃)—COCH₃ | H | OCH₃ | OCH₃ | CH | |
| 120 | " | —SO₂N(C₂H₅)—CO₂CH₃ | H | OCH₃ | OCH₃ | CH | |
| 121 | 4-methyl-2-pyridone (N-R₁) | H | H | OCH₃ | OCH₃ | CH | |
| 122 | " | H | H | CH₃ | OCH₃ | N | |
| 123 | " | CH₃ | H | OCH₃ | OCH₃ | CH | |
| 124 | " | CH₃ | H | Cl | OCH₃ | CH | |
| 125 | " | CH₃ | H | CH₃ | CH₃ | CH | |
| 126 | " | CH₃ | H | CH₃ | OCH₃ | N | |
| 127 | " | CH₃ | H | OCHF₂ | OCHF₂ | CH | |
| 128 | " | CH₃ | H | NHCH₃ | OCH₃ | CH | |
| 129 | " | C₂H₅ | H | OCH₃ | OCH₃ | CH | |
| 130 | " | C₂H₅ | H | Cl | OCH₃ | CH | |
| 131 | " | C₂H₅ | H | CH₃ | CH₃ | CH | |
| 132 | " | C₂H₅ | H | CH₃ | OCH₃ | N | |
| 133 | " | C₂H₅ | H | OCH₃ | OCH₃ | N | |
| 134 | " | C₂H₅ | CH₃ | OCH₃ | OCH₃ | CH | |
| 135 | " | C₂H₅ | H | OCHF₂ | OCHF₂ | CH | |
| 136 | " | C₂H₅ | H | NHCH₃ | OCH₃ | CH | |
| 137 | " | n-C₃H₇ | H | OCH₃ | OCH₃ | CH | |
| 138 | " | n-C₃H₇ | H | Cl | OCH₃ | CH | |
| 139 | " | n-C₃H₇ | H | CH₃ | CH₃ | CH | |
| 140 | " | n-C₃H₇ | H | CH₃ | OCH₃ | N | |
| 141 | 4-methyl-2-pyridone (N-R₁) | n-C₃H₇ | H | OCH₃ | OCH₃ | N | |
| 142 | " | n-C₃H₇ | CH₃ | OCH₃ | OCH₃ | CH | |
| 143 | " | n-C₃H₇ | H | OCHF₂ | OCHF₂ | CH | |

TABLE 8-continued

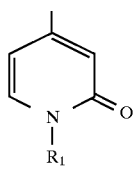

|  | Q | | | | | | Physical |
|---|---|---|---|---|---|---|---|
| Comp. No. | Pyridone ring | $R_1$ | $R_8$ | X | Y | A | properties (m.p.: °C.) |
| 144 | " | n-$C_3H_7$ | H | $NHCH_3$ | $OCH_3$ | CH | |
| 145 | " | n-$C_3H_7$ | H | $CH_2OCH_3$ | $OCH_3$ | CH | |
| 146 | " | n-$C_3H_7$ | H | $CH(OCH_3)_2$ | $OCH_3$ | CH | |
| 147 | " | iso-$C_3H_7$ | H | $OCH_3$ | $OCH_3$ | CH | |
| 148 | " | n-$C_4H_9$ | H | $OCH_3$ | $OCH_3$ | CH | |
| 149 | " | sec-$C_4H_9$ | H | $OCH_3$ | $OCH_3$ | CH | |
| 150 | " | tert-$C_4H_9$ | H | $OCH_3$ | $OCH_3$ | CH | |
| 151 | " | n-$C_5H_{11}$ | H | $OCH_3$ | $OCH_3$ | CH | |
| 152 | " | n-$C_6H_{13}$ | H | $OCH_3$ | $OCH_3$ | CH | |
| 153 | " | —$CH_2Cl$ | H | $OCH_3$ | $OCH_3$ | CH | |
| 154 | " | —$CHCl_2$ | H | $OCH_3$ | $OCH_3$ | CH | |
| 155 | " | —$CH_2CH_2Cl$ | H | $OCH_3$ | $OCH_3$ | CH | |
| 156 | " | —$(CH_2)_3Cl$ | H | $OCH_3$ | $OCH_3$ | CH | |
| 157 | " | —$CH(Cl)CH_3$ | H | $OCH_3$ | $OCH_3$ | CH | |
| 158 | " | —$CH_2CH(Cl)CH_3$ | H | $OCH_3$ | $OCH_3$ | CH | |
| 159 | " | —$CH_2F$ | H | $OCH_3$ | $OCH_3$ | CH | |
| 160 | 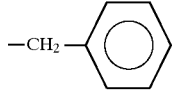 | —$CHF_2$ | H | $OCH_3$ | $OCH_3$ | CH | |
| 161 | " | —$CF_3$ | H | $OCH_3$ | $OCH_3$ | CH | |
| 162 | " | —$(CH_2)_3F$ | H | $OCH_3$ | $OCH_3$ | CH | |
| 163 | " | —$CH_2OCH_3$ | H | $OCH_3$ | $OCH_3$ | CH | |
| 164 | " | —$CH_2OCH_2CH_3$ | H | $OCH_3$ | $OCH_3$ | CH | |
| 165 | " | —$(CH_2)_2OCH_3$ | H | $OCH_3$ | $OCH_3$ | CH | |
| 166 | " | —$CH_2SCH_3$ | H | $OCH_3$ | $OCH_3$ | CH | |
| 167 | " | —$(CH_2)_2SCH_3$ | H | $OCH_3$ | $OCH_3$ | CH | |
| 168 | " | —$CH_2COCH_3$ | H | $OCH_3$ | $OCH_3$ | CH | |
| 169 | " | —$CH_2CO_2CH_3$ | H | $OCH_3$ | $OCH_3$ | CH | |
| 170 | " | —$CH_2SOCH_3$ | H | $OCH_3$ | $OCH_3$ | CH | |
| 171 | " | —$CH_2SO_2CH_3$ | H | $OCH_3$ | $OCH_3$ | CH | |
| 172 | " | —$CH_2$-Ph | H | $OCH_3$ | $OCH_3$ | CH | |
| 173 | " | —$CH_2NHCH_3$ | H | $OCH_3$ | $OCH_3$ | CH | |
| 174 | " | —$CH_2N(CH_3)_2$ | H | $OCH_3$ | $OCH_3$ | CH | |
| 175 | " | —$CH_2CH_2CN$ | H | $OCH_3$ | $OCH_3$ | CH | |
| 176 | " | —$CH=CH_2$ | H | $OCH_3$ | $OCH_3$ | CH | |
| 177 | " | —$CH_2CH=CH_2$ | H | $OCH_3$ | $OCH_3$ | CH | |
| 178 | 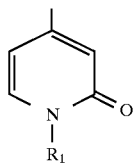 | —$CH_2C(CH_3)=CH_2$ | H | $OCH_3$ | $OCH_3$ | CH | |
| 179 | " | —$CH_2CH=CCl_2$ | H | $OCH_3$ | $OCH_3$ | CH | |
| 180 | " | —$CH_2CH=CF_2$ | H | $OCH_3$ | $OCH_3$ | CH | |
| 181 | " | —$C≡CH$ | H | $OCH_3$ | $OCH_3$ | CH | |
| 182 | " | —$CH_2C≡CH$ | H | $OCH_3$ | $OCH_3$ | CH | |
| 183 | " | —$OCH_2CH_3$ | H | $OCH_3$ | $OCH_3$ | CH | |
| 184 | " | —$SCH_3$ | H | $OCH_3$ | $OCH_3$ | CH | |

TABLE 8-continued

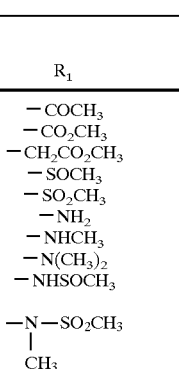

| Comp. No. | Q Pyridone ring | R₁ | R₈ | X | Y | A | Physical properties (m.p.: °C.) |
|---|---|---|---|---|---|---|---|
| 185 | " | —COCH₃ | H | OCH₃ | OCH₃ | CH | |
| 186 | " | —CO₂CH₃ | H | OCH₃ | OCH₃ | CH | |
| 187 | " | —CH₂CO₂CH₃ | H | OCH₃ | OCH₃ | CH | |
| 188 | " | —SOCH₃ | H | OCH₃ | OCH₃ | CH | |
| 189 | " | —SO₂CH₃ | H | OCH₃ | OCH₃ | CH | |
| 190 | " | —NH₂ | H | OCH₃ | OCH₃ | CH | |
| 191 | " | —NHCH₃ | H | OCH₃ | OCH₃ | CH | |
| 192 | " | —N(CH₃)₂ | H | OCH₃ | OCH₃ | CH | |
| 193 | " | —NHSOCH₃ | H | OCH₃ | OCH₃ | CH | |
| 194 | " | —N(CH₃)—SO₂CH₃ | H | OCH₃ | OCH₃ | CH | |
| 195 | 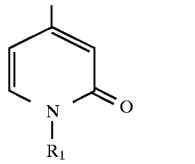 | —N(CH₃)—COC₂H₅ | H | OCH₃ | OCH₃ | CH | |
| 196 | " | —CONH₂ | H | OCH₃ | OCH₃ | CH | |
| 197 | " | —CONHCH₃ | H | OCH₃ | OCH₃ | CH | |
| 198 | " | —CON(CH₃)₂ | H | OCH₃ | OCH₃ | CH | |
| 199 | " | —SO₂NHCH₃ | H | OCH₃ | OCH₃ | CH | |
| 200 | " | —SO₂N(CH₃)₂ | H | OCH₃ | OCH₃ | CH | |
| 201 | " | —SO₂N(CH₃)—COCH₃ | H | OCH₃ | OCH₃ | CH | |
| 202 | " | —SO₂N(C₂H₅)—CO₂CH₃ | H | OCH₃ | OCH₃ | CH | |
| 203 | 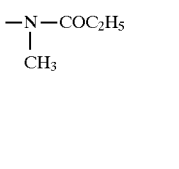 | H | H | OCH₃ | OCH₃ | CH | 200–205 |
| 204 | " | H | H | CH₃ | OCH₃ | N | |
| 205 | " | CH₃ | H | OCH₃ | OCH₃ | CH | 168–169 |
| 206 | " | CH₃ | H | Cl | OCH₃ | CH | |
| 207 | " | CH₃ | H | CH₃ | CH₃ | CH | |
| 208 | " | CH₃ | H | CH₃ | OCH₃ | N | |
| 209 | 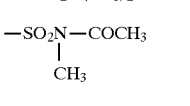 | CH₃ | H | OCHF₂ | OCHF₂ | CH | |
| 210 | " | CH₃ | H | NHCH₃ | OCH₃ | CH | |
| 211 | " | CH₃ | H | CH₂OCH₃ | OCH₃ | CH | |
| 212 | " | CH₃ | H | CH(OCH₃)₂ | OCH₃ | CH | |
| 213 | " | C₂H₅ | H | OCH₃ | OCH₃ | CH | 161–165 |
| 214 | " | C₂H₅ | H | Cl | OCH₃ | CH | |
| 215 | " | C₂H₅ | H | CH₃ | CH₃ | CH | |
| 216 | " | C₂H₅ | H | CH₃ | OCH₃ | N | |
| 217 | " | C₂H₅ | H | OCH₃ | OCH₃ | N | |

TABLE 8-continued

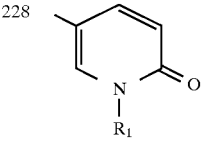

| Comp. No. | Q Pyridone ring | R₁ | R₈ | X | Y | A | Physical properties (m.p.: °C.) |
|---|---|---|---|---|---|---|---|
| 218 | " | C₂H₅ | CH₃ | OCH₃ | OCH₃ | CH | |
| 219 | " | C₂H₅ | H | OCHF₂ | OCHF₂ | CH | |
| 220 | " | C₂H₅ | H | NHCH₃ | OCH₃ | CH | |
| 221 | " | n-C₃H₇ | H | OCH₃ | OCH₃ | CH | |
| 222 | " | n-C₃H₇ | H | Cl | OCH₃ | CH | |
| 223 | " | n-C₃H₇ | H | CH₃ | CH₃ | CH | |
| 224 | " | n-C₃H₇ | H | CH₃ | OCH₃ | N | |
| 225 | " | n-C₃H₇ | H | OCH₃ | OCH₃ | N | |
| 226 | " | n-C₃H₇ | CH₃ | OCH₃ | OCH₃ | CH | |
| 227 | " | n-C₃H₇ | H | OCHF₂ | OCHF₂ | CH | |
| 228 | 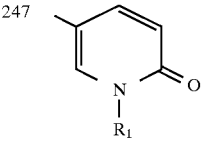 | n-C₃H₇ | H | NHCH₃ | OCH₃ | CH | |
| 229 | " | iso-C₃H₇ | H | OCH₃ | OCH₃ | CH | |
| 230 | " | n-C₄H₉ | H | OCH₃ | OCH₃ | CH | |
| 231 | " | sec-C₄H₉ | H | OCH₃ | OCH₃ | CH | |
| 232 | " | tert-C₄H₉ | H | OCH₃ | OCH₃ | CH | |
| 233 | " | n-C₅H₁₁ | H | OCH₃ | OCH₃ | CH | |
| 234 | " | n-C₆H₁₃ | H | OCH₃ | OCH₃ | CH | |
| 235 | " | —CH₂Cl | H | OCH₃ | OCH₃ | CH | |
| 236 | " | —CHCl₂ | H | OCH₃ | OCH₃ | CH | |
| 237 | " | —CH₂CH₂Cl | H | OCH₃ | OCH₃ | CH | |
| 238 | " | —(CH₂)₃Cl | H | OCH₃ | OCH₃ | CH | |
| 239 | " | —CH(Cl)CH₃ | H | OCH₃ | OCH₃ | CH | |
| 240 | " | —CH₂CH(Cl)CH₃ | H | OCH₃ | OCH₃ | CH | |
| 241 | " | —CH₂F | H | OCH₃ | OCH₃ | CH | |
| 242 | " | —CHF₂ | H | OCH₃ | OCH₃ | CH | |
| 243 | " | —CF₃ | H | OCH₃ | OCH₃ | CH | |
| 244 | " | —(CH₂)₃F | H | OCH₃ | OCH₃ | CH | |
| 245 | " | —CH₂OCH₃ | H | OCH₃ | OCH₃ | CH | 172-174 |
| 246 | " | —CH₂OCH₂CH₃ | H | OCH₃ | OCH₃ | CH | |
| 247 | 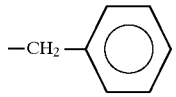 | —(CH₂)₂OCH₃ | H | OCH₃ | OCH₃ | CH | |
| 248 | " | —CH₂SCH₃ | H | OCH₃ | OCH₃ | CH | |
| 249 | " | —(CH₂)₂SCH₃ | H | OCH₃ | OCH₃ | CH | |
| 250 | " | —CH₂COCH₃ | H | OCH₃ | OCH₃ | CH | |
| 251 | " | —CH₂CO₂CH₃ | H | OCH₃ | OCH₃ | CH | |
| 252 | " | —CH₂SOCH₃ | H | OCH₃ | OCH₃ | CH | |
| 253 | " | —CH₂SO₂CH₃ | H | OCH₃ | OCH₃ | CH | |
| 254 | " | —CH₂—C₆H₅ | H | OCH₃ | OCH₃ | CH | |
| 255 | " | —CH₂NHCH₃ | H | OCH₃ | OCH₃ | CH | |
| 256 | " | —CH₂N(CH₃)₂ | H | OCH₃ | OCH₃ | CH | |
| 257 | " | —CH₂CH₂CN | H | OCH₃ | OCH₃ | CH | |
| 258 | " | —CH=CH₂ | H | OCH₃ | OCH₃ | CH | |
| 259 | " | —CH₂CH=CH₂ | H | OCH₃ | OCH₃ | CH | |

TABLE 8-continued

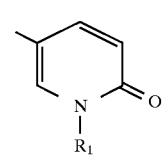

| Comp. No. | Q Pyridone ring | R₁ | R₈ | X | Y | A | Physical properties (m.p.: °C.) |
|---|---|---|---|---|---|---|---|
| 260 | " | —CH₂C(CH₃)=CH₂ | H | OCH₃ | OCH₃ | CH | |
| 261 | " | —CH₂CH=CCl₂ | H | OCH₃ | OCH₃ | CH | |
| 262 | " | —CH₂CH=CF₂ | H | OCH₃ | OCH₃ | CH | |
| 263 | " | —C≡CH | H | OCH₃ | OCH₃ | CH | |
| 264 | 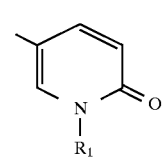 | —CH₂C≡CH | H | OCH₃ | OCH₃ | CH | |
| 265 | " | —OCH₂CH₃ | H | OCH₃ | OCH₃ | CH | |
| 266 | " | —SCH₃ | H | OCH₃ | OCH₃ | CH | |
| 267 | " | —COCH₃ | H | OCH₃ | OCH₃ | CH | |
| 268 | " | —CO₂CH₃ | H | OCH₃ | OCH₃ | CH | |
| 269 | " | —CH₂CO₂CH₃ | H | OCH₃ | OCH₃ | CH | |
| 270 | " | —SOCH₃ | H | OCH₃ | OCH₃ | CH | |
| 271 | " | —SO₂CH₃ | H | OCH₃ | OCH₃ | CH | |
| 272 | " | —NH₂ | H | OCH₃ | OCH₃ | CH | |
| 273 | " | —NHCH₃ | H | OCH₃ | OCH₃ | CH | |
| 274 | " | —N(CH₃)₂ | H | OCH₃ | OCH₃ | CH | |
| 275 | " | —NHSOCH₃ | H | OCH₃ | OCH₃ | CH | |
| 276 | " | —N(CH₃)—SO₂CH₃ | H | OCH₃ | OCH₃ | CH | |
| 277 | " | —N(CH₃)—COC₂H₅ | H | OCH₃ | OCH₃ | CH | |
| 278 | " | —CONH₂ | H | OCH₃ | OCH₃ | CH | |
| 279 | " | —CONHCH₃ | H | OCH₃ | OCH₃ | CH | |
| 280 | " | —CON(CH₃)₂ | H | OCH₃ | OCH₃ | CH | |
| 281 | 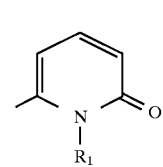 | —SO₂NHCH₃ | H | OCH₃ | OCH₃ | CH | |
| 282 | " | —SO₂N(CH₃)₂ | H | OCH₃ | OCH₃ | CH | |
| 283 | " | —SO₂N(CH₃)—COCH₃ | H | OCH₃ | OCH₃ | CH | |
| 284 | " | —SO₂N(C₂H₅)—CO₂CH₃ | H | OCH₃ | OCH₃ | CH | |
| 285 | (6-methyl pyridone) | H | H | OCH₃ | OCH₃ | CH | 171–174 |
| 286 | " | H | H | CH₃ | OCH₃ | N | |

TABLE 8-continued

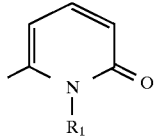

|  | Q |  |  |  |  |  | Physical |
|---|---|---|---|---|---|---|---|
| Comp. No. | Pyridone ring | $R_1$ | $R_8$ | X | Y | A | properties (m.p.: °C.) |
| 287 | " | $CH_3$ | H | $OCH_3$ | $OCH_3$ | CH | 162–165 |
| 288 | " | $CH_3$ | H | Cl | $OCH_3$ | CH |  |
| 289 | " | $CH_3$ | H | $CH_3$ | $CH_3$ | CH |  |
| 290 | " | $CH_3$ | H | $CH_3$ | $OCH_3$ | N |  |
| 291 | " | $CH_3$ | H | $OCHF_2$ | $OCHF_2$ | CH |  |
| 292 | " | $CH_3$ | H | $NHCH_3$ | $OCH_3$ | CH |  |
| 293 | " | $C_2H_5$ | H | $OCH_3$ | $OCH_3$ | CH |  |
| 294 | " | $C_2H_5$ | H | Cl | $OCH_3$ | CH |  |
| 295 | 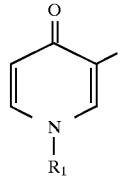 | $C_2H_5$ | H | $CH_3$ | $CH_3$ | CH |  |
| 296 | " | $C_2H_5$ | H | $CH_3$ | $OCH_3$ | N |  |
| 297 | " | $C_2H_5$ | H | $OCH_3$ | $OCH_3$ | N |  |
| 298 | " | $C_2H_5$ | $CH_3$ | $OCH_3$ | $OCH_3$ | CH |  |
| 299 | " | $C_2H_5$ | H | $OCHF_2$ | $OCHF_2$ | CH |  |
| 300 | " | $C_2H_5$ | H | $NHCH_3$ | $OCH_3$ | CH |  |
| 301 | " | $C_2H_5$ | H | $CH_2OCH_3$ | $OCH_3$ | CH |  |
| 302 | " | $C_2H_5$ | H | $CH(OCH_3)_2$ | $OCH_3$ | CH |  |
| 303 | " | $-CH_2F$ | H | $OCH_3$ | $OCH_3$ | CH |  |
| 304 | " | $-CHF_2$ | H | $OCH_3$ | $OCH_3$ | CH |  |
| 305 | " | $-CF_3$ | H | $OCH_3$ | $OCH_3$ | CH |  |
| 306 | " | $-(CH_2)_2F$ | H | $OCH_3$ | $OCH_3$ | CH |  |
| 307 | " | $-OCH_2CH_3$ | H | $OCH_3$ | $OCH_3$ | CH |  |
| 308 | " | $-SCH_3$ | H | $OCH_3$ | $OCH_3$ | CH |  |
| 309 | " | $-NH_2$ | H | $OCH_3$ | $OCH_3$ | CH |  |
| 310 | " | $-NHCH_3$ | H | $OCH_3$ | $OCH_3$ | CH |  |
| 311 |  | H | H | $OCH_3$ | $OCH_3$ | CH | 199 decomposed |
| 312 | " | H | H | $CH_3$ | $OCH_3$ | N |  |
| 313 | " | $CH_3$ | H | $OCH_3$ | $OCH_3$ | CH | 161 decomposed |
| 314 | " | $CH_3$ | H | Cl | $OCH_3$ | CH |  |
| 315 | " | $CH_3$ | H | $CH_3$ | $CH_3$ | CH |  |
| 316 | " | $CH_3$ | H | $CH_3$ | $OCH_3$ | N | 173 decomposed |
| 317 | " | $CH_3$ | H | $OCHF_2$ | $OCHF_2$ | CH |  |
| 318 | " | $CH_3$ | H | $NHCH_3$ | $OCH_3$ | CH |  |
| 319 | " | $CH_3$ | H | $CH_2OCH_3$ | $OCH_3$ | CH |  |
| 320 | " | $CH_3$ | H | $CH(OCH_3)_2$ | $OCH_3$ | CH |  |
| 321 | " | $C_2H_5$ | H | $OCH_3$ | $OCH_3$ | CH | 170–177 |
| 322 | " | $C_2H_5$ | H | Cl | $OCH_3$ | CH |  |
| 323 | " | $C_2H_5$ | H | $CH_3$ | $CH_3$ | CH |  |
| 324 | " | $C_2H_5$ | H | $CH_3$ | $OCH_3$ | N | 158–161 |
| 325 | " | $C_2H_5$ | H | $OCH_3$ | $OCH_3$ | N |  |
| 326 | " | $C_2H_5$ | $CH_3$ | $OCH_3$ | $OCH_3$ | CH |  |
| 327 | " | $C_2H_5$ | H | $OCHF_2$ | $OCHF_2$ | CH |  |
| 328 | " | $C_2H_5$ | H | $NHCH_3$ | $OCH_3$ | CH |  |

TABLE 8-continued $$Q-SO_2NHCN\underset{R_8}{\overset{O}{\parallel}}\begin{array}{c}X\\N\end{array}\overset{(I)}{\underset{Y}{\begin{array}{c}\\A\\N\end{array}}}$$

| Comp. No. | Q Pyridone ring | R₁ | R₈ | X | Y | A | Physical properties (m.p.: °C.) |
|---|---|---|---|---|---|---|---|
| 329 | O=⟨pyridone⟩-N-R₁ (3-methyl) | n-C₃H₇ | H | OCH₃ | OCH₃ | CH | 174–186 |
| 330 | " | n-C₃H₇ | H | Cl | OCH₃ | CH | |
| 331 | " | n-C₃H₇ | H | CH₃ | CH₃ | CH | |
| 332 | " | n-C₃H₇ | H | CH₃ | OCH₃ | N | |
| 333 | " | n-C₃H₇ | H | OCH₃ | OCH₃ | N | |
| 334 | " | n-C₃H₇ | CH₃ | OCH₃ | OCH₃ | CH | |
| 335 | " | n-C₃H₇ | H | OCHF₂ | OCHF₂ | CH | |
| 336 | " | n-C₃H₇ | H | NHCH₃ | OCH₃ | CH | |
| 337 | " | iso-C₃H₇ | H | OCH₃ | OCH₃ | CH | 144-166 |
| 338 | " | n-C₄H₉ | H | OCH₃ | OCH₃ | CH | 165-176 |
| 339 | " | sec-C₄H₉ | H | OCH₃ | OCH₃ | CH | |
| 340 | " | tert-C₄H₉ | H | OCH₃ | OCH₃ | CH | |
| 341 | " | n-C₅H₁₁ | H | OCH₃ | OCH₃ | CH | |
| 342 | " | n-C₆H₁₃ | H | OCH₃ | OCH₃ | CH | |
| 343 | " | —CH₂Cl | H | OCH₃ | OCH₃ | CH | |
| 344 | " | —CHCl₂ | H | OCH₃ | OCH₃ | CH | |
| 345 | " | —CH₂CH₂Cl | H | OCH₃ | OCH₃ | CH | 163-170 |
| 346 | " | —(CH₂)₃Cl | H | OCH₃ | OCH₃ | CH | |
| 347 | " | —CH(Cl)CH₃ | H | OCH₃ | OCH₃ | CH | |
| 348 | O=⟨pyridone⟩-N-R₁ (3-methyl) | —CH₂CH(Cl)CH₃ | H | OCH₃ | OCH₃ | CH | |
| 349 | " | —CH₂F | H | OCH₃ | OCH₃ | CH | |
| 350 | " | —CHF₂ | H | OCH₃ | OCH₃ | CH | 187–192 |
| 351 | " | —CHF₂ | H | CH₃ | OCH₃ | N | 210–222 |
| 352 | " | —CF₃ | H | OCH₃ | OCH₃ | CH | |
| 353 | " | —(CH₂)₂F | H | OCH₃ | OCH₃ | CH | 169–173 |
| 354 | " | —(CH₂)₃F | H | OCH₃ | OCH₃ | CH | |
| 355 | " | —CH₂OCH₃ | H | OCH₃ | OCH₃ | CH | 195 decomposed |
| 356 | " | —CH₂OCH₂CH₃ | H | OCH₃ | OCH₃ | CH | |
| 357 | " | —(CH₂)₂OCH₃ | H | OCH₃ | OCH₃ | CH | |
| 358 | " | —CH₂SCH₃ | H | OCH₃ | OCH₃ | CH | |
| 359 | " | —(CH₂)₂SCH₃ | H | OCH₃ | OCH₃ | CH | |
| 360 | " | —CH₂COCH₃ | H | OCH₃ | OCH₃ | CH | |
| 361 | " | —CH₂CO₂CH₃ | H | OCH₃ | OCH₃ | CH | 192–200 |
| 362 | " | —CH₂SOCH₃ | H | OCH₃ | OCH₃ | CH | |
| 363 | " | —CH₂SO₂CH₃ | H | OCH₃ | OCH₃ | CH | |
| 364 | " | —CH₂—C₆H₅ | H | OCH₃ | OCH₃ | CH | 167–169 |

TABLE 8-continued $$Q-SO_2NHCN \begin{matrix} O \\ \| \\ \phantom{x} \\ R_8 \end{matrix} \begin{matrix} X \\ N \\ \diagup \\ A \\ N \\ \diagdown \\ Y \end{matrix} \quad (I)$$

| Comp. No. | Q Pyridone ring | R₁ | R₈ | X | Y | A | Physical properties (m.p.: °C.) |
|---|---|---|---|---|---|---|---|
| 365 | ![3-methyl-pyridone with N-R₁] | —CH₂—C₆H₅ | H | CH₃ | OCH₃ | N | 164–169 |
| 366 | " | —CH₂NHCH₃ | H | OCH₃ | OCH₃ | CH | |
| 367 | " | —CH₂N(CH₃)₂ | H | OCH₃ | OCH₃ | CH | |
| 368 | " | —CH₂CH₂CN | H | OCH₃ | OCH₃ | CH | |
| 369 | " | —CH=CH₂ | H | OCH₃ | OCH₃ | CH | |
| 370 | " | —CH₂CH=CH₂ | H | OCH₃ | OCH₃ | CH | |
| 371 | " | —CH₂C=CH₂ $\|$ CH₃ | H | OCH₃ | OCH₃ | CH | |
| 372 | " | —CH₂CH=CCl₂ | H | OCH₃ | OCH₃ | CH | |
| 373 | " | —CH₂CH=CF₂ | H | OCH₃ | OCH₃ | CH | |
| 374 | " | —C≡CH | H | OCH₃ | OCH₃ | CH | |
| 375 | " | —CH₂C≡CH | H | OCH₃ | OCH₃ | CH | |
| 376 | " | —COCH₃ | H | OCH₃ | OCH₃ | CH | |
| 377 | " | —CO₂CH₃ | H | OCH₃ | OCH₃ | CH | 160–172 |
| 378 | " | —CH₂CO₂CH₃ | H | OCH₃ | OCH₃ | CH | |
| 379 | " | —SOCH₃ | H | OCH₃ | OCH₃ | CH | |
| 380 | " | —SO₂CH₃ | H | OCH₃ | OCH₃ | CH | |
| 381 | " | —NH₂ | H | OCH₃ | OCH₃ | CH | |
| 382 | " | —NHCH₃ | H | OCH₃ | OCH₃ | CH | |
| 383 | ![3-methyl-pyridone with N-R₁] | —N(CH₃)₂ | H | OCH₃ | OCH₃ | CH | |
| 384 | " | —NHSOCH₃ | H | OCH₃ | OCH₃ | CH | |
| 385 | " | —N—SO₂CH₃ $\|$ CH₃ | H | OCH₃ | OCH₃ | CH | |
| 386 | " | —N—COC₂H₅ $\|$ CH₃ | H | OCH₃ | OCH₃ | CH | |
| 387 | " | —CONH₂ | H | OCH₃ | OCH₃ | CH | |
| 388 | " | —CONHCH₃ | H | OCH₃ | OCH₃ | CH | |
| 389 | " | —CON(CH₃)₂ | H | OCH₃ | OCH₃ | CH | 147 decomposed |
| 390 | " | —SO₂NHCH₃ | H | OCH₃ | OCH₃ | CH | |
| 391 | " | —SO₂N(CH₃)₂ | H | OCH₃ | OCH₃ | CH | |
| 392 | " | —SO₂N—COCH₃ $\|$ CH₃ | H | OCH₃ | OCH₃ | CH | |
| 393 | " | —SO₂N—CO₂CH₃ $\|$ C₂H₅ | H | OCH₃ | OCH₃ | CH | |

TABLE 8-continued

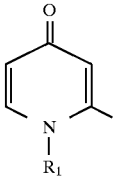

| Comp. No. | Q Pyridone ring | R₁ | R₈ | X | Y | A | Physical properties (m.p.: °C.) |
|---|---|---|---|---|---|---|---|
| 394 | 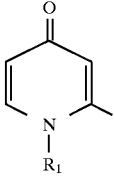 | H | H | OCH₃ | OCH₃ | CH | |
| 395 | " | H | H | CH₃ | CH₃ | CH | |
| 396 | " | CH₃ | H | OCH₃ | OCH₃ | CH | |
| 397 | " | CH₃ | H | Cl | OCH₃ | CH | |
| 398 | " | CH₃ | H | CH₃ | CH₃ | CH | |
| 399 | " | CH₃ | H | CH₃ | OCH₃ | N | |
| 400 | " | CH₃ | H | OCHF₂ | OCHF₂ | CH | |
| 401 | " | CH₃ | H | NHCH₃ | OCH₃ | CH | |
| 402 | " | C₂H₅ | H | OCH₃ | OCH₃ | CH | |
| 403 | " | C₂H₅ | H | Cl | OCH₃ | CH | |
| 404 | " | C₂H₅ | H | CH₃ | CH₃ | CH | |
| 405 | " | C₂H₅ | H | CH₃ | OCH₃ | N | |
| 406 | " | C₂H₅ | H | OCH₃ | OCH₃ | N | |
| 407 | " | C₂H₅ | CH₃ | OCH₃ | OCH₃ | CH | |
| 408 | " | C₂H₅ | H | OCHF₂ | OCHF₂ | CH | |
| 409 | " | C₂H₅ | H | NHCH₃ | OCH₃ | CH | |
| 410 | " | C₂H₅ | H | CH₂OCH₃ | OCH₃ | CH | |
| 411 | " | C₂H₅ | H | CH(OCH₃)₂ | OCH₃ | CH | |
| 412 | " | n-C₃H₇ | H | OCH₃ | OCH₃ | CH | |
| 413 | (same pyridone ring shown) | n-C₃H₇ | H | Cl | OCH₃ | CH | |
| 414 | " | n-C₃H₇ | H | CH₃ | CH₃ | CH | |
| 415 | " | n-C₃H₇ | H | CH₃ | OCH₃ | N | |
| 416 | " | n-C₃H₇ | H | OCH₃ | OCH₃ | N | |
| 417 | " | n-C₃H₇ | CH₃ | OCH₃ | OCH₃ | CH | |
| 418 | " | n-C₃H₇ | H | OCHF₂ | OCHF₂ | CH | |
| 419 | " | n-C₃H₇ | H | NHCH₃ | OCH₃ | CH | |
| 420 | " | iso-C₃H₇ | H | OCH₃ | OCH₃ | CH | |
| 421 | " | n-C₄H₉ | H | OCH₃ | OCH₃ | CH | |
| 422 | " | sec-C₄H₉ | H | OCH₃ | OCH₃ | CH | |
| 423 | " | tert-C₄H₉ | H | OCH₃ | OCH₃ | CH | |
| 424 | " | n-C₅H₁₁ | H | OCH₃ | OCH₃ | CH | |
| 425 | " | n-C₆H₁₃ | H | OCH₃ | OCH₃ | CH | |
| 426 | " | —CH₂Cl | H | OCH₃ | OCH₃ | CH | |
| 427 | " | —CHCl₂ | H | OCH₃ | OCH₃ | CH | |
| 428 | " | —CH₂CH₂Cl | H | OCH₃ | OCH₃ | CH | |
| 429 | " | —(CH₂)₃Cl | H | OCH₃ | OCH₃ | CH | |
| 430 | " | —CH(Cl)CH₃ | H | OCH₃ | OCH₃ | CH | |
| 431 | " | —CH₂CH(Cl)CH₃ | H | OCH₃ | OCH₃ | CH | |

TABLE 8-continued

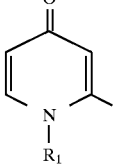

|  | Q | | | | | | Physical |
|---|---|---|---|---|---|---|---|
| Comp. No. | Pyridone ring | $R_1$ | $R_8$ | X | Y | A | properties (m.p.: °C.) |
| 432 | 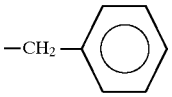 | —$CH_2F$ | H | $OCH_3$ | $OCH_3$ | CH | |
| 433 | " | —$CHF_2$ | H | $OCH_3$ | $OCH_3$ | CH | |
| 434 | " | —$CF_3$ | H | $OCH_3$ | $OCH_3$ | CH | |
| 435 | " | —$(CH_2)_3F$ | H | $OCH_3$ | $OCH_3$ | CH | |
| 436 | " | —$CH_2OCH_3$ | H | $OCH_3$ | $OCH_3$ | CH | |
| 437 | " | —$CH_2OCH_2CH_3$ | H | $OCH_3$ | $OCH_3$ | CH | |
| 438 | " | —$(CH_2)_2OCH_3$ | H | $OCH_3$ | $OCH_3$ | CH | |
| 439 | " | —$CH_2SCH_3$ | H | $OCH_3$ | $OCH_3$ | CH | |
| 440 | " | —$(CH_2)_2SCH_3$ | H | $OCH_3$ | $OCH_3$ | CH | |
| 441 | " | —$CH_2COCH_3$ | H | $OCH_3$ | $OCH_3$ | CH | |
| 442 | " | —$CH_2CO_2CH_3$ | H | $OCH_3$ | $OCH_3$ | CH | |
| 443 | " | —$CH_2SOCH_3$ | H | $OCH_3$ | $OCH_3$ | CH | |
| 444 | " | —$CH_2SO_2CH_3$ | H | $OCH_3$ | $OCH_3$ | CH | |
| 445 | " | —$CH_2$—Ph | H | $OCH_3$ | $OCH_3$ | CH | |
| 446 | " | —$CH_2$—Ph | H | $CH_3$ | $OCH_3$ | N | |
| 447 | " | —$CH_2NHCH_3$ | H | $OCH_3$ | $OCH_3$ | CH | |
| 448 | " | —$CH_2N(CH_3)_2$ | H | $OCH_3$ | $OCH_3$ | CH | |
| 449 | 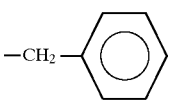 | —$CH_2CH_2CN$ | H | $OCH_3$ | $OCH_3$ | CH | |
| 450 | " | —$CH=CH_2$ | H | $OCH_3$ | $OCH_3$ | CH | |
| 451 | " | —$CH_2CH=CH_2$ | H | $OCH_3$ | $OCH_3$ | CH | |
| 452 | " | —$CH_2C(CH_3)=CH_2$ | H | $OCH_3$ | $OCH_3$ | CH | |
| 453 | " | —$CH_2CH=CCl_2$ | H | $OCH_3$ | $OCH_3$ | CH | |
| 454 | " | —$CH_2CH=CF_2$ | H | $OCH_3$ | $OCH_3$ | CH | |
| 455 | " | —$C\equiv CH$ | H | $OCH_3$ | $OCH_3$ | CH | |
| 456 | " | —$CH_2C\equiv CH$ | H | $OCH_3$ | $OCH_3$ | CH | |
| 457 | " | —$COCH_3$ | H | $OCH_3$ | $OCH_3$ | CH | |
| 458 | " | —$CO_2CH_3$ | H | $OCH_3$ | $OCH_3$ | CH | |
| 459 | " | —$CH_2CO_2CH_3$ | H | $OCH_3$ | $OCH_3$ | CH | |
| 460 | " | —$SOCH_3$ | H | $OCH_3$ | $OCH_3$ | CH | |
| 461 | " | —$SO_2CH_3$ | H | $OCH_3$ | $OCH_3$ | CH | |
| 462 | " | —$NH_2$ | H | $OCH_3$ | $OCH_3$ | CH | |
| 463 | " | —$NHCH_3$ | H | $OCH_3$ | $OCH_3$ | CH | |

TABLE 8-continued

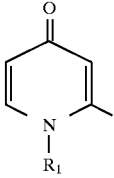

| Comp. No. | Q Pyridone ring | R₁ | R₈ | X | Y | A | Physical properties (m.p.: °C.) |
|---|---|---|---|---|---|---|---|
| 464 | " | —N(CH₃)₂ | H | OCH₃ | OCH₃ | CH | |
| 465 | " | —NHSOCH₃ | H | OCH₃ | OCH₃ | CH | |
| 466 | (pyridone) | —N(CH₃)—SO₂CH₃ | H | OCH₃ | OCH₃ | CH | |
| 467 | " | —N(CH₃)—COC₂H₅ | H | OCH₃ | OCH₃ | CH | |
| 468 | " | —CONH₂ | H | OCH₃ | OCH₃ | CH | |
| 469 | " | —CONHCH₃ | H | OCH₃ | OCH₃ | CH | |
| 470 | " | —CON(CH₃)₂ | H | OCH₃ | OCH₃ | CH | |
| 471 | " | —SO₂NHCH₃ | H | OCH₃ | OCH₃ | CH | |
| 472 | " | —SO₂N(CH₃)₂ | H | OCH₃ | OCH₃ | CH | |
| 473 | " | —SO₂N(CH₃)—COCH₃ | H | OCH₃ | OCH₃ | CH | |
| 474 | " | —SO₂N(C₂H₅)—CO₂CH₃ | H | OCH₃ | OCH₃ | CH | |

TABLE 9

Q = pyridone ring with (G)ₙ, R₁

| Comp. No. | (G)ₙ | R₁ | R₈ | X | Y | A | Physical properties (m.p.: °C.) |
|---|---|---|---|---|---|---|---|
| 475 | 4-Cl | H | H | OCH₃ | OCH₃ | CH | |
| 476 | 5-CH₃ | H | H | OCH₃ | OCH₃ | CH | |
| 477 | 6-OCH₂CH₃ | H | H | OCH₃ | OCH₃ | CH | |
| 478 | 4-CON(CH₃)₂ | H | H | OCH₃ | OCH₃ | CH | 201–204 |
| 479 | 5-Br | CH₃ | H | OCH₃ | OCH₃ | CH | |
| 480 | 4-C₂H₅ | CH₃ | H | OCH₃ | OCH₃ | CH | |
| 481 | 6-CF₃ | CH₃ | H | OCH₃ | OCH₃ | CH | 202–207 |
| 482 | 6-CF₃ | CH₃ | H | CH₃ | OCH₃ | N | |
| 483 | 5-CH₂OCH₂CH₃ | CH₃ | H | CH₃ | CH₃ | CH | |
| 484 | 4-CH₂COCH₃ | CH₃ | H | OCH₃ | OCH₃ | CH | |
| 485 | 4-OCH₃ | CH₃ | H | OCH₃ | OCH₃ | CH | 196–198 |
| 486 | 4-OCH₂CH₃ | CH₃ | H | OCH₃ | OCH₃ | CH | 147–149 |
| 487 | 4-SCH₃ | CH₃ | H | OCH₃ | OCH₃ | CH | 220–223 |
| 488 | 5-SO₂CH₃ | CH₃ | H | OCH₃ | OCH₃ | CH | |
| 489 | 6-Cl | C₂H₅ | H | OCH₃ | OCH₃ | CH | |
| 490 | 6-CH₃ | C₂H₅ | H | NHCH₃ | OCH₃ | CH | |
| 491 | 4-CH₂CO₂CH₃ | C₂H₅ | H | Cl | OCH₃ | CH | |
| 492 | 4-CO₂CO₂CH₃ | C₂H₅ | H | CH₃ | CH₃ | CH | |

TABLE 9-continued

Q = [pyridinone structure with (G)n at position 4, CH3 at position 3, =O at position 2, R1 on N at position 1]

| Comp. No. | (G)n | R₁ | R₈ | X | Y | A | Physical properties (m.p.: °C.) |
|---|---|---|---|---|---|---|---|
| 493 | 4-CH₂-C₆H₄-4-CH₃ | C₂H₅ | H | OCH₃ | OCH₃ | CH | |
| 494 | 4-CH₂OCH₂-(3-CH₃,4-CH₃)C₆H₃ | C₂H₅ | H | OCH₃ | OCH₃ | CH | |
| 495 | 4-OCH₃ | C₂H₅ | H | OCH₃ | OCH₃ | CH | 200–201 |
| 496 | 4-OCH₂CH₃ | C₂H₅ | H | OCH₃ | OCH₃ | CH | 168–171 |
| 497 | 4-SCH₃ | C₂H₅ | H | OCH₃ | OCH₃ | CH | 204–205 |
| 498 | 4-N(CH₃)₂ | C₂H₅ | H | OCHF₂ | OCHF₂ | CH | |
| 499 | 4-N(SO₂CH₃)(CH₃) | C₂H₅ | H | OCH₃ | OCH₃ | CH | |
| 500 | 4-CON(CH₃)₂ | C₂H₅ | H | NHCH₃ | OCH₃ | CH | |
| 501 | 4-SO₂N(CH₃)₂ | C₂H₅ | H | OCH₃ | OCH₃ | CH | |
| 502 | 5-Cl | n-C₃H₇ | H | OCH₃ | OCH₃ | CH | 199–205 |
| 503 | 5-Br | n-C₃H₇ | H | OCH₃ | OCH₃ | CH | 200–210 |
| 504 | 4,6-F₂ | n-C₃H₇ | H | OCH₃ | OCH₃ | CH | |
| 505 | 5-Cl | n-C₃H₇ | H | CH₃ | OCH₃ | N | |
| 506 | 4-CH₃ | n-C₃H₇ | H | OCH₃ | OCH₃ | CH | 185–188 |
| 507 | 4-C₃H₇(n) | n-C₃H₇ | CH₃ | OCH₃ | OCH₃ | CH | |
| 508 | 4,6-(CH₃)₂ | n-C₃H₇ | H | OCH₃ | OCH₃ | CH | |
| 509 | 4-CF₃ | n-C₃H₇ | H | OCH₃ | OCH₃ | CH | 142–144 |
| 510 | 5-CF₃ | n-C₃H₇ | H | OCH₃ | OCH₃ | CH | 197–202 |
| 511 | 4-CH₂OCH₃ | n-C₃H₇ | H | OCH₃ | OCH₃ | CH | |
| 512 | 4-CH₂SCH₃ | n-C₃H₇ | H | OCH₃ | OCH₃ | CH | |
| 513 | 4-CH₂CO₂CH₃ | n-C₃H₇ | H | OCH₃ | OCH₃ | CH | |
| 514 | 4-CH₂SO₂CH₃ | n-C₃H₇ | H | OCH₃ | OCH₃ | CH | |
| 515 | 4-CH₂-(2-Cl,4-Cl)C₆H₃ | n-C₃H₇ | H | OCH₃ | OCH₃ | CH | |
| 516 | 4-CH₂N(CH₃)₂ | n-C₃H₇ | H | OCH₃ | OCH₃ | CH | |
| 517 | 4-OCH₃ | n-C₃H₇ | H | OCH₃ | OCH₃ | CH | 175–178 |
| 518 | 4-OCH₃ | n-C₃H₇ | H | Cl | OCH₃ | CH | |
| 519 | 4-OCH₃ | n-C₃H₇ | H | CH₃ | OCH₃ | N | |
| 520 | 4-OCH₃ | n-C₃H₇ | H | OCHF₂ | OCHF₂ | CH | |
| 521 | 4-OCH₂CH₃ | n-C₃H₇ | H | OCH₃ | OCH₃ | CH | 108–111 |
| 522 | 4-OCH₂CH₂CH₃ | n-C₃H₇ | H | OCH₃ | OCH₃ | CH | 100–105 |
| 523 | 4-OCH(CH₃)₂ | n-C₃H₇ | H | OCH₃ | OCH₃ | CH | 130–135 |
| 524 | 4-OCH₂CH₂F | n-C₃H₇ | H | OCH₃ | OCH₃ | CH | |
| 525 | 4-OCH₂CHF₂ | n-C₃H₇ | H | OCH₃ | OCH₃ | CH | |
| 526 | 4-OCH₂CF₃ | n-C₃H₇ | H | OCH₃ | OCH₃ | CH | 158–160 |
| 527 | 4-SCH₃ | n-C₃H₇ | H | OCH₃ | OCH₃ | CH | 194–198 |
| 528 | 4-SCH₂CH₃ | n-C₃H₇ | H | OCH₃ | OCH₃ | CH | 108–110 |
| 529 | 4-CO₂CH₃ | n-C₃H₇ | H | OCH₃ | OCH₃ | CH | |
| 530 | 4-SO₂CH₃ | n-C₃H₇ | H | OCH₃ | OCH₃ | CH | |
| 531 | 4-NHCH₃ | n-C₃H₇ | H | OCH₃ | OCH₃ | CH | 142–145 |
| 532 | 4-N(SO₂CH₃)(CH₃) | n-C₃H₇ | H | OCH₃ | OCH₃ | CH | |
| 533 | 4-N(COC₂H₅)(CH₃) | n-C₃H₇ | H | OCH₃ | OCH₃ | CH | |

TABLE 9-continued

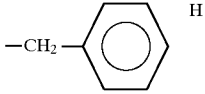

| Comp. No. | (G)$_n$ | R$_1$ | R$_8$ | X | Y | A | Physical properties (m.p.: °C.) |
|---|---|---|---|---|---|---|---|
| 534 | 4-CON(CH$_3$)$_2$ | n-C$_3$H$_7$ | H | OCH$_3$ | OCH$_3$ | CH | 175–180 |
| 535 | 4-SO$_2$N(CH$_3$)$_2$ | n-C$_3$H$_7$ | H | OCH$_3$ | OCH$_3$ | CH | |
| 536 | 4-SO$_2$N—CO$_2$CH$_3$<br>        \|<br>        C$_2$H$_5$ | n-C$_3$H$_7$ | H | OCH$_3$ | OCH$_3$ | CH | |
| 537 | 5-Cl | iso-C$_3$H$_7$ | H | OCH$_3$ | OCH$_3$ | CH | |
| 538 | 4-CH$_3$ | iso-C$_3$H$_7$ | H | OCH$_3$ | OCH$_3$ | CH | |
| 539 | 4-OCH$_3$ | iso-C$_3$H$_7$ | H | OCH$_3$ | OCH$_3$ | CH | 187–189 |
| 540 | 4-OCH$_2$CH$_3$ | iso-C$_3$H$_7$ | H | OCH$_3$ | OCH$_3$ | CH | 100–102 |
| 541 | 4-SCH$_3$ | iso-C$_3$H$_7$ | H | OCH$_3$ | OCH$_3$ | CH | 193–194 |
| 542 | 5-Br | —CH$_2$CH$_2$Cl | H | OCH$_3$ | OCH$_3$ | CH | |
| 543 | 4-CH$_3$ | —CF$_3$ | H | OCH$_3$ | OCH$_3$ | CH | |
| 544 | 5-Br | —CH$_2$OCH$_3$ | H | OCH$_3$ | OCH$_3$ | CH | |
| 545 | 4-OCH$_3$ | —CH$_2$OCH$_3$ | H | OCH$_3$ | OCH$_3$ | CH | 200–203 |
| 546 | 4-OCH$_2$CH$_3$ | —CH$_2$OCH$_3$ | H | OCH$_3$ | OCH$_3$ | CH | 166–167 |
| 547 | 4-SCH$_3$ | —CH$_2$OCH$_3$ | H | OCH$_3$ | OCH$_3$ | CH | |
| 548 | 4-CO$_2$CH$_3$ | —CH$_2$OCH$_3$ | H | OCH$_3$ | OCH$_3$ | CH | |
| 549 | 4-SO$_2$CH$_3$ | —CH$_2$OCH$_3$ | H | OCH$_3$ | OCH$_3$ | CH | |
| 550 | 4-NHCH$_3$ | —CH$_2$OCH$_3$ | H | OCH$_3$ | OCH$_3$ | CH | |
| 551 | 4-N—SO$_2$CH$_3$<br>   \|<br>   CH$_3$ | —CH$_2$OCH$_3$ | H | OCH$_3$ | OCH$_3$ | CH | |
| 552 | 4-N—COC$_2$H$_5$<br>   \|<br>   CH$_3$ | —CH$_2$OCH$_3$ | H | OCH$_3$ | OCH$_3$ | CH | |
| 553 | 4-CON(CH$_3$)$_2$ | —CH$_2$OCH$_3$ | H | OCH$_3$ | OCH$_3$ | CH | 193–195 |
| 554 | 4-SO$_2$N(CH$_3$)$_2$ | —CH$_2$OCH$_3$ | H | OCH$_3$ | OCH$_3$ | CH | |
| 555 | 4-OCH$_2$CH$_3$ | —CO$_2$SCH$_3$ | H | OCH$_3$ | OCH$_3$ | CH | |
| 556 | 4-SCH$_3$ | —CH$_2$CO$_2$CH$_3$ | H | OCH$_3$ | OCH$_3$ | CH | |
| 557 | 4-NHCH$_3$ | —CH$_2$SO$_2$CH$_3$ | H | OCH$_3$ | OCH$_3$ | CH | |
| 558 | 4-CON(CH$_3$)$_2$ | —CH$_2$—C$_6$H$_5$ | H | OCH$_3$ | OCH$_3$ | CH | |
| 559 | 4-OCH$_3$ | CH$_2$N(CH$_3$)$_2$ | H | OCH$_3$ | OCH$_3$ | CH | |
| 560 | 4-OCH$_3$ | —CH$_2$CH=CH$_2$ | H | OCH$_3$ | OCH$_3$ | CH | 195–196 |
| 561 | 4-OCH$_2$CH$_3$ | —CH$_2$CH=CH$_2$ | H | OCH$_3$ | OCH$_3$ | CH | 149–152 |
| 562 | 4-SCH$_3$ | —CH$_2$CH=CH$_2$ | H | OCH$_3$ | OCH$_3$ | CH | 202–204 |
| 563 | 4-CON(CH$_3$)$_2$ | —CH$_2$CH=CH$_2$ | H | OCH$_3$ | OCH$_3$ | CH | 185–187 |
| 564 | 4-OCH$_3$ | —OCH$_2$CH$_3$ | H | OCH$_3$ | OCH$_3$ | CH | |
| 565 | 4-OCH$_2$CH$_3$ | —CO$_2$CH$_3$ | H | OCH$_3$ | OCH$_3$ | CH | |
| 566 | 4-OCH$_3$ | —SO$_2$CH$_3$ | H | OCH$_3$ | OCH$_3$ | CH | |
| 567 | 4-OCH$_3$ | —N(CH$_3$)$_2$ | H | OCH$_3$ | OCH$_3$ | CH | |
| 568 | 4-OCH$_2$CH$_3$ | —N—SO$_2$CH$_3$<br>   \|<br>   CH$_3$ | H | OCH$_3$ | OCH$_3$ | CH | |
| 569 | 4-OCH$_3$ | —CON(CH$_3$)$_2$ | H | OCH$_3$ | OCH$_3$ | CH | |
| 570 | 4-OCH$_2$CH$_3$ | —SO$_2$N(CH$_3$)$_2$ | H | OCH$_3$ | OCH$_3$ | CH | |
| 571 | 4-OCH$_2$CH$_3$ | SO$_2$N—CO$_2$CH$_3$<br>   \|<br>   C$_2$H$_5$ | H | OCH$_3$ | OCH$_3$ | CH | |

TABLE 10

Q = 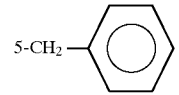

| Comp. No. | (G)$_n$ | R$_1$ | R$_8$ | X | Y | A | Physical properties (m.p.: °C.) |
|---|---|---|---|---|---|---|---|
| 572 | 5-Cl | H | H | OCH$_3$ | OCH$_3$ | CH | |
| 573 | 5-C$_2$H$_5$ | CH$_3$ | H | OCH$_3$ | OCH$_3$ | CH | |
| 574 | 3-OCH$_3$ | CH$_3$ | H | OCH$_3$ | OCH$_3$ | CH | |
| 575 | 3-SCH$_3$ | CH$_3$ | H | OCH$_3$ | OCH$_3$ | CH | |
| 576 | 6-CH$_2$CO$_2$CH$_3$ | C$_2$H$_5$ | H | Cl | OCH$_3$ | CH | |
| 577 | 6-CH$_2$SO$_2$CH$_3$ | C$_2$H$_5$ | H | CH$_3$ | CH$_3$ | CH | |
| 578 | 5,6-F$_2$ | n-C$_3$H$_7$ | H | OCH$_3$ | OCH$_3$ | CH | |
| 579 | 5-CF$_3$ | n-C$_3$H$_7$ | H | CH$_3$ | OCH$_3$ | N | |
| 580 | 5-CH$_2$OCH$_3$ | n-C$_3$H$_7$ | H | OCH$_3$ | OCH$_3$ | CH | |
| 581 | 5-CH$_2$SCH$_3$ | n-C$_3$H$_7$ | H | OCH$_3$ | OCH$_3$ | CH | |
| 582 | 5-CH$_2$—C$_6$H$_5$ | n-C$_3$H$_7$ | H | OCH$_3$ | OCH$_3$ | CH | |
| 583 | 5-CH$_2$N(CH$_3$)$_2$ | n-C$_3$H$_7$ | H | OCH$_3$ | OCH$_3$ | CH | |
| 584 | 5-SO$_2$CH$_3$ | n-C$_3$H$_7$ | H | OCH$_3$ | OCH$_3$ | CH | |
| 585 | 5-NHCH$_3$ | n-C$_3$H$_7$ | H | OCH$_3$ | OCH$_3$ | CH | |
| 586 | 5-CON(CH$_3$)$_2$ | n-C$_3$H$_7$ | H | OCH$_3$ | OCH$_3$ | CH | |
| 587 | 5-OCH$_3$ | iso-C$_3$H$_7$ | H | OCH$_3$ | OCH$_3$ | CH | |
| 588 | 5-Br | —CH$_2$CH$_2$Cl | H | OCH$_3$ | OCH$_3$ | CH | |
| 589 | 5-Br | —CH$_2$OCH$_3$ | H | OCH$_3$ | OCH$_3$ | CH | |
| 590 | 5-CO$_2$CH$_3$ | —CH$_2$OCH$_3$ | H | OCH$_3$ | OCH$_3$ | CH | |
| 591 | 5-N(SO$_2$CH$_3$)CH$_3$ | —CH$_2$OCH$_3$ | H | OCH$_3$ | OCH$_3$ | CH | |
| 592 | 5-N(COC$_2$H$_5$)CH$_3$ | —CH$_2$OCH$_3$ | H | OCH$_3$ | OCH$_3$ | CH | |
| 593 | 6-SO$_2$N(CH$_3$)$_2$ | —CH$_2$OCH$_3$ | H | OCH$_3$ | OCH$_3$ | CH | |
| 594 | 6-OCH$_2$CH$_3$ | —CH$_2$SCH$_3$ | H | OCH$_3$ | OCH$_3$ | CH | |
| 595 | 5-SCH$_3$ | —CH$_2$CO$_2$CH$_3$ | H | OCH$_3$ | OCH$_3$ | CH | |
| 596 | 5-NHCH$_3$ | —CH$_2$SO$_2$CH$_3$ | H | OCH$_3$ | OCH$_3$ | CH | |
| 597 | 5-CON(CH$_3$)$_2$ | —CH$_2$—C$_6$H$_5$ | H | OCH$_3$ | OCH$_3$ | CH | |
| 598 | 5-OCH$_3$ | —CH$_2$N(CH$_3$)$_2$ | H | OCH$_3$ | OCH$_3$ | CH | |
| 599 | 5-OCH$_3$ | —CH$_2$CH=CH$_2$ | H | OCH$_3$ | OCH$_3$ | CH | |
| 600 | 5-OCH$_3$ | —OCH$_2$CH$_3$ | H | OCH$_3$ | OCH$_3$ | CH | |
| 601 | 5-OCH$_2$CH$_3$ | —CO$_2$CH$_3$ | H | OCH$_3$ | OCH$_3$ | CH | |
| 602 | 5-OCH$_3$ | —SO$_2$CH$_3$ | H | OCH$_3$ | OCH$_3$ | CH | |
| 603 | 5-OCH$_3$ | —N(CH$_3$)$_2$ | H | OCH$_3$ | OCH$_3$ | CH | |
| 604 | 5-OCH$_3$ | —CON(CH$_3$)$_2$ | H | OCH$_3$ | OCH$_3$ | CH | |
| 605 | 5-OCH$_2$CH$_3$ | —SO$_2$N(CH$_3$)$_2$ | H | OCH | OCH | CH | |

TABLE 11

Q = 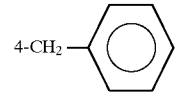

| Comp. No. | (G)n | R₁ | R₈ | X | Y | A | Physical properties (m.p.: °C.) |
|---|---|---|---|---|---|---|---|
| 606 | 4-Cl | H | H | OCH₃ | OCH₃ | CH | |
| 607 | 4-C₂H₅ | CH₃ | H | OCH₃ | OCH₃ | CH | |
| 608 | 4-OCH₃ | CH₃ | H | OCH₃ | OCH₃ | CH | |
| 609 | 4-SCH₃ | CH₃ | H | OCH₃ | OCH₃ | CH | |
| 610 | 4-CH₂CO₂CH₃ | C₂H₅ | H | Cl | OCH₃ | CH | |
| 611 | 4-CH₂SO₂CH₃ | C₂H₅ | H | CH₃ | CH₃ | CH | |
| 612 | 4,6-F₂ | n-C₃H₇ | H | OCH₃ | OCH₃ | CH | |
| 613 | 3-CF₃ | n-C₃H₇ | H | CH₃ | OCH₃ | N | |
| 614 | 4-CH₂OCH₃ | n-C₃H₇ | H | OCH₃ | OCH₃ | CH | |
| 615 | 4-CH₂SCH₃ | n-C₃H₇ | H | OCH₃ | OCH₃ | CH | |
| 616 | 4-CH₂—C₆H₅ | n-C₃H₇ | H | OCH₃ | OCH₃ | CH | |
| 617 | 4-CH₂N(CH₃)₂ | n-C₃H₇ | H | OCH₃ | OCH₃ | CH | |
| 618 | 4-SO₂CH₃ | n-C₃H₇ | H | OCH₃ | OCH₃ | CH | |
| 619 | 4-NHCH₃ | n-C₃H₇ | H | OCH₃ | OCH₃ | CH | |
| 620 | 4-CON(CH₃)₂ | n-C₃H₇ | H | OCH₃ | OCH₃ | CH | |
| 621 | 4-OCH₃ | iso-C₃H₇ | H | OCH₃ | OCH₃ | CH | |
| 622 | 3-Br | —CH₂CH₂Cl | H | OCH₃ | OCH₃ | CH | |
| 623 | 3-Br | —CH₂OCH₃ | H | OCH₃ | OCH₃ | CH | |
| 624 | 4-CO₂CH₃ | —CH₂OCH₃ | H | OCH₃ | OCH₃ | CH | |
| 625 | 4-N(CH₃)—SO₂CH₃ | —CH₂OCH₃ | H | OCH₃ | OCH₃ | CH | |
| 626 | 4-N(CH₃)—COC₂H₅ | —CH₂OCH₃ | H | OCH₃ | OCH₃ | CH | |
| 627 | 4-SO₂N(CH₃)₂ | —CH₂OCH₃ | H | OCH₃ | OCH₃ | CH | |
| 628 | 4-OCH₂CH₃ | —CH₂SCH₃ | H | OCH₃ | OCH₃ | CH | |
| 629 | 4-SCH₃ | —CH₂CO₂CH₃ | H | OCH₃ | OCH₃ | CH | |
| 630 | 4-NHCH₃ | —CH₂SO₂CH₃ | H | OCH₃ | OCH₃ | CH | |
| 631 | 4-CON(CH₃)₂ | —CH₂—C₆H₅ | H | OCH₃ | OCH₃ | CH | |
| 632 | 4-OCH₃ | —CH₂N(CH₃)₂ | H | OCH₃ | OCH₃ | CH | |
| 633 | 4-OCH₃ | —CH₂CH=CH₂ | H | OCH₃ | OCH₃ | CH | |
| 634 | 4-OCH₃ | —OCH₂CH₃ | H | OCH₃ | OCH₃ | CH | |
| 635 | 4-OCH₂CH₃ | —CO₂CH₃ | H | OCH₃ | OCH₃ | CH | |
| 636 | 4-OCH₃ | —SO₂CH₃ | H | OCH₃ | OCH₃ | CH | |
| 637 | 4-OCH₃ | —N(CH₃)₂ | H | OCH₃ | OCH₃ | CH | |
| 638 | 4-OCH₃ | —CON(CH₃)₂ | H | OCH₃ | OCH₃ | CH | |
| 639 | 4-OCH₂CH₃ | —SO₂N(CH₃)₂ | H | OCH₃ | OCH₃ | CH | |

TABLE 12

Q = [structure: 6-membered ring with (G)n substituent, N-R1, C=O at position 2]

| Comp. No. | (G)n | R₁ | R₈ | X | Y | A | Physical properties (m.p.: °C.) |
|---|---|---|---|---|---|---|---|
| 640 | 4-Cl | H | H | OCH₃ | OCH₃ | CH | |
| 641 | 4-C₂H₅ | CH₃ | H | OCH₃ | OCH₃ | CH | |
| 642 | 4-OCH₃ | CH₃ | H | OCH₃ | OCH₃ | CH | |
| 643 | 4-SCH₃ | CH₃ | H | OCH₃ | OCH₃ | CH | |
| 644 | 4-CH₂CO₂CH₃ | C₂H₅ | H | Cl | OCH₃ | CH | |
| 645 | 4-CH₂SO₂CH₃ | C₂H₅ | H | CH₃ | CH₃ | CH | |
| 646 | 4,5-F₂ | n-C₃H₇ | H | OCH₃ | OCH₃ | CH | |
| 647 | 5-CF₃ | n-C₃H₇ | H | CH₃ | OCH₃ | N | |
| 648 | 4-CH₂OCH₃ | n-C₃H₇ | H | OCH₃ | OCH₃ | CH | |
| 649 | 4-CH₂SCH₃ | n-C₃H₇ | H | OCH₃ | OCH₃ | CH | |
| 650 | 4-CH₂-C₆H₅ | n-C₃H₇ | H | OCH₃ | OCH₃ | CH | |
| 651 | 4-CH₂N(CH₃)₂ | n-C₃H₇ | H | OCH₃ | OCH₃ | CH | |
| 652 | 4-SO₂CH₃ | n-C₃H₇ | H | OCH₃ | OCH₃ | CH | |
| 653 | 4-NHCH₃ | n-C₃H₇ | H | OCH₃ | OCH₃ | CH | |
| 654 | 4-CON(CH₃)₂ | n-C₃H₇ | H | OCH₃ | OCH₃ | CH | |
| 655 | 4-OCH₃ | iso-C₃H₇ | H | OCH₃ | OCH₃ | CH | |
| 656 | 5-Br | —CH₂CH₂Cl | H | OCH₃ | OCH₃ | CH | |
| 657 | 5-Br | —CH₂OCH₃ | H | OCH₃ | OCH₃ | CH | |
| 658 | 4-CO₂CH₃ | —CH₂OCH₃ | H | OCH₃ | OCH₃ | CH | |
| 659 | 4-N(CH₃)—SO₂CH₃ | —CH₂OCH₃ | H | OCH₃ | OCH₃ | CH | |
| 660 | 4-N(CH₃)—COC₂H₅ | —CH₂OCH₃ | H | OCH₃ | OCH₃ | CH | |
| 661 | 4-SO₂N(CH₃)₂ | —CH₂OCH₃ | H | OCH₃ | OCH₃ | CH | |
| 662 | 4-OCH₂CH₃ | —CH₂SCH₃ | H | OCH₃ | OCH₃ | CH | |
| 663 | 4-SCH₃ | —CH₂CO₂CH₃ | H | OCH₃ | OCH₃ | CH | |
| 664 | 4-NHCH₃ | —CH₂SO₂CH₃ | H | OCH₃ | OCH₃ | CH | |
| 665 | 4-CON(CH₃)₂ | —CH₂-C₆H₅ | H | OCH₃ | OCH₃ | CH | |
| 666 | 3-OCH₃ | —CH₂N(CH₃)₂ | H | OCH₃ | OCH₃ | CH | |
| 667 | 3-OCH₃ | —CH₂CH=CH₂ | H | OCH₃ | OCH₃ | CH | |
| 668 | 3-OCH₃ | —OCH₂CH₃ | H | OCH₃ | OCH₃ | CH | |
| 669 | 4-OCH₂CH₃ | —CO₂CH₃ | H | OCH₃ | OCH₃ | CH | |
| 670 | 4-OCH₃ | —SO₂CH₃ | H | OCH₃ | OCH₃ | CH | |
| 671 | 4-OCH₃ | —N(CH₃)₂ | H | OCH₃ | OCH₃ | CH | |
| 672 | 4-OCH₃ | —CON(CH₃)₂ | H | OCH₃ | OCH₃ | CH | |
| 673 | 4-OCH₂CH₃ | —SO₂N(CH₃)₂ | H | OCH₃ | OCH₃ | CH | |

TABLE 13

Q = (structure: pyridinone with (G)n at positions 5,6 and C4=O, C3-CH3, N1-R1)

| Comp. No. | (G)n | R1 | R8 | X | Y | A | Physical properties (m.p.: °C.) |
|---|---|---|---|---|---|---|---|
| 674 | 2-Cl | H | H | OCH3 | OCH3 | CH | 102–110 |
| 675 | 2-Cl | CH3 | H | OCH3 | OCH3 | CH | 137–143 |
| 676 | 2-Cl | CH3 | H | CH3 | OCH3 | N | 140–147 |
| 677 | 2-SCH3 | CH3 | H | OCH3 | OCH3 | CH | |
| 678 | 2-CH2CO2CH3 | C2H5 | H | Cl | OCH3 | CH | |
| 679 | 2-CH2SO2CH3 | C2H5 | H | CH3 | CH3 | CH | |
| 680 | 2-Cl | n-C3H7 | H | OCH3 | OCH3 | CH | 141–149 |
| 681 | 5,6-F2 | n-C3H7 | H | OCH3 | OCH3 | CH | |
| 682 | 5-CF3 | n-C3H7 | H | CH3 | OCH3 | N | |
| 683 | 2-CH2OCH3 | n-C3H7 | H | OCH3 | OCH3 | CH | |
| 684 | 2-CH2SCH3 | n-C3H7 | H | OCH3 | OCH3 | CH | |
| 685 | 2-CH2-C6H5 | n-C3H7 | H | OCH3 | OCH3 | CH | |
| 686 | 2-CH2N(CH3)2 | n-C3H7 | H | OCH3 | OCH3 | CH | |
| 687 | 2-SO2CH3 | n-C3H7 | H | OCH3 | OCH3 | CH | |
| 688 | 2-NHCH3 | n-C3H7 | H | OCH3 | OCH3 | CH | |
| 689 | 2-CON(CH3)2 | n-C3H7 | H | OCH3 | OCH3 | CH | |
| 690 | 2-OCH3 | iso-C3H7 | H | OCH3 | OCH3 | CH | |
| 691 | 5-Br | —CH2CH2Cl | H | OCH3 | OCH3 | CH | |
| 692 | 5-Br | —CH2OCH3 | H | OCH3 | OCH3 | CH | |
| 693 | 2-CO2CH3 | —CH2OCH3 | H | OCH3 | OCH3 | CH | |
| 694 | 2-N(CH3)—SO2CH3 | —CH2OCH3 | H | OCH3 | OCH3 | CH | |
| 695 | 2-N(CH3)—COC2H5 | —CH2OCH3 | H | OCH3 | OCH3 | CH | |
| 696 | 2-SO2N(CH3)2 | —CH2OCH3 | H | OCH3 | OCH3 | CH | |
| 697 | 2-OCH2CH3 | —CH2SCH3 | H | OCH3 | OCH3 | CH | |
| 698 | 2-SCH3 | —CH2CO2CH3 | H | OCH3 | OCH3 | CH | |
| 699 | 2-NHCH3 | —CH2SO2CH3 | H | OCH3 | OCH3 | CH | |
| 700 | 2-CON(CH3)2 | —CH2-C6H5 | H | OCH3 | OCH3 | CH | |
| 701 | 2-OCH3 | —CH2N(CH3)2 | H | OCH3 | OCH3 | CH | |
| 702 | 2-OCH3 | —CH2CH=CH2 | H | OCH3 | OCH3 | CH | |
| 703 | 2-OCH3 | —OCH2CH3 | H | OCH3 | OCH3 | CH | |
| 704 | 2-OCH2CH3 | —CO2CH3 | H | OCH3 | OCH3 | CH | |
| 705 | 2-OCH3 | —SO2CH3 | H | OCH3 | OCH3 | CH | |
| 706 | 2-OCH3 | —N(CH3)2 | H | OCH3 | OCH3 | CH | |
| 707 | 2-OCH3 | —CON(CH3)2 | H | OCH3 | OCH3 | CH | |
| 708 | 2-OCH2CH3 | —SO2N(CH3)2 | H | OCH3 | OCH3 | CH | |

TABLE 14

Q =

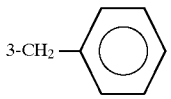

| Comp. No. | (G)$_n$ | R$_1$ | R$_8$ | X | Y | A | Physical properties (m.p.: °C.) |
|---|---|---|---|---|---|---|---|
| 709 | 3-Cl | H | H | OCH$_3$ | OCH$_3$ | CH | |
| 710 | 3-C$_2$H$_5$ | CH$_3$ | H | OCH$_3$ | OCH$_3$ | CH | |
| 711 | 3-OCH$_3$ | CH$_3$ | H | OCH$_3$ | OCH$_3$ | CH | |
| 712 | 3-SCH$_3$ | CH$_3$ | H | OCH$_3$ | OCH$_3$ | CH | |
| 713 | 3-CH$_2$CO$_2$CH$_3$ | C$_2$H$_5$ | H | Cl | OCH$_3$ | CH | |
| 714 | 5-CH$_2$SO$_2$CH$_3$ | C$_2$H$_5$ | H | CH$_3$ | CH$_3$ | CH | |
| 715 | 5,6-F$_2$ | n-C$_3$H$_7$ | H | OCH$_3$ | OCH$_3$ | CH | |
| 716 | 5-CF$_3$ | n-C$_3$H$_7$ | H | CH$_3$ | OCH$_3$ | N | |
| 717 | 6-CH$_2$OCH$_3$ | n-C$_3$H$_7$ | H | OCH$_3$ | OCH$_3$ | CH | |
| 718 | 6-CH$_2$SCH$_3$ | n-C$_3$H$_7$ | H | OCH$_3$ | OCH$_3$ | CH | |
| 719 | 3-CH$_2$—⟨Ph⟩ | n-C$_3$H$_7$ | H | OCH$_3$ | OCH$_3$ | CH | |
| 720 | 3-CH$_2$N(CH$_3$)$_2$ | n-C$_3$H$_7$ | H | OCH$_3$ | OCH$_3$ | CH | |
| 721 | 3-SO$_2$CH$_3$ | n-C$_3$H$_7$ | H | OCH$_3$ | OCH$_3$ | CH | |
| 722 | 3-NHCH$_3$ | n-C$_3$H$_7$ | H | OCH$_3$ | OCH$_3$ | CH | |
| 723 | 3-CON(CH$_3$)$_2$ | n-C$_3$H$_7$ | H | OCH$_3$ | OCH$_3$ | CH | |
| 724 | 3-OCH$_3$ | iso-C$_3$H$_7$ | H | OCH$_3$ | OCH$_3$ | CH | |
| 725 | 5-Br | —CH$_2$CH$_2$Cl | H | OCH$_3$ | OCH$_3$ | CH | |
| 726 | 5-Br | —CH$_2$OCH$_3$ | H | OCH$_3$ | OCH$_3$ | CH | |
| 727 | 3-CO$_2$CH$_3$ | —CH$_2$OCH$_3$ | H | OCH$_3$ | OCH$_3$ | CH | |
| 728 | 3-N(CH$_3$)—SO$_2$CH$_3$ | —CH$_2$OCH$_3$ | H | OCH$_3$ | OCH$_3$ | CH | |
| 729 | 3-N(CH$_3$)—COC$_2$H$_5$ | —CH$_2$OCH$_3$ | H | OCH$_3$ | OCH$_3$ | CH | |
| 730 | 3-SO$_2$N(CH$_3$)$_2$ | —CH$_2$OCH$_3$ | H | OCH$_3$ | OCH$_3$ | CH | |
| 731 | 3-OCH$_2$CH$_3$ | —CH$_2$SCH$_3$ | H | OCH$_3$ | OCH$_3$ | CH | |
| 732 | 3-SCH$_3$ | —CH$_2$CO$_2$CH$_3$ | H | OCH$_3$ | OCH$_3$ | CH | |
| 733 | 3-NHCH$_3$ | —CH$_2$SO$_2$CH$_3$ | H | OCH$_3$ | OCH$_3$ | CH | |
| 734 | 3-CON(CH$_3$)$_2$ | —CH$_2$—⟨Ph⟩ | H | OCH$_3$ | OCH$_3$ | CH | |
| 735 | 3-OCH$_3$ | —CH$_2$N(CH$_3$)$_2$ | H | OCH$_3$ | OCH$_3$ | CH | |
| 736 | 3-OCH$_3$ | —CH$_2$CH=CH$_2$ | H | OCH$_3$ | OCH$_3$ | CH | |
| 737 | 3-OCH$_3$ | —OCH$_2$CH$_3$ | H | OCH$_3$ | OCH$_3$ | CH | |
| 738 | 3-OCH$_2$CH$_3$ | —CO$_2$CH$_3$ | H | OCH$_3$ | OCH$_3$ | CH | |
| 739 | 3-OCH$_3$ | —SO$_2$CH$_3$ | H | OCH$_3$ | OCH$_3$ | CH | |
| 740 | 3-OCH$_3$ | —N(CH$_3$)$_2$ | H | OCH$_3$ | OCH$_3$ | CH | |
| 741 | 3-OCH$_3$ | —CON(CH$_3$)$_2$ | H | OCH$_3$ | OCH$_3$ | CH | |
| 742 | 3-OCH$_2$CH$_3$ | —SO$_2$N(CH$_3$)$_2$ | H | OCH$_3$ | OCH$_3$ | CH | |

Now, Test Examples of the present invention will be given.

TEST EXAMPLE 1

Upland field soil was put into a 1/150,000 ha pot, and seeds of various plants were sown. Then, when the plants reached predetermined leaf stages (①) barnyardgrass (*Echinochloa crus-galli* L.), EC: 1.7–2.5 leaf stage, ② crabgrass (*Digitaria sanguinalis* L.), DS: 1.0–2.2 leaf stage, ③ slender amaranth (*Amaranthus viridis* L.), AV: 0.1–1.0 leaf stage, ④ prickly sida (*Sida spinosa* L.), SS: 0.1–1.2 leaf stage, ⑤ tall morningglory (*Ipomoea purpurea* L.), IP: 0.2–2.0 leaf stage, ⑥ common cocklebur (*Xanthium strumarium* L.), XS: 0.3–1.8 leaf stage, ⑦ rice (*Oryza sativa* L.), OS: 1.2–2.2 leaf stage, ⑧ wheat (*Triticum* spp.), TR: 2.2–3.3 leaf stage, ⑨ corn (*Zea mays* L.), ZM: 2.2–3.4 leaf stage, ⑩ soybean (*Glycine max* Merr.), GM: primary leaf—0.2 leaf stage), a wettable powder having the compound of the present invention formulated in accordance with a usual formulation method, was weighed so that the active ingredient would be a predetermined amount, and diluted with water in an amount of 500 l/ha. To the diluted solution, 0.1% (v/v) of an agricultural spreader was added. The herbicide thus adjusted was applied by a small size spray for foliage treatment. On the 18th to 23rd days after the application of the herbicide, the growth of the respective plants was visually observed, and the herbicidal effects were evaluated by the growth-controlling degrees (%) ranging from 0 (equivalent to the non-treated area) to 100 (complete kill), whereby the results shown in Table 15, were obtained.

TABLE 15

| Comp. No. | Dose of active ingredient (g/ha) | Growth-controlling degree (%) | | | | | | | | | Evaluation day |
|---|---|---|---|---|---|---|---|---|---|---|---|
| | | EC | DS | AV | SS | IP | XS | OS | TR | ZM | GM | |
| 1 | 125 | 20 | 40 | 100 | 60 | 60 | 70 | 30 | — | 30 | 50 | 18 |
| | 500 | 20 | 90 | 100 | 70 | 95 | 95 | 70 | — | 80 | 70 | |
| 3 | 125 | 100 | 99 | 100 | 100 | 90 | 100 | 100 | — | 100 | 100 | 18 |
| | 500 | 100 | 100 | 100 | 100 | 90 | 100 | 100 | — | 100 | 100 | |
| 11 | 125 | 100 | 99 | 100 | 100 | 90 | 100 | 100 | — | 100 | 100 | 18 |
| | 500 | 100 | 100 | 100 | 100 | 90 | 100 | 100 | — | 100 | 100 | |
| 12 | 125 | 0 | 10 | 100 | 40 | 75 | 95 | 70 | 10 | 100 | 60 | 22 |
| 13 | 125 | 0 | 50 | 100 | 90 | 75 | 80 | 0 | 10 | 30 | 45 | 20 |
| 14 | 125 | 10 | 75 | 100 | 20 | 70 | 100 | 95 | 80 | 100 | 90 | 22 |
| 21 | 125 | 100 | 100 | 100 | 100 | 100 | 100 | 95 | — | 100 | 100 | 22 |
| | 500 | 100 | 100 | 100 | 100 | 95 | 100 | 100 | — | 100 | 100 | |
| 22 | 125 | 60 | 40 | 100 | 95 | 80 | 100 | 60 | 30 | 80 | 60 | 23 |
| 24 | 125 | 70 | 80 | 100 | 90 | 80 | 100 | 80 | 80 | 100 | 100 | 20 |
| 25 | 125 | 60 | 80 | 100 | 90 | 90 | 100 | 100 | 95 | 95 | 100 | 23 |
| 32 | 125 | 95 | 75 | — | 75 | 70 | 100 | 70 | — | 100 | 60 | 19 |
| | 500 | 100 | 95 | 100 | 90 | 100 | 100 | 70 | — | 100 | 70 | |
| 35 | 125 | 75 | 75 | 100 | 90 | 80 | 80 | 60 | 60 | 100 | 100 | 21 |
| 49 | 125 | 70 | 70 | 100 | 80 | 80 | 90 | 60 | 60 | 80 | 80 | 22 |
| 51 | 125 | 70 | 80 | 100 | 90 | 100 | 100 | 70 | 70 | 80 | 95 | 22 |
| 60 | 125 | 95 | 100 | 100 | 95 | 95 | 100 | 80 | 100 | 100 | 100 | 22 |
| 61 | 125 | 95 | 100 | 100 | 90 | 100 | 100 | 100 | 100 | 100 | 100 | 22 |
| 69 | 125 | 100 | 90 | 100 | 95 | 95 | 100 | 80 | 80 | 100 | 90 | 22 |
| 71 | 125 | 80 | 70 | 100 | 75 | 90 | — | 80 | 80 | 100 | 80 | 22 |
| 72 | 125 | 95 | 95 | 100 | 80 | 100 | 100 | 70 | 70 | 100 | 95 | 21 |
| 74 | 125 | 80 | 95 | 100 | 80 | 80 | 80 | 80 | 60 | 100 | 80 | 20 |
| 75 | 125 | 90 | 75 | 90 | 50 | 70 | 70 | 70 | — | 100 | 70 | 19 |
| | 500 | 100 | 100 | 95 | 60 | 100 | 90 | 80 | — | 100 | 80 | |
| 88 | 125 | 90 | 80 | 100 | 90 | 100 | 100 | 100 | 60 | 100 | 100 | 22 |
| 90 | 125 | 50 | 20 | 80 | 60 | 70 | 70 | 30 | 10 | 50 | 70 | 22 |
| 94 | 125 | 70 | 80 | 100 | 95 | 100 | 100 | 80 | 60 | 100 | 100 | 20 |
| 101 | 125 | 100 | 95 | 99 | 80 | 100 | 95 | 90 | — | 100 | 100 | 19 |
| | 500 | 100 | 99 | 95 | 95 | 100 | 100 | 99 | — | 100 | 100 | |
| 105 | 125 | 40 | 65 | 100 | 75 | 70 | 70 | 40 | — | 80 | 70 | 18 |
| | 500 | 70 | 90 | 100 | 80 | 80 | 80 | 70 | — | 100 | 80 | |
| 116 | 125 | 60 | 80 | 70 | 70 | 65 | 75 | 40 | — | 60 | 50 | 18 |
| | 500 | 60 | 95 | 90 | 75 | 70 | 80 | 60 | — | 70 | 50 | |

TEST EXAMPLE 2

Paddy field soil was put into a 1/1,000,000 ha pot, and seeds of barnyardgrass (*Echinochloa crus-galli* L.) and japanese bulrush (*Scirpus juncoides*) were sown and slightly covered with soil. Then, the pot was left to stand still in a greenhouse in a state where the depth of flooding water was from 0.5 to 1 cm, and two days later, tubers of japanese ribbon wapato (*Sagittaria pygmaea*) were planted. Thereafter, the depth of flooding water was maintained at a level of from 3 to 4 cm, and when barnyardgrass and japanese bulrush reached a 0.5 leaf stage and japanese ribbon wapato reached to a primary leaf stage, an aqueous diluted solution of a wettable powder having the compound of the present invention formulated in accordance with a usual formulation method, was uniformly applied under submerged condition by a pipette so that the dose of the active ingredient would be at a predetermined level.

On the 14th days after the application of the herbicide, the growth of the respective plants was visually observed and the herbicidal effects were evaluated by the growth-controlling degrees (%) ranging from 0 (equivalent to the non-treated area) to 100 (complete kill), whereby the results shown in Table 16 were obtained.

TABLE 16

| Compound No. | Dose of active ingredient (g/ha) | Growth-controlling degree (%) | | |
|---|---|---|---|---|
| | | EC | SJ | SP |
| 203 | 250 | 10 | 10 | 90 |
| 350 | 250 | 90 | 90 | 100 |
| 377 | 250 | 40 | 10 | 85 |

Notes:
EC: barnyardgrass
SJ: japanese bulrush
SP: japanese ribbon wapato

TEST EXAMPLE 3

Upland field soil was put into a 1/150,000 ha pot, and seeds of various plants were sown. Then, when the plants reached predetermined leaf stages (①  barnyardgrass (*Echinochloa crus-galli* L.), EC: 1.6–2.5 leaf stage, ② crabgrass (*Digitaria sanguinalis* L.), DS: 1.5–2.5 leaf stage, ③ slender amaranth (*Amaranthus viridis* L.), AV: 0.2–1.5 leaf stage, ④ prickly sida (*Sida spinosa* L.), SS: 0.1–1.2 leaf stage, ⑤ tall morningglory (*Ipomoea purpurea* L.), IP:

0.2–2.0 leaf stage, ⑥ common cocklebur (*Xanthium strumarium* L.), XS: 0.2–2.1 leaf stage, ⑦ rice (*Oryza sativa* L.), OS: 1.5–2.2 leaf stage, ⑧ wheat (*Triticum* spp.), TR: 2.0–3.3 leaf stage, ⑨ corn (*Zea mays* L.), ZM: 2.2–3.4 leaf stage, ⑩ soybean (*Glycine max* Merr.), GM: primary leaf—0.2 leaf stage), a wettable powder having the compound of the present invention formulated in accordance with a usual formulation method, was weighed so that the active ingredient would be a predetermined amount, and diluted with water in an amount of 500 l/ha. To the diluted solution, 0.1% (v/v) of an agricultural spreader was added. The herbicide thus adjusted was applied by a small size spray for foliage treatment. On the 17th to 23rd days after the application of the herbicide, the growth of the respective plants was visually observed, and the herbicidal effects were evaluated by the growth-controlling degrees (%) ranging from 0 (equivalent to the non-treated area) to 100 (complete kill), whereby the results shown in Table 17, were obtained.

TABLE 17

| Comp. No. | Dose of active ingredient (g/ha) | EC | DS | AV | SS | IP | XS | OS | TR | ZM | GM | Evaluation day |
|---|---|---|---|---|---|---|---|---|---|---|---|---|
| 70 | 125 | 30 | 50 | 80 | 70 | 60 | 0 | 70 | — | 20 | 40 | 17 |
|  | 500 | 50 | 60 | 90 | 80 | 80 | 70 | 80 | — | 60 | 70 |  |
| 76 | 125 | 0 | 10 | 80 | 40 | 50 | 60 | 30 | 10 | 20 | 0 | 22 |
|  | 500 | 30 | 40 | 80 | 75 | 60 | 80 | 50 | 30 | 70 | 60 |  |
| 82 | 125 | 0 | 0 | 80 | 60 | 60 | 60 | 40 | — | 60 | 30 | 17 |
|  | 500 | 10 | 0 | 80 | 70 | 70 | 70 | 40 | — | 80 | 40 |  |
| 313 | 125 | 30 | 20 | 80 | 10 | 70 | 70 | 40 | 0 | 20 | 30 | 23 |
|  | 500 | 30 | 0 | 100 | 30 | 90 | 95 | 40 | 30 | 40 | 40 |  |
| 485 | 125 | 30 | 10 | 70 | 70 | 60 | 30 | 0 | 10 | 10 | 10 | 21 |
|  | 500 | 40 | 10 | 80 | 60 | 70 | 70 | 30 | 20 | 60 | 30 |  |
| 486 | 125 | 80 | 70 | 100 | 80 | 90 | 80 | 70 | — | 90 | 80 | 20 |
|  | 500 | 90 | 70 | 100 | 90 | 100 | 100 | 80 | — | 100 | 80 |  |
| 487 | 125 | 60 | 60 | 90 | 80 | 70 | 70 | 60 | — | 60 | 60 | 20 |
|  | 500 | 70 | 80 | 100 | 90 | 90 | 70 | 60 | — | 100 | 70 |  |
| 495 | 125 | 40 | 20 | 80 | 80 | 60 | 70 | 20 | 0 | 50 | 40 | 21 |
|  | 500 | 70 | 50 | 90 | 70 | 70 | 70 | 50 | 50 | 70 | 50 |  |
| 496 | 125 | 70 | 50 | 100 | 90 | 80 | 80 | 60 | — | 70 | 80 | 20 |
|  | 500 | 80 | 80 | 100 | 90 | 90 | 100 | 70 | — | 100 | 80 |  |
| 497 | 125 | 70 | 70 | 100 | 90 | 70 | 80 | 50 | — | 70 | 60 | 20 |
|  | 500 | 70 | 80 | 100 | 90 | 90 | 90 | 70 | — | 100 | 70 |  |
| 502 | 125 | 70 | 40 | 100 | 80 | 100 | 100 | 70 | 80 | 100 | 100 | 21 |
| 503 | 125 | 95 | 30 | 100 | 90 | 100 | 100 | 60 | 80 | 100 | 100 | 21 |
| 506 | 125 | 100 | 99 | 100 | 95 | 90 | 100 | 90 | 100 | 100 | 100 | 21 |
|  | 500 | 100 | 100 | 100 | 95 | 100 | 100 | 100 | 100 | 100 | 100 |  |
| 509 | 125 | 100 | 90 | 95 | 80 | 70 | 100 | 70 | 95 | 100 | 100 | 21 |
|  | 500 | 100 | 99 | 100 | 95 | 100 | 100 | 100 | 95 | 100 | 100 |  |
| 510 | 125 | 70 | 70 | 90 | 80 | 90 | 100 | 90 | 90 | 100 | 80 | 21 |
|  | 500 | 100 | 90 | 100 | 90 | 100 | 100 | 95 | 90 | 100 | 90 |  |
| 517 | 125 | 80 | 80 | 90 | 70 | 70 | 90 | 40 | — | 80 | 80 | 21 |
|  | 500 | 90 | 90 | 90 | 80 | 90 | 90 | 50 | — | 80 | 70 |  |
| 521 | 125 | 80 | 60 | 90 | 80 | 100 | 90 | 30 | — | 80 | 80 | 18 |
|  | 500 | 90 | 90 | 90 | 90 | 100 | 90 | 60 | — | 100 | 90 |  |
| 522 | 125 | 60 | 30 | 80 | 60 | 60 | 90 | 30 | — | 70 | 70 | 21 |
|  | 500 | 80 | 70 | 80 | 70 | 80 | 90 | 50 | — | 70 | 70 |  |
| 523 | 125 | 60 | 60 | 90 | 80 | 80 | 80 | 40 | — | 60 | 70 | 20 |
|  | 500 | 70 | 70 | 100 | 90 | 80 | 80 | 50 | — | 90 | 80 |  |
| 526 | 125 | 80 | 60 | 100 | 70 | 60 | 60 | 30 | — | 90 | 70 | 18 |
|  | 500 | 90 | 90 | 100 | 90 | 100 | 90 | 40 | — | 90 | 80 |  |
| 527 | 125 | 70 | 50 | 90 | 70 | 70 | 90 | 10 | — | 80 | 60 | 18 |
|  | 500 | 80 | 90 | 100 | 80 | 90 | 90 | 70 | — | 100 | 80 |  |
| 528 | 125 | 30 | 40 | 70 | 70 | 40 | 50 | 30 | — | 60 | 60 | 21 |
|  | 500 | 70 | 60 | 80 | 80 | 80 | 50 | 60 | — | 70 | 70 |  |
| 531 | 125 | 70 | 70 | 90 | 80 | 60 | 90 | 40 | — | 80 | 80 | 20 |
|  | 500 | 80 | 95 | 90 | 90 | 80 | 90 | 50 | — | 100 | 90 |  |
| 534 | 125 | 70 | 20 | 90 | 70 | 70 | 80 | 40 | 20 | 40 | 20 | 20 |
|  | 500 | 70 | 70 | 90 | 80 | 90 | 90 | 50 | 50 | 60 | 40 |  |
| 539 | 125 | 20 | 0 | 60 | 70 | 40 | 10 | 10 | 0 | 20 | 0 | 21 |
|  | 500 | 10 | 0 | 70 | 60 | 60 | 10 | 10 | 0 | 50 | 10 |  |
| 540 | 125 | 50 | 50 | 90 | 80 | 70 | 20 | 40 | — | 90 | 70 | 20 |
|  | 500 | 60 | 60 | 100 | 80 | 90 | 90 | 60 | — | 70 | 80 |  |
| 541 | 125 | 0 | 20 | 60 | 60 | 60 | 0 | 10 | 10 | 50 | 40 | 20 |
|  | 500 | 40 | 60 | 90 | 80 | 80 | 80 | 40 | 30 | 60 | 60 |  |
| 545 | 125 | 50 | 20 | 90 | 80 | 70 | 70 | 50 | 40 | 70 | 60 | 20 |
|  | 500 | 80 | 95 | 95 | 90 | 90 | 80 | 70 | 70 | 100 | 60 |  |
| 546 | 125 | 70 | 80 | 90 | 80 | 90 | 90 | 60 | — | 80 | 80 | 20 |
|  | 500 | 80 | 90 | 100 | 90 | 90 | 90 | 70 | — | 100 | 80 |  |
| 553 | 125 | 70 | 30 | 100 | 50 | 70 | 60 | 60 | — | 80 | 20 | 20 |
|  | 500 | 80 | 60 | 100 | 70 | 80 | 80 | 70 | — | 80 | 60 |  |
| 560 | 125 | 60 | 10 | 80 | 70 | 60 | 70 | 10 | 40 | 60 | 50 | 21 |
|  | 500 | 80 | 50 | 100 | 90 | 70 | 80 | 50 | 50 | 70 | 60 |  |
| 561 | 125 | 50 | 50 | 90 | 80 | 80 | 80 | 40 | — | 70 | 80 | 20 |
|  | 500 | 80 | 80 | 100 | 90 | 90 | 90 | 70 | — | 100 | 90 |  |

TABLE 17-continued

| Comp. No. | Dose of active ingredient (g/ha) | Growth-controlling degree (%) | | | | | | | | | | Evaluation day |
|---|---|---|---|---|---|---|---|---|---|---|---|---|
| | | EC | DS | AV | SS | IP | XS | OS | TR | ZM | GM | |
| 562 | 125 | 70 | 70 | 90 | 70 | 70 | 80 | 50 | — | 70 | 50 | 20 |
| | 500 | 70 | 70 | 100 | 80 | 90 | 80 | 50 | — | 70 | 60 | |
| 563 | 125 | 80 | 40 | 100 | 70 | 50 | 80 | 70 | — | 70 | 50 | 20 |
| | 500 | 90 | 60 | 100 | 80 | 70 | 80 | 80 | — | 80 | 60 | |
| 674 | 125 | 30 | 10 | 80 | 30 | 70 | 100 | 0 | 10 | 0 | 100 | 21 |
| | 500 | 60 | 10 | 90 | 70 | 100 | 100 | 10 | 20 | 70 | 100 | |
| 675 | 125 | 20 | 20 | 100 | 60 | 60 | 100 | 0 | 0 | 0 | 0 | 20 |
| | 500 | 20 | 40 | 100 | 70 | 80 | 100 | 0 | 10 | 20 | 10 | |
| 680 | 125 | 0 | 20 | 80 | 70 | 60 | 80 | 30 | 20 | 30 | 40 | 21 |
| | 500 | 40 | 30 | 80 | 75 | 80 | 100 | 30 | 30 | 30 | 70 | |

Now, Formulation Examples of the present invention will be given.

FORMULATION EXAMPLE 1

| | |
|---|---|
| (1) Compound No. 11 | 75 parts by weight |
| (2) Sodium N-methyl-N-oleoyl taurate (Geropon T-77, tradename, manufactured by Rhone-Poulenc | 14.5 parts by weight |
| (3) NaCl | 10 parts by weight |
| (4) Dextrin | 0.5 part by weight |

The above components are placed in a high-speed mixing granulator, admixed with 20 wt % of water, granulated, and dried to form water-dispersible granules.

FORMULATION EXAMPLE 2

| | |
|---|---|
| (1) Kaolin | 78 parts by weight |
| (2) Condensate of sodium naphthalene sulfonate and formalin (Laveline FAN, tradename, manufactured by Dai-ichi Kogyo Seiyaku Co., Ltd.) | 2 parts by weight |
| (3) Sodium polyoxyethylene alkylaryl ether sulfate-premix with white carbon (Sorpol 5039, tradename, manufactured by Toho Chemical Industry Co., Ltd.) | 5 parts by weight |
| (4) White carbon (Carplex, tradename, manufactured by Shionogi Seiyaku Co., Ltd.) | 15 parts by weight |

The mixture of the above components (1) to (4) and Compound No. 21 are mixed in a weight ratio of 9:1 to obtain a wettable powder.

FORMULATION EXAMPLE 3

| | |
|---|---|
| (1) Talc micropowder (Hi-Filler No. 10, tradename, manufactured by Matsumura Sangyo Co., Ltd.) | 33 parts by weight |
| (2) Dialkyl sulfosuccinate-premixed with white carbon (Sorpol 5050, tradename, manufactured by Toho Chemical Industry Co., Ltd.) | 3 parts by weight |
| (3) A mixture of polyoxyethylene alkylaryl ether sulfate and a polyoxyethylene monomethyl ether carbonate, premixed with white carbon (Sorpol 5073, tradename, manufactured by Toho Chemical Industry Co., Ltd.) | 4 parts by weight |
| (4) Compound No. 61 | 60 parts by weight |

The above components (1) to (4) are mixed to obtain a wettable powder.

FORMULATION EXAMPLE 4

| | |
|---|---|
| (1) Compound No. 1 | 4 parts by weight |
| (2) Corn oil | 79 parts by weight |
| (3) A mixture of a dialkyl sulfosuccinate, polyoxyethylene nonylphenyl ether, polyoxyethylene hydrogenated castor oil and polyglycerol esters of fatty acid (Sorpol 3815K, tradename, manufactured by Toho Chemical Industry Co., Ltd.) | 15 parts by weight |
| (4) Bentonite-alkylamino complex (New D orben, tradename, manufactured by Shiraishi Kogyo Kaisha, Ltd.) | 2 parts by weight |

The above components (1) to (4) are uniformly mixed and pulverized by a wet-grinding machine (Dyno-mill, manufactured by Willy A. Bachofen) to obtain an oil-based suspension concentrate.

FORMULATION EXAMPLE 5

| | |
|---|---|
| (1) Compound No. 203 | 4 parts by weight |
| (2) Bentonite | 30 parts by weight |
| (3) Calcium carbonate | 61.5 parts by weight |
| (4) Polycarboxylic acid type surfactant (Toxanon GR-31A, tradename, manufactured by Sanyo Chemical Industries Co., Ltd. | 3 parts by weight |
| (5) Calcium lignin sulfonate | 1.5 parts by weight |

Pulverized component (1) and components (2) and (3) are preliminarily mixed, and then components (4) and (5) and water are mixed thereto. The mixture is extruded and granulated, followed by drying and size-adjusting to obtain granules.

FORMULATION EXAMPLE 6

| | | |
|---|---|---|
| (1) Compound No. 350 | 30 parts by weight | |
| (2) A pulverized product of a mixture of kaolinite and sericite (Zieclite, tradename, manufactured by Zieclite Co., Ltd.) | 60 parts by weight | |
| (3) Alkyl naphthalene sulfonate (New Kalgen WG-1, tradename, manufactured by Takemoto Oils and Fats Co., Ltd.) | 5 parts by weight | |
| (4) Polyoxyalkylene allyl phenyl ether sulfate (New Kalgen FS-7, tradename, manufactured by Takemoto Oils and Fats Co., Ltd.) | 5 parts by weight | |

Components (1), (2) and (3) are mixed and passed through a pulverizer, and then component (4) is added thereto. The mixture is kneaded and then extruded and granulated, followed by drying and size-adjusting to obtain water-dispersible granules.

FORMULATION EXAMPLE 7

| | |
|---|---|
| (1) Compound No. 1 | 28 parts by weight |
| (2) Triethanolamine salts of oxyethylated polyarylphenol phosphate (Soprophor FL, tradename, manufactured by Rhone-Poulenc | 2 parts by weight |
| (3) A mixture of polyoxyethylene styryl phenyl ether and alkyl aryl sulfonate (Sorpol 355, tradename, manufactured by Toho Chemical Industry Co., Ltd.) | 1 part by weight |
| (4) Isoparaffin hydrocarbon (IP solvent 1620, tradename, manufactured by Idemitsu Petrochemical Co., Ltd.) | 32 parts by weight |
| (5) Ethylene glycol | 6 parts by weight |
| (6) Water | 31 parts by weight |

The above components (1) to (6) are mixed and pulverized by a wet-grinding machine (Dyno-mill) to obtain a water-based suspension concentrate.

FORMULATION EXAMPLE 8

| | |
|---|---|
| (1) Compound No. 506 | 75 parts by weight |
| (2) Sodium N-methyl-N-oleoyl taurate (Geropon T-77, tradename, manufactured by Rhone-Poulenc | 14.5 parts by weight |
| (3) NaCl | 10 parts by weight |
| (4) Dextrin | 0.5 part by weight |

The above components are placed in a high-speed mixing granulator, admixed with 20 wt % of water, granulated, and dried to form water-dispersible granules.

FORMULATION EXAMPLE 9

| | |
|---|---|
| (1) Kaolin | 78 parts by weight |
| (2) Condensate of sodium naphthalene sulfonate and formalin (Laveline FAN, tradename, manufactured by Dai-ichi Kogyo Seiyaku Co., Ltd.) | 2 parts by weight |
| (3) Sodium polyoxyethylene alkylaryl ether sulfate-premix with white carbon (Sorpol 5039, tradename, manufactured by Toho Chemical Industry Co., Ltd.) | |
| (4) White carbon (Carplex, tradename, manufactured by Shionogi Seiyaku Co., Ltd.) | 15 parts by weight |

The mixture of the above components (1) to (4) and Compound No. 521 are mixed in a weight ratio of 9:1 to obtain a wettable powder.

We claim:

1. A pyridonesulfonylurea compound of the formula (I) or its salt:

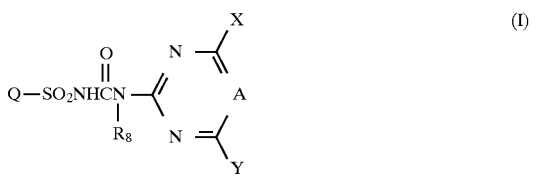

wherein Q is

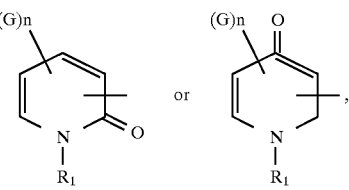

$R_1$ is a hydrogen atom, a $C_{1-6}$ alkyl group which may be substituted, a $C_{2-6}$ alkenyl group which may be substituted, a $C_{2-6}$ alkynyl group which may be substituted, a $C_{1-6}$ alkoxy group which may be substituted, a $C_{1-6}$ alkylthio group which may be substituted, a $C_{1-6}$ alkylcarbonyl group which may be substituted, a $C_{1-6}$ alkoxycarbonyl group which may be substituted, a $C_{1-6}$ alkylsulfinyl group which may be substituted, a $C_{1-6}$ alkylsulfonyl group which may be substituted,

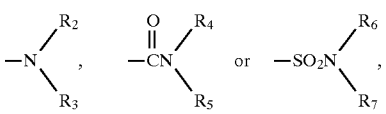

G is a halogen atom, a $C_{1-6}$ alkyl group which may be substituted, a $C_{2-6}$ alkenyl group which may be substituted, a $C_{2-6}$ alkynyl group which may be substituted, a $C_{1-6}$ alkoxy group which may be substituted, a $C_{1-6}$ alkylthio group which may be substituted, a $C_{1-6}$ alkylcarbonyl group which may be substituted, a $C_{1-6}$ alkoxycarbonyl group which may be substituted, a $C_{1-6}$ alkylsulfinyl group which may be substituted, a $C_{1-6}$ alkylsulfonyl group which may be substituted,

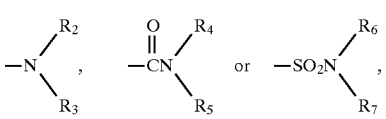

wherein the substituent for each of the alkyl group which may be substituted, the alkenyl group which may be substituted, the alkynyl group which may be substituted, the alkoxy group which may be substituted, the alkylthio group which may be substituted, the alkylcarbonyl group which may be substituted and the alkoxycarbonyl group which may be substituted, is halogen, $C_{1-6}$ alkyl, $C_{1-6}$ alkoxy, $C_{1-6}$ alkylthio, $C_{1-6}$ alkylcarbonyl, $C_{1-6}$ alkoxycarbonyl, $C_{1-6}$ alkylsulfinyl, $C_{1-6}$ alkylsulfonyl, phenyl, substituted phenyl, benzyloxy, substituted benzyloxy, mono $C_{1-6}$ alkylamino, di $C_{1-6}$ alkylamino, —CN or —$NO_2$, the substituent for each of the alkylsulfinyl group which may be substituted and the alkylsulfonyl group which may be substituted is halogen, $C_{1-6}$ alkyl, $C_{1-6}$ alkoxy, phenyl, substituted phenyl, benzyloxy, or substituted benzyloxy, the substituent for each of the substituted phenyl and the substituted benzyloxy is halogen, $C_{1-6}$ alkyl, $C_{1-6}$ alkoxy, $C_{1-6}$ alkylthio, $C_{1-6}$ alkylcarbonyl, $C_{1-6}$ alkoxycarbonyl, $C_{1-6}$ alkylsulfinyl, $C_{1-6}$ alkylsulfonyl, phenyl, benzyloxy, mono $C_{1-6}$ alkylamino, di $C_{1-6}$ alkylamino, —CN or —$NO_2$, each of $R_2$ and $R_3$ which are independent of each other, is a hydrogen atom, a $C_{1-6}$ alkyl group, a $C_{1-6}$ alkylcarbonyl group, a $C_{1-6}$ alkylsulfinyl group or a $C_{1-6}$ alkylsulfonyl group, each of $R_4$, $R_5$ and $R_8$ which are independent of one another, is a hydrogen atom or a $C_{1-6}$ alkyl group, each of $R_6$ and $R_7$ which are independent of each other, is a hydrogen atom, a $C_{1-6}$ alkyl group, a $C_{1-6}$ alkylcarbonyl group or a $C_{1-6}$ alkoxycarbonyl group, n is an integer of from 0 to 3, each of X and Y which are independent of each other, is a halogen atom, a $C_{1-6}$ alkyl group, a halo $C_{1-6}$ alkyl group, a $C_{1-6}$ alkoxyalkyl group, a $C_{1-6}$ alkoxy group, a halo $C_{1-6}$ alkoxy group, a mono $C_{1-6}$ alkylamino group or a di $C_{1-6}$ alkylamino group, and A is CH.

2. The compound or its salt according to claim 1, wherein Q is

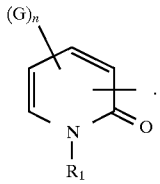

3. The compound or its salt according to claim 1, wherein Q is

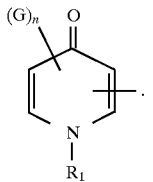

4. The compound or its salt according to claim 1, 2 or 3, wherein $R_1$ is a hydrogen atom, an alkyl group which may be substituted, an alkenyl group which may be substituted, an alkynyl group which may be substituted, an alkoxy group which may be substituted, an alkoxycarbonyl group which may be substituted, an alkylsulfonyl group which may be substituted or

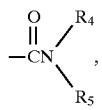

G is a halogen atom, an alkyl group which may be substituted, an alkoxy group which may be substituted, an alkylthio group which may be substituted,

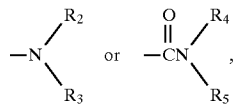

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is an integer of from 0 to 3, each of X and Y which are independent of each other, is a halogen atom, an alkyl group, an alkoxy group or a haloalkoxy group, and A is CH.

5. The compound or its salt according to claim 1, 2 or 3, wherein $R_1$ is a hydrogen atom, an alkyl group which may be substituted, an alkenyl group, an alkynyl group, an alkoxy group, an alkoxycarbonyl group, an alkylsulfonyl group or

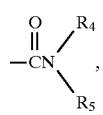

G is a halogen atom, an alkyl group which may be substituted, an alkoxy group which may be substituted, an alkylthio group,

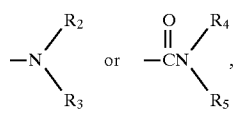

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is 0 or 1, each of X and Y which are independent of each other, is a halogen atom, an alkyl group or an alkoxy group, and A is CH.

6. The compound or its salt according to claim 1, 2 or 3, wherein $R_1$ is a hydrogen atom, an alkyl group which may be substituted by at least one substituent selected from the group consisting of a halogen atom, an alkyl group, an alkoxy group, an alkylthio group, an alkylcarbonyl group, an alkoxycarbonyl group, an alkylsulfinyl group, an alkylsulfonyl group, a phenyl group and a benzyloxy group, an alkenyl group, an alkynyl group, an alkoxy group, an alkoxycarbonyl group, an alkylsulfonyl group or

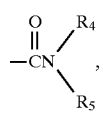

G is a halogen atom, an alkyl group which may be substituted by a halogen atom, an alkoxy group which may be substituted by a halogen atom, an alkylthio group,

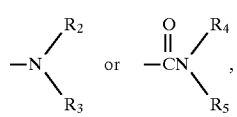

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is 0 or 1, each of X and Y which are independent of each other, is a halogen atom, an alkyl group or an alkoxy group, and A is CH.

7. A herbicidal composition comprising a herbicidally effective amount of the pyridonesulfonylurea compound of claim 1, and an agricultural adjuvant.

8. A method for controlling noxious weeds, which comprises applying to the weeds a herbicidally effective amount of the pyridonesulfonylurea compound of claim 1.

9. The herbicidal composition according to claim 7, wherein Q is

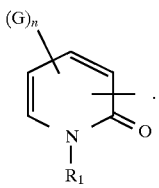

10. The herbicidal composition according to claim 7, wherein Q is

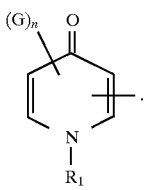

11. The herbicidal composition according to claim 7, 9 or 10, wherein $R_1$ is a hydrogen atom, an alkyl group which may be substituted, an alkenyl group which may be substituted, an alkynyl group which may be substituted, an alkoxy group which may be substituted, an alkoxycarbonyl group which may be substituted, an alkylsulfonyl group which may be substituted or

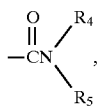

G is a halogen atom, an alkyl group which may be substituted, an alkoxy group which may be substituted, an alkylthio group which may be substituted,

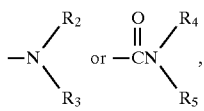

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is an integer of from 0 to 3, each of X and Y which are independent of each other, is a halogen atom, an alkyl group, an alkoxy group or a haloalkoxy group, and A is CH.

12. The herbicidal composition according to claim 7, 9 or 10, wherein $R_1$ is a hydrogen atom, an alkyl group which may be substituted, an alkenyl group, an alkynyl group, an alkoxy group, an alkoxycarbonyl group, an alkylsulfonyl group or

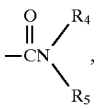

G is a halogen atom, an alkyl group which may be substituted, an alkoxy group which may be substituted, an alkylthio group,

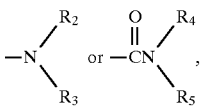

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is 0 or 1, each of X and Y which are independent of each other, is a halogen atom, an alkyl group or an alkoxy group, and A is CH.

13. The herbicidal composition according to claim 7, 9 or 10, wherein $R_1$ is a hydrogen atom, an alkyl group which may be substituted by at least one substituent selected from the group consisting of a halogen atom, an alkyl group, an alkoxy group, an alkylthio group, an alkylcarbonyl group, an alkoxycarbonyl group, an alkylsulfinyl group, an alkylsulfonyl group, a phenyl group and a benzyloxy group, an alkenyl group, an alkynyl group, an alkoxy group, an alkoxycarbonyl group, an alkylsulfonyl group or

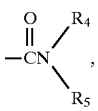

G is a halogen atom, an alkyl group which may be substituted by a halogen atom, an alkoxy group which may be substituted by a halogen atom, an alkylthio group,

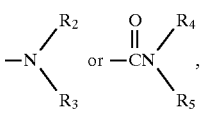

each of $R_2$ and $R_3$ which are independent of each other, is a hydrogen atom or an alkyl group, each of $R_4$ and $R_5$ which are independent of each other, is an alkyl group, $R_8$ is a hydrogen atom, n is 0 or 1, each of X and Y which are independent of each other, is a halogen atom, an alkyl group or an alkoxy group, and A is CH.

14. A process for producing apyridonesulfonylurea compound of the formula (I) or its salt:

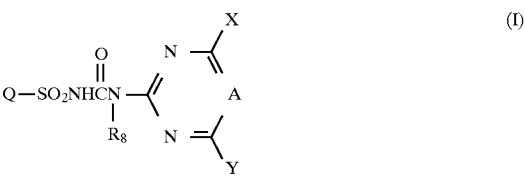

wherein Q is

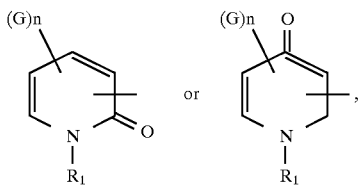

$R_1$ is a hydrogen atom, a $C_{1-6}$ alkyl group which may be substituted, a $C_{2-6}$ alkenyl group which may be substituted, a $C_{2-6}$ alkynyl group which may be substituted, a $C_{1-6}$ alkoxy group which may be substituted, a $C_{1-6}$ alkylthio group which may be substituted, a $C_{1-6}$ alkylcarbonyl group which may be substituted, a $C_{1-6}$ alkoxycarbonyl group which may be substituted, a $C_{1-6}$ alkylsulfinyl group which may be substituted, a $C_{1-6}$ alkylsulfonyl group which may be substituted,

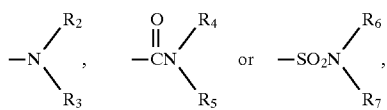

G is a halogen atom, a $C_{1-6}$ alkly group which may be substituted, a $C_{2-6}$ alkenyl group which may be substituted, a $C_{2-6}$ alkynyl group which may be substituted, a $C_{1-6}$ alkoxy group which may be substituted, a $C_{1-6}$ alkylthio group which may be substituted, a $C_{1-6}$ alkylcarbonyl group which may be substituted, a $C_{1-6}$ alkoxycarbonyl group which may be substituted, a $C_{1-6}$ alkylsulfinyl group which may be substituted, a $C_{1-6}$ alkylsulfonyl group which may be substituted,

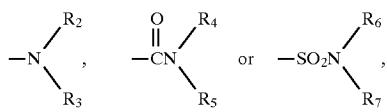

wherein the substituent for each of the alkyl group which may be substituted, the alkenyl group which may be substituted, the alkynyl group which may be substituted, the alkoxy group which may be substituted, the alkylthio group which may be substituted, the alkylcarbonyl group which may be substituted and the alkoxycarbonyl group which may be substituted, is halogen, $C_{1-6}$ alkyl, $C_{1-6}$ alkoxy, $C_{1-6}$ alkylthio, $C_{1-6}$ alkylcarbonyl, $C_{1-6}$ alkoxycarbonyl, $C_{1-6}$ alkylsulfinyl, $C_{1-6}$ alkylsulfonyl, phenyl, substituted phenyl, benzyloxy, substituted benzyloxy, mono $C_{1-6}$ alkylamino, di $C_{1-6}$ alkylamino, —CN or —$NO_2$, the substituent for each of the alkylsulfinyl group which may be substituted and the alkylsulfonyl group which may be substituted is halogen, $C_{1-6}$ alkyl, $C_{1-6}$ alkoxy, phenyl, substituted phenyl, benzyloxy, or substituted benzyloxy, the substituent for each of the substituted phenyl and the substituted benzyloxy is halogen, $C_{1-6}$ alkyl, $C_{1-6}$ alkoxy, $C_{1-6}$ alkylthio, $C_{1-6}$ alkylcarbonyl, $C_{1-6}$ alkoxycarbonyl, $C_{1-6}$ alkylsulfinyl, $C_{1-6}$ alkylsulfonyl, phenyl, benzyloxy, mono $C_{1-6}$ alkylamino, di $C_{1-6}$ alkylamino, —CN or —$NO_2$, each of $R_2$ and $R_3$ which are independent of each other, is a hydrogen atom, a $C_{1-6}$ alkyl group, a $C_{1-6}$ alkylcarbonyl group, a $C_{1-6}$ alkylsulfinyl group or a $C_{1-6}$ alkylsulfonyl group, each of R 4, $R_5$ and $R_8$ which are independent of one another, is a hydrogen atom or a $C_{1-6}$ alkyl group, each of $R_6$ and $R_7$ which are independent of each other, is a hydrogen atom, a $C_{1-6}$ alkyl group, a $C_{1-6}$ alkylcarbonyl group or a $C_{1-6}$ alkoxycarbonyl group, n is an integer of from 0 to 3, each of X and Y which are independent of each other, is a halogen atom, a $C_{1-6}$ alkyl group, a halo $C_{1-6}$ alkyl group, a $C_{1-6}$ alkoxyalkyl group, a $C_{1-6}$ alkoxy group, a halo $C_{1-6}$ alkoxy group, a mono $C_{1-6}$ alkylamino group or a di $C_{1-6}$ alkylamino group, and A is CH, which comprises reacting a pyridone compound of the formula (II):

wherein Q is as defined above, $Z_1$ is —$NH_2$, [—NCO or —$NHCO_2R_9$,] and $R_9$ is an alkyl group or an aryl group, with an azine compound of the formula (III):

wherein X, Y and A are as defined above, $Z_2$ is —$N(R_8)CO_2R_9$ [or —NCO, when $Z_1$ is —$NH_2$, or —$NHR_8$, when $Z_1$ is —NCO or —$NHCO_2R_9$], and $R_8$ and $R_9$ are as defined above, and if necessary, carrying out a salt-forming reaction.

* * * * *